(12) United States Patent
Metz et al.

(10) Patent No.: US 8,236,818 B2
(45) Date of Patent: Aug. 7, 2012

(54) SUBSTITUTED IMIDAZOPYRIDINE DERIVATIVES AS MELANOCORTIN-4 RECEPTOR ANTAGONISTS

(75) Inventors: Günther Metz, Lörrach (DE); Holger Deppe, Füllinsdorf (CH); Ulrich Abel, Heidelberg (DE); Achim Feurer, Auggen (DE); Inge Ott, Ketsch (DE); Sonja Nordhoff, Arlesheim (CH); Michael Soeberdt, Rheinfelden (DE); Barbara Hoffmann-Enger, Therwil (CH); Philipp Weyermann, Sissach (CH); Hervé Siendt, Ranspach-le-Haut (FR); Christian Rummey, Basel (CH); Miroslav Terinek, Bubendorf (CH); Marco Hennenböhle, Rheinfelden (DE); Holger Herzner, Rümmingen (DE); Cesare Mondadori, Reinach (CH)

(73) Assignee: Santhera Pharmaceuticals (Schweiz) AG, Liestal (CH)

( * ) Notice: Subject to any disclaimer, the term of this patent is extended or adjusted under 35 U.S.C. 154(b) by 381 days.

(21) Appl. No.: 12/530,676

(22) PCT Filed: Mar. 28, 2008

(86) PCT No.: PCT/EP2008/002498
§ 371 (c)(1),
(2), (4) Date: Dec. 8, 2009

(87) PCT Pub. No.: WO2008/116665
PCT Pub. Date: Oct. 2, 2008

(65) Prior Publication Data
US 2010/0093697 A1    Apr. 15, 2010

Related U.S. Application Data

(60) Provisional application No. 60/920,500, filed on Mar. 28, 2007.

(30) Foreign Application Priority Data

Mar. 28, 2007   (EP) .................................... 07006422

(51) Int. Cl.
*A61K 31/437*   (2006.01)
*C07D 471/04*   (2006.01)
(52) U.S. Cl. ....................... 514/300; 546/121
(58) Field of Classification Search .................. 546/121; 514/300
See application file for complete search history.

(56) References Cited

U.S. PATENT DOCUMENTS
4,767,755 A    8/1988   George et al.

FOREIGN PATENT DOCUMENTS
WO   WO 02/46158 A2    6/2002
WO   WO 02/066478 A1   8/2002
WO   WO 03/006471 A1   1/2003
WO   WO 2005/121100 A1  12/2005

OTHER PUBLICATIONS

West, Anthony R., Solid State Chemistry and its Applications, Wiley, New York, 1988, pp. 358 & 365.*
Vergoni et. al., "Melanocortins and feeding behavior", Biomed & Pharmacother 2000; 54: 129-34.*
International Search Report for corresponding International Patent Application No. PCT/EP2008/002498 dated Aug. 28, 2008 (2 pages).

* cited by examiner

*Primary Examiner* — Charanjit Aulakh
(74) *Attorney, Agent, or Firm* — Kilyk & Bowersox, P.L.L.C.

(57) ABSTRACT

The present invention relates to substituted imidazopyridine derivatives as melanocortin-4 receptor (MC-4R) modulators, in particular as melanocortin-4 receptor antagonists. The antagonists are useful for the treatment of disorders and diseases such as cancer cachexia, muscle wasting, anorexia, amyotrophic lateral sclerosis (ALS), anxiety and depression.

14 Claims, No Drawings

SUBSTITUTED IMIDAZOPYRIDINE DERIVATIVES AS MELANOCORTIN-4 RECEPTOR ANTAGONISTS

This application is a National Stage Application of PCT/EP2008/002498, filed Mar. 28, 2008, which claims priority from European Patent Application No. 07006422.5, filed Mar. 28, 2007, and U.S. Provisional Patent Application No. 60/920,500, filed Mar. 28, 2007.

FIELD OF THE INVENTION

The present invention relates to substituted imidazopyridine derivatives as melanocortin-4 receptor modulators. Depending on the structure and the stereochemistry, melanocortin-4 receptor modulators are either agonists or antagonists. The compounds of the invention are selective antagonists of the human melanocortin-4 receptor (MC-4R). The antagonists are useful for the treatment of disorders and diseases such as cancer cachexia, muscle wasting, anorexia, amytrophic lateral sclerosis (ALS), anxiety and depression.

BACKGROUND OF THE INVENTION

Melanocortins (MCs) stem from pro-opiomelanocortin (POMC) via proteolytic cleavage. These peptides, adrenocorticotropic hormone (ACTH), α-melanocyte-stimulating hormone (α-MSH), β-MSH and γ-MSH, range in size from 12 to 39 amino acids. The most important endogenous agonist for central MC-4R activation appears to be the tridecapeptide α-MSH. Among MCs, it was reported that α-MSH acts as a neurotransmitter or neuromodulator in the brain. MC peptides, particularly α-MSH, have a wide range of effects on biological functions including feeding behavior, pigmentation and exocrine function. The biological effects of α-MSH are mediated by a sub-family of 7-transmembrane G-protein-coupled receptors, termed melanocortin receptors (MC-Rs). Activation of any of these MC-Rs results in stimulation of cAMP formation.

To date, five distinct types of receptor subtype for MC (MC-1R to MC-5R) have been identified and these are expressed in different tissues.

MC-1R was first found in melanocytes. Naturally occurring inactive variants of MC-1R in animals were shown to lead to alterations in pigmentation and a subsequent lighter coat color by controlling the conversion of phaeomelanin to eumelanin through the control of tyrosinase. From these and other studies, it is evident that MC-1R is an important regulator of melanin production and coat color in animals and skin color in humans. The MC-2R is expressed in the adrenal gland representing the ACTH receptor. The MC-2R is not a receptor for α-MSH but is the receptor for the adrenocorticotropic hormone I (ACTH I).

The MC-3R is expressed in the brain (predominately located in the hypothalamus) and peripheral tissues like gut and placenta, and knock-out studies have revealed that the MC-3R may be responsible for alterations in feeding behavior, body weight and thermogenesis.

The MC-4R is primarily expressed in the brain. Overwhelming data support the role of MC-4R in energy homeostasis. Genetic knock-outs and pharmacologic manipulation of MC-4R in animals have shown that agonizing the MC-4R causes weight loss and antagonizing the MC-4R produces weight gain (A. Kask, et al., "Selective antagonist for the melanocortin-4 receptor (HS014) increases food intake in free-feeding rats," Biochem. Biophys. Res. Commun., 245: 90-93 (1998)).

MC-5R is ubiquitously expressed in many peripheral tissues including white fat, placenta and a low level of expression is also observed in the brain. However its expression is greatest in exocrine glands. Genetic knock-out of this receptor in mice results in altered regulation of exocrine gland function, leading to changes in water repulsion and thermoregulation. MC-5R knockout mice also reveal reduced sebaceous gland lipid production (Chen et al., Cell, 91: 789-798 (1997)).

Attention has been focused on the study of MC-3R and MC-4R modulators and their use in treating body weight disorders, such as obesity and anorexia. However, evidence has shown that the MC peptides have potent physiological effects besides their role in regulating pigmentation, feeding behavior and exocrine function. In particular, α-MSH recently has been shown to induce a potent anti-inflammatory effect in both acute and chronic models of inflammation including inflammatory bowel-disease, renal ischemia/reperfusion injury and endotoxin-induced hepatitis. Administration of α-MSH in these models results in substantial reduction of inflammation-mediated tissue damage, a significant decrease in leukocyte infiltration and a dramatic reduction in elevated levels of cytokines and other mediators to near baseline levels. Recent studies have demonstrated that the anti-inflammatory actions of α-MSH are mediated by MC-1R. The mechanism by which agonism of MC-1R results in an anti-inflammatory response is likely through inhibition of the pro-inflammatory transcription activator, NF-κB. NF-κB is a pivotal component of the pro-inflammatory cascade, and its activation is a central event in initiating many inflammatory diseases. Additionally, anti-inflammatory actions of α-MSH may be, in part, mediated by agonism of MC-3R and/or MC-5R.

A specific single MC-R that may be targeted for the control of obesity has not yet been identified, although evidence has been presented that MC-4R signaling is important in mediating feeding behavior (S. Q. Giraudo et al., "Feeding effects of hypothalamic injection of melanocortin-4 receptor ligands," Brain Research, 80: 302-306 (1998)). Further evidence for the involvement of MC-Rs in obesity includes: 1) the agouti ($A^{vy}$) mouse which ectopically expresses an antagonist of the MC-1R, MC-3R and MC-4R is obese, indicating that blocking the action of these three MC-R's can lead to hyperphagia and metabolic disorders; 2) MC-4R knockout mice (D. Huszar et al., Cell, 88: 131-141 (1997)) recapitulate the phenotype of the agouti mouse and these mice are obese; 3) the cyclic heptapeptide melanotanin II (MT-II) (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; 4) chronic intraperitoneal treatment of Zucker fatty rats with an α-NDP-MSH derivative (HP-228) has been reported to activate MC-1R, -3R, -4R, and -5R and to attenuate food intake and body weight gain over a 12 week period (I. Corcos et al., "HP-228 is a potent agonist of melanocortin receptor-4 and significantly attenuates obesity and diabetes in Zucker fatty rats," Society for Neuroscience Abstracts, 23: 673 (1997)).

MC-4R appears to play a role in other physiological functions as well, namely controlling grooming behavior, erection and blood pressure. Erectile dysfunction denotes the medical condition of inability to achieve penile erection sufficient for successful intercourse. The term "impotence" is often employed to describe this prevalent condition. Synthetic melanocortin receptor agonists have been found to initiate erections in men with psychogenic erectile dysfunction (H. Wessells et al., "Synthetic Melanotropic Peptide Initiates Erections in Men With Psychogenic Erectile Dysfunction: Double-Blind, Placebo Controlled Crossover Study," J. Urol., 160: 389-393, 1998). Activation of melanocortin receptors of the brain appears to cause normal stimulation of sexual arousal. Evidence for the involvement of MC-R in male and/or female sexual dysfunction is detailed in WO 00/74679.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II diabetes" or "Non-Insulin Dependent Diabetes Mellitus" (NIDDM) is the form of diabetes which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle, and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL, is known as Syndrome X. MC-4R agonists might be useful in the treatment of NIDDM and Syndrome X.

Among MC receptor subtypes, the MC4 receptor is also of interest in terms of the relationship to stress and the regulation of emotional behavior, as based on the following findings. Stress initiates a complex cascade of responses that include endocrine, biochemical and behavioral events. Many of these responses are initiated by release of corticotropin-releasing factor (CRF) (Owen M J and Nemeroff C B (1991) Physiology and pharmacology of corticotrophin releasing factor. *Pharmacol Rev* 43: 425-473). In addition to activation of the brain CRF system, there are several lines of evidence that melanocortins (MCs), which stem from proopiomelanocortin by enzymatic processing, mediate important behavioral and biochemical responses to stress and, consequently, stress-induced disorders like anxiety and depression (Anxiolytic-Like and Antidepressant-Like Activities of MCL0129 (1-[(S)-2-(4-Fluorophenyl)-2-(4-isopropylpiperadin-1-yl) ethyl]-4-[4-(2-methoxynaphthalen-1-yl)butyl]piperazine), a Novel and Potent Nonpeptide Antagonist of the Melanocortin-4 Receptor; Shigeyuki Chaki et al, J. Pharm. Exp. Ther. (2003) 304(2), 818-26).

Chronic diseases, such as malignant tumors or infections, are frequently associated with cachexia resulting from a combination of a decrease in appetite and a loss of lean body mass. Extensive loss of lean body mass is often triggered by an inflammatory process and is usually associated with increased plasma levels of cytokines (e.g. TNF-α), which increase the production of α-MSH in the brain. Activation of MC4 receptors in the hypothalamus by α-MSH reduces appetite and increases energy expenditure. Experimental evidence in tumor bearing mice suggests that cachexia can be prevented or reversed by genetic MC4 receptor knockout or MC4 receptor blockade. The increased body weight in the treated mice is attributable to a larger amount of lean body mass, which mainly consists of skeletal muscle (Marks D. L. et al. Role of the central melanocortin system in cachexia. Cancer Res. (2001) 61: 1432-1438).

Clinical observations indicate, that progression of amytrophic lateral sclerosis (ALS) might be inversely correlated with body weight (e.g. Ludolph A C, Neuromuscul Disord. (2006) 16 (8):530-8). Accordingly, MC-4R inhibitors could be used to treat ALS patients.

Melanocortin-4-receptor modulators have been previously described in the literature. For example, substituted phenylpiperidine derivatives have been synthesized and explored as MC-4R agonists as well as antagonists.

In view of the unresolved deficiencies in treatment of various diseases and disorders as discussed above, it is an object of the present invention to provide novel compounds with improved ability to cross the blood brain barrier, which are useful as melanocortin-4 receptor antagonists to treat cancer cachexia, muscle wasting, anorexia, amytrophic lateral sclerosis (ALS), anxiety, depression and other diseases with MC-4R involvement.

Surprisingly, it has been found that novel imidazopyridines according to formula (I) shown below solve the object of the present invention.

SUMMARY OF THE INVENTION

The present invention relates to substituted imidazopyridine derivatives of structural formula (I)

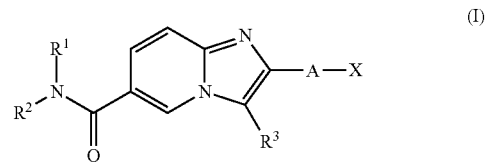

wherein $R^1$, $R^2$, $R^3$, A and X are defined as described below.

The imidazopyridine derivatives of structural formula (I) are effective as melanocortin receptor modulators and are particularly effective as selective melanocortin-4 receptor (MC-4R) antagonists. They are therefore useful for the treatment of disorders where the inactivation of the MC-4R is involved. The antagonists are useful for the treatment of disorders and diseases such as cancer cachexia, muscle wasting, anorexia, amytrophic lateral sclerosis, anxiety and depression.

Thus, the present inventions relates to compounds of formula (I) for the treatment and/or prophylaxis of cancer cachexia, muscle wasting, anorexia, amytrophic lateral sclerosis (ALS), anxiety and depression.

In a further aspect, the invention relates to the use of a compound of formula (I) for the preparation of a medicament for the treatment and/or prophylaxis of cancer cachexia, muscle wasting, anorexia, amytrophic lateral sclerosis (ALS), anxiety and depression.

The present invention also relates to pharmaceutical compositions comprising the compounds of the present invention and a pharmaceutically acceptable carrier.

DETAILED DESCRIPTION OF THE INVENTION

The present invention relates to substituted imidazopyridine derivatives useful as melanocortin receptor modulators, in particular, selective MC-4R antagonists.

Substituted N-benzyl-N-methyl-2-phenyl-5-diethylamido-3-methylamino-imidazo[1,2-a]pyridines are known from WO-A-02/066478 which describes antagonists of gonadotropin releasing hormone. The present invention relates to novel imidazopyridines which are used as antagonists of MC-4R.

The compounds of the present invention are represented by structural formula (I)

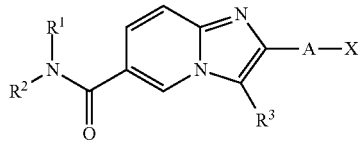

(I)

and enantiomers, diastereomers, tautomers, solvates and pharmaceutically acceptable salts thereof,
wherein
A is —NH—, —CH$_2$—, —CH$_2$—CH$_2$— or a bond;
X is H,
  phenyl,
  phenyl which is fused with a saturated heterocyclic 5- or 6-membered ring, wherein the heterocyclic ring may contain 1 or 2 heteroatoms selected from O and N and wherein the heterocyclic ring may further be optionally substituted by an oxo group,
  4 to 8-membered saturated or unsaturated heterocyclyl containing 1 or 2 heteroatoms selected from N, O and S,
  5- to 6-membered heteroaryl containing 1 or 2 heteroatoms selected from N, O and S, or
  —C(O)—R$^6$,
  wherein each phenyl, heterocyclyl and heteroaryl is optionally substituted by 1 to 3 R$^{14}$ and/or 1 R$^{4b}$ and/or 1 R$^5$;
R$^1$ and R$^2$ are independently from each other selected from
  H,
  C$_{1-6}$ alkyl,
  C$_{1-6}$ alkylene-O—C$_{1-6}$ alkyl,
  C$_{1-3}$ alkylene-heterocyclyl,
  C$_{1-6}$ alkylene-C$_{3-7}$ cycloalkyl,
  wherein each alkyl, alkylene, heterocyclyl and cycloalkyl is optionally substituted by OH, or
  R$^1$ and R$^2$ form together with the nitrogen atom to which they are attached a 5- to 6-membered ring which may additionally contain 1 oxygen atom in the ring and which is optionally substituted by one or more substituents selected from OH, C$_{1-6}$ alkyl, O—C$_{1-6}$ alkyl, C$_{0-3}$ alkylene-C$_{3-5}$ cycloalkyl, C$_{1-6}$ alkylene-O—C$_{1-6}$ alkyl or (CH$_2$)$_{0-3}$-phenyl;
R$^{4a}$ is halogen,
  CN,
  C$_{1-6}$ alkyl, optionally substituted with one or more halogen atoms,
  O—C$_{1-6}$ alkyl, optionally substituted with one or halogen atoms, or
  OH;
R$^{4b}$ is C(O)NH$_2$,
  C(O)OH,
  C(O)NH—C$_{1-6}$ alkyl,
  C(O)N—(C$_{1-6}$ alkyl)$_2$,
  SO$_2$—C$_{1-6}$ alkyl,
  C(O)NH—SO$_2$—C$_{1-6}$ alkyl,
  oxo, whereby the ring is at least partially saturated,
  NH$_2$,
  NH—C$_{1-6}$ alkyl,
  N—(C$_{1-6}$ alkyl)$_2$,
  NH—SO$_2$—CH$_3$, or
  NH—SO$_2$—CF$_3$;
R$^5$ is 5 to 6-membered saturated or unsaturated heterocyclyl containing 1 to 3 heteroatoms selected from N, O and S or
  5 to 6-membered heteroaryl containing 1 to 3 heteroatoms selected from N, O and S,
  wherein the heterocyclyl and the heteroaryl are optionally substituted by 1 or 2 R$^{14}$;
R$^6$ is H,
  C$_{1-6}$ alkyl, optionally substituted with one or more halogen atoms, phenyl or
  4 to 8-membered saturated or unsaturated heterocyclyl containing 1 to 3 heteroatoms selected from N, O and S,
  wherein each phenyl or heterocyclyl is optionally substituted by 1 to 3 R$^{14}$ and/or 1R$^8$;
R$^3$ is —(CR$^8$R$^9$)$_n$-T;
R$^8$ and R$^9$ are independently from each other selected from
  H,
  OH,
  halogen,
  C$_{1-6}$ alkyl, and
  O—C$_{1-6}$ alkyl;
n is 1, 2, 3, 4, 5 or 6;
T is

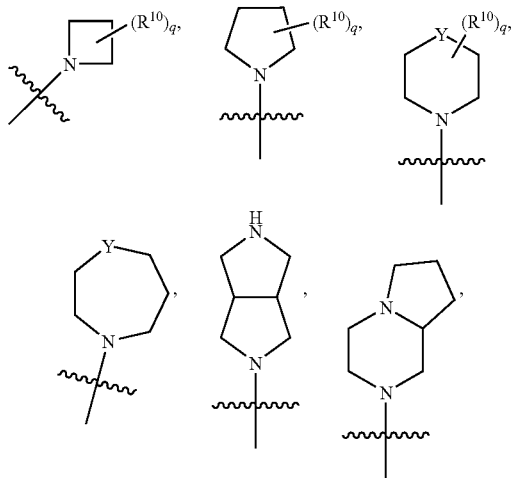

or NR$^{12}$R$^{13}$;
R$^{10}$ is H,
  NH$_2$,
  OH,
  C$_{1-6}$ alkyl, optionally substituted by one or more substituents selected from halogen, OH and O—C$_{1-6}$ alkyl,
  O—C$_{1-6}$ alkyl, wherein alkyl is optionally substituted by one or more substituents selected from halogen, OH and O—C$_{1-6}$ alkyl,
  halogen,
  NH(C$_{1-6}$ alkyl),
  N(C$_{1-6}$ alkyl)$_2$,
  phenyl or
  heteroaryl,
  wherein phenyl and heteroaryl are optionally substituted by 1 to 3 R$^{4a}$;
q is 1 or 2;
Y is CH$_2$, NR$^{11}$ or O;
R$^{11}$ is H,
  C$_{1-6}$ alkyl, or
  (CH$_2$)$_{0-6}$—C$_{3-7}$ cycloalkyl;

$R^{12}$ and $R^{13}$ are independently from each other selected from
- H,
- $C_{1-6}$ alkyl,
- $C_{2-6}$ alkenyl,
- $C_{2-6}$ alkinyl,
- $(CH_2)_{0-2}$—$C_{3-7}$ cycloalkyl and
- $C_{1-6}$ alkylene-O—$C_{1-6}$ alkyl,
  wherein $C_{1-6}$ alkyl, $C_{1-6}$ alkylene and $C_{3-7}$ cycloalkyl are optionally substituted by 1 to 3 $R^{14}$;

$R^{14}$ is halogen,
- CN,
- $C_{1-6}$ alkyl, optionally substituted with one or more substituents selected from halogen, OH, O—$C_{1-6}$ alkyl, O—$C_{3-7}$ cycloalkyl, O—C(O)$C_{1-6}$ alkyl, O—C(O)$C_{3-7}$ cycloalkyl,
- O—$C_{1-6}$ alkyl, optionally substituted with one or more substituents selected from halogen, OH, O—$C_{1-6}$ alkyl, O—$C_{3-7}$ cycloalkyl, O—C(O)$C_{1-6}$ alkyl, O—C(O)$C_{3-7}$ cycloalkyl, or
- OH.

In a preferred embodiment, the variant A represents —NH— or a bond. More preferably, A represents a bond.

It is further preferred that $R^1$ and $R^2$ independently from each other represent $C_{3-6}$ alkyl or that $R^1$ and $R^2$ form together with the nitrogen atom to which they are attached a 5 to 6-membered ring which may additionally contain one oxygen atom in the ring and which is optionally substituted by one or more substituents selected from OH, $C_{1-6}$ alkyl, $C_{0-3}$ alkylene-$C_{3-5}$ cycloalkyl, O—$C_{1-6}$ alkyl, $C_{1-6}$alkylene-O—$C_{1-6}$ alkyl or $(CH_2)_{0-3}$-phenyl. More preferably, $R^1$ and $R^2$ independently from each other represent $C_{3-6}$ alkyl.

In a preferred embodiment, the variant T is $NR^{12}R^{13}$. Therein, the variants $R^{12}$ and $R^{13}$ are preferably independently from each other selected from H, $C_{1-3}$ alkyl or $(CH_2)_{0-2}$—$C_{3-6}$ cycloalkyl, wherein alkyl and cycloalkyl are optionally substituted by 1 to 3 $R^{14}$.

In an alternative preferred embodiment, the variant T is selected from

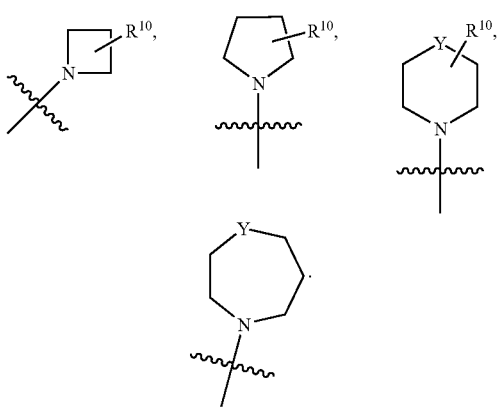

It is preferred that the variant Y is $CH_2$ or $NR^{11}$. Preferably, $R^{11}$ is hydrogen.

It is further preferred that $R^{10}$ is selected from H, $NH_2$, $C_{1-6}$ alkyl, $NH(C_{1-6}$ alkyl) or $N(C_{1-6}$alkyl$)_2$. More preferably, $R^{10}$ is H, $NH_2$ or $C_{1-6}$ alkyl.

Regarding the variant X, said variant preferably represents H, phenyl which is fused with a saturated heterocyclic 6-membered ring, wherein the heterocyclic ring may contain 1 or 2 heteroatoms selected from O and N and wherein the heterocyclic ring may further be optionally substituted by an oxo group, or X represents a 4 to 8-membered saturated or unsaturated heterocyclyl containing 1 or 2 heteroatoms selected from N, O and S, wherein each phenyl and heterocyclyl is optionally substituted by 1 to 3 $R^{14}$ and/or 1$R^{4b}$ and/or 1 $R^5$.

In an equally preferred embodiment, the variant X represents phenyl or a 5 to 6-membered heteroaryl containing 1 or 2 heteroatoms selected from N, O and S, wherein each phenyl and heteroaryl is optionally substituted by 1 to 3 $R^{14}$ and/or 1$R^{4b}$ and/or $R^5$. More preferably, X is phenyl or pyridyl, most preferably X is phenyl.

Compounds of the formula (I) in which some or all of the above-mentioned groups have the preferred or more preferred meanings are also an object of the present invention.

In the above and the following, the employed terms have the meaning as described below:

Alkyl is a straight chain or branched alkyl having 1, 2, 3, 4, 5 or 6 carbon atoms, such as methyl, ethyl, n-propyl, isopropyl, n-butyl, isobutyl, tert-butyl, n-pentyl, isopentyl, neopentyl, or hexyl.

Alkenyl is a straight chain or branched alkyl having 2, 3, 4, 5 or 6 carbon atoms and one to three double bonds, preferably one or two double bonds, most preferably one double bound. Preferred examples of a $C_{2-6}$ alkenyl group are ethenyl, prop-1-enyl, prop-2-enyl, isoprop-1-enyl, n-but-1-enyl, n-but-2-enyl, n-but-3-enyl, isobut-1-enyl, isobut-2-enyl, n-pent-1-enyl, n-pent-2-enyl, n-pent-3-enyl, n-pent-4-enyl, n-pent-1,3-enyl, isopent-1-enyl, isopent-2-enyl, neopent-1-enyl, n-hex-1-enyl, n-hex-2-enyl, n-hex-3-enyl, n-hex-4-enyl, n-hex-5-enyl, n-hex-1,3-enyl, n-hex-2,4-enyl, n-hex-3,5-enyl, and n-hex-1,3,5-enyl. More preferred examples of a $C_{2-6}$ alkenyl group are ethenyl and prop-1-enyl.

Alkinyl is a straight chain or branched alkyl having 2, 3, 4, 5 or 6 carbon atoms and one to three triple bonds, preferably one or two triple bonds, most preferably one triple bond. Preferred examples of a $C_{2-6}$ alkinyl group are ethinyl, prop-1-inyl, prop-2-inyl, n-but-1-inyl, n-but-2-inyl, n-but-3-inyl, n-pent-1-inyl, n-pent-2-inyl, n-pent-3-inyl, n-pent-4-inyl, n-pent-1,3-inyl, isopent-1-inyl, neopent-1-inyl, n-hex-1-inyl, n-hex-2-inyl, n-hex-3-inyl, n-hex-4-inyl, n-hex-5-inyl, n-hex-1,3-inyl, n-hex-2,4-inyl, n-hex-3,5-inyl and n-hex-1,3,5-inyl. More preferred examples of a $C_{2-6}$ alkinyl group are ethinyl and prop-1-inyl.

Cycloalkyl is an alkyl ring having preferably 3, 4, 5, 6 or 7 carbon atoms at the most, such as cyclopropyl, cyclobutyl, cyclopentyl, cyclohexyl or cycloheptyl, more preferably 3, 4, 5 or 6 carbon atoms.

Heteroaryl is an aromatic moiety having 1, 2, 3, 4 or 5 carbon atoms and at least one heteratom selected from O, N and/or S and is preferably selected from thienyl, pyrrolyl, imidazolyl, pyrazolyl, pyridyl, pyrazinyl, pyrimidinyl, pyridazinyl, isothiazolyl, isoxazyl, furanyl, and indazolyl, more preferably from thienyl, furanyl, imidazlyl, pyridyl, and pyrimidinyl.

Heterocyclyl is a saturated or unsaturated ring containing at least one heteroatom selected from O, N and/or 5 and 1, 2, 3, 4, 5, 6 or 7 carbon atoms. Preferably, hetero-cyclyl is a 4 to 8-membered ring and is preferably selected from tetrahydrofuranyl, azetidinyl, pyrrolidinyl, piperidinyl, pyranyl, morpholinyl, thiomorpholinyl, more preferably from piperidinyl and pyrrolidinyl.

Halogen is a halogen atom selected from F, Cl, Br and I, preferably from F, Cl and Br.

The compounds of structural formula (I) are effective as melanocortin receptor modulators and are particularly effective as selective modulators of MC-4R. They are useful for the treatment and/or prevention of disorders responsive to the inactivation of MC-4R, such as cancer cachexia, muscle wasting, anorexia, amytrophic lateral sclerosis, anxiety, depression and other diseases with MC-4R involvement.

Optical Isomers—Diastereomers—Geometric Isomers—Tautomers

Compounds of structural formula (I) contain one or more asymmetric centers and can occur as racemates and racemic mixtures, single enantiomers, diastereomeric mixtures and individual diastereomers. The present invention is meant to comprehend all such isomeric forms of the compounds of structural formula (I).

Compounds of structural formula (I) may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula (I) may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, lithium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, parnoic, pantothenic, phosphoric, propionic, succinic, sulfuric, tartaric, p-toluenesulfonic, trifluoroacetic acid and the like. Particularly preferred are citric, fumaric, hydrobromic, hydrochloric, maleic, phosphoric, sulfuric and tartaric acids.

It will be understood that, as used herein, references to the compounds of formula (I) are meant to also include the pharmaceutically acceptable salts.

Utility

Compounds of formula (I) are melanocortin receptor antagonists and as such are useful in the treatment, control or prevention of diseases, disorders or conditions responsive to the inactivation of one or more of the melanocortin receptors including, but not limited to, MC-1R, MC-2R, MC-3R, MC-4R or MC-5R. Such diseases, disorders or conditions include, but are not limited to, cancer cachexia, muscle wasting, anorexia, amytrophic lateral sclerosis, anxiety and depression.

The compounds of formula (I) can be further used in the treatment, control or prevention of diseases, disorders or conditions which are responsive to the inactivation of one or more melanocortin receptors including, but not limited to, MC-1R, MC-2R, MC-3R, MC-4R or MC-5R. Such diseases, disorders or conditions include, but are not limited to, hypertension, hyperlipidemia, osteoarthritis, cancer, gall bladder disease, sleep apnea, compulsion, neuroses, insomnia/sleep disorder, substance abuse, pain, fever, inflammation, immune-modulation, rheumatoid arthritis, skin tanning, acne and other skin disorders, neuroprotective and cognitive and memory enhancement including the treatment of Alzheimer's disease.

Administration and Dose Ranges

Any suitable route of administration may be employed for providing a mammal, especially a human with an effective dosage of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably compounds of formula (I) are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating cancer cachexia, muscle wasting or anorexia generally satisfactory results are obtained when the compounds of the present invention are administered at a daily dosage of from about 0.001 milligram to about 100 milligrams per kilogram of body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

Formulation

The compounds of formula (I) are preferably formulated into a dosage form prior to administration. Accordingly the present invention also includes a pharmaceutical composition comprising a compound of formula (I) and a suitable pharmaceutical carrier.

The present pharmaceutical compositions are prepared by known procedures using well-known and readily available ingredients. In making the formulations of the present invention, the active ingredient (a compound of formula (I)) is usually mixed with a carrier, or diluted by a carrier, or enclosed within a carrier, which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

PREPARATION OF COMPOUNDS OF THE INVENTION

The compounds of formula (I) when existing as a diastereomeric mixture, may be separated into diastereomeric pairs of enantiomers by fractional crystallization from a suitable solvent such as methanol, ethyl acetate or a mixture thereof. The pair of enantiomers thus obtained may be separated into individual stereoisomers by conventional means by using an optically active acid as a resolving agent. Alternatively, any enantiomer of a compound of the formula (I) may be obtained by stereospecific synthesis using optically pure starting materials or reagents of known configuration.

The compounds of formula (I) of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously. The free amine bases corresponding to the isolated salts can be generated by neutralization with a suitable base, such as aqueous sodium hydrogencarbonate, sodium carbonate, sodium hydroxide and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation or crystallization. All temperatures are degrees Celsius.

In the schemes, preparations and examples below, various reagent symbols and abbreviations have the following meanings AcOH acetic acid
Ac$_2$O acetic anhydride
Boc tert-butoxycarbonyl
bp boiling point
CDI 1,1'-carbonyldiimidazole
DCE 1,2-dichloroethane
DCM dichloromethane
DIEA ethyl-diisopropylamine
DMF N,N-dimethylformamide
DMSO dimethylsulfoxide
EDC 1-(3-dimethylaminopropyl)-3-ethylcarbodiimide hydrochloride
Et$_2$O diethyl ether
EtOAc ethyl acetate
HATU O-(7-azabenzotriazol-1-yl)-N,N,N',N'-tetramethyluronium hexafluorophosphate
HOAt 1-hydroxy-7-azabenzotriazole
HOBt 1-hydroxybenzotriazole
h hour(s)
MeCN acetonitrile
MeLi methyllithium
MeOH methanol
Ms mesyl
NMM N-methylmorpholine
MW molecular weight
PG protecting group
RT room temperature
TEA triethylamine
TFAA trifluoroacetic acid anhydride
THF tetrahydrofurane
TMSI trimethylsilyl iodide
$t_R$ (min) HPLC retention time
Ts tosyl
Z benzyloxycarbonyl Reaction Scheme 1:
Synthesis of 2-sulfonylamino-pyridine-5-carboxylic acid amides

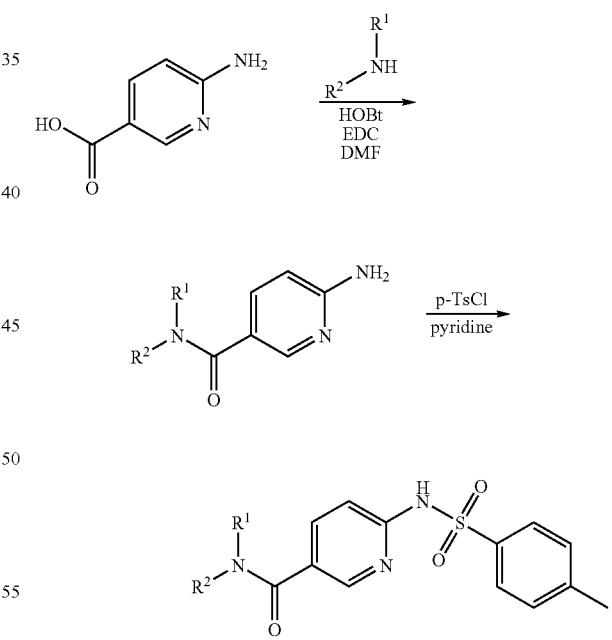

As shown in Reaction Scheme 1, optionally substituted amine and 2-amino-pyridine-5-carboxylic acid are reacted in an amide coupling reaction in the presence of a coupling reagent such as EDC in an organic solvent such as DMF or DCM at a suitable temperature. The resulting amide can then be reacted with a sulfonylchloride in a solvent such as pyridine or any other appropriate solvent and an organic base such as triethylamine to yield the corresponding sulfonylaminoamides.

Reaction Scheme 2:
Synthesis of 2-sulfonylamino-pyridine-5-carboxylic acid methyl ester

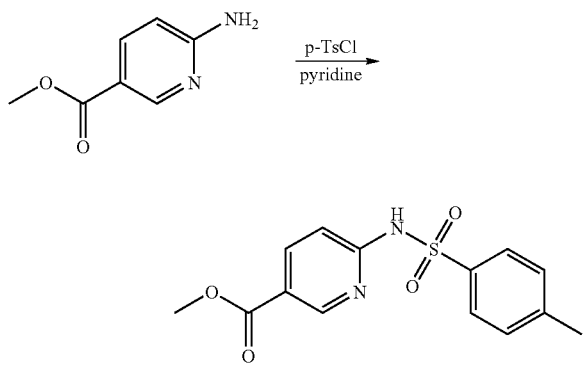

Alternatively, 2-amino-pyridine-5-carboxylic acid methyl ester can be reacted under the conditions described above to yield the corresponding sulfonylamino-esters, as shown in Reaction Scheme 2.

Reaction Scheme 3: Synthesis of imidazo[1,2-a]pyridines

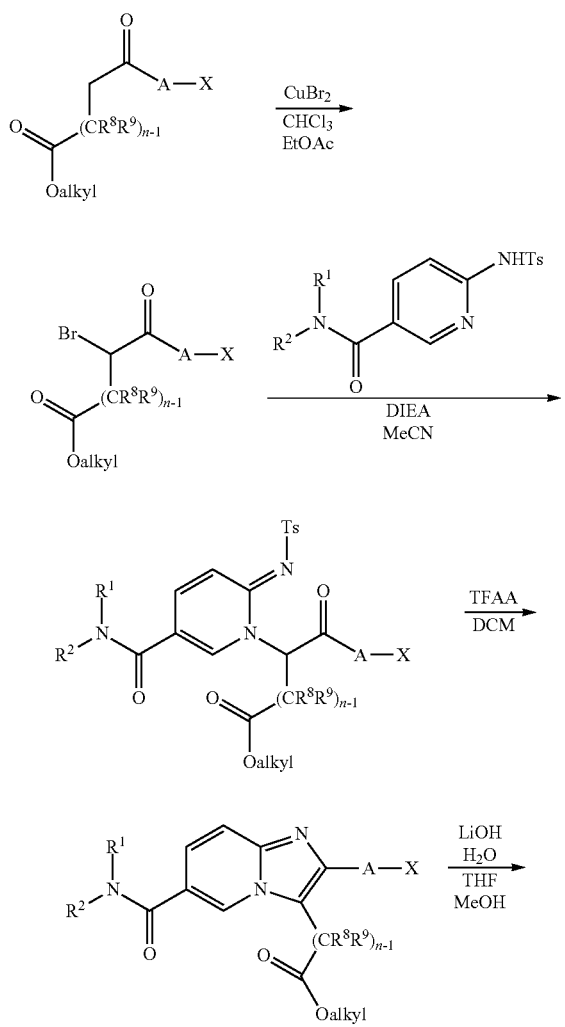

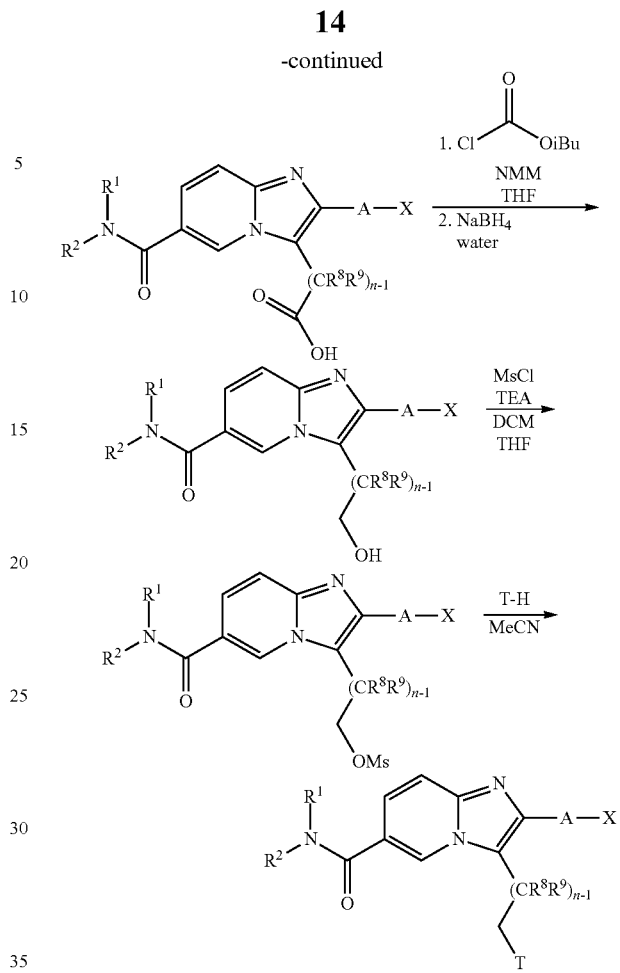

As shown in Reaction Scheme 3, optionally substituted ω-alkoxycarbonyl-α-bromoketones can be obtained from the corresponding ketone by reacting it for example with copper (II) bromide in a solvent such as mixture of ethyl acetate and chloroform at an appropriate temperature for a given time. The resulting α-bromoketones can then be reacted with sulfonylamino-amides in a solvent such as MeCN in the presence of an appropriate base, for example DIEA, to yield the N-alkylated sulfonylamino-amides. These intermediates can then be further cyclised to the corresponding imidazo[1,2-a] pyridines by treating them with TFAA in a suitable solvent such as DCM or 1,2-dichloroethane at an appropriate temperature for a given time. Ester function of optionally substituted imidazo[1,2-a]pyridines can be hydrolyzed under basic conditions using a reagent like lithium hydroxide monohydrate in a suitable solvent such as a mixture of water, THF and MeOH.

The resulting acid can be activated with a reagent such as isobutyl chloroformate or CDI in the presence of a suitable base such as N-methylmorpholine in an appropriate solvent such as THF and subsequently be reduced to the corresponding alcohol with a reducing agent such as sodium borohydride in an appropriate solvent such as a mixture of THF and water. The alcohol function can be converted to a leaving group with a reagent such as mesyl chloride or tosyl chloride in an appropriate solvent such as mixture of DCM and THF in the presence of a suitable base like TEA. Product of this reaction can be treated with an amine T-H in an appropriate solvent like MeCN to yield the target molecule.

Reaction Scheme 4:
Synthesis of imidazo[1,2-a]pyridines

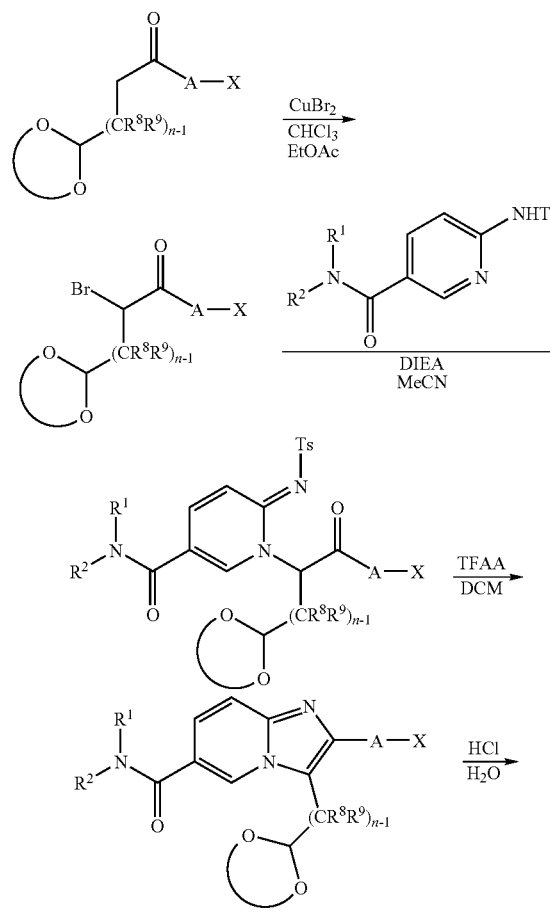

As shown in Reaction Scheme 4, methyl ester functions of optionally substituted imidazo[1,2-a]pyridines can be reduced to the corresponding alcohol with a reagent such as sodium borohydride in an appropriate solvent like methanol. The alcohol can be further reacted to the target molecules as depicted in Reaction Scheme 3.

Reaction Scheme 5:
Synthesis of imidazo[1,2-a]pyridines

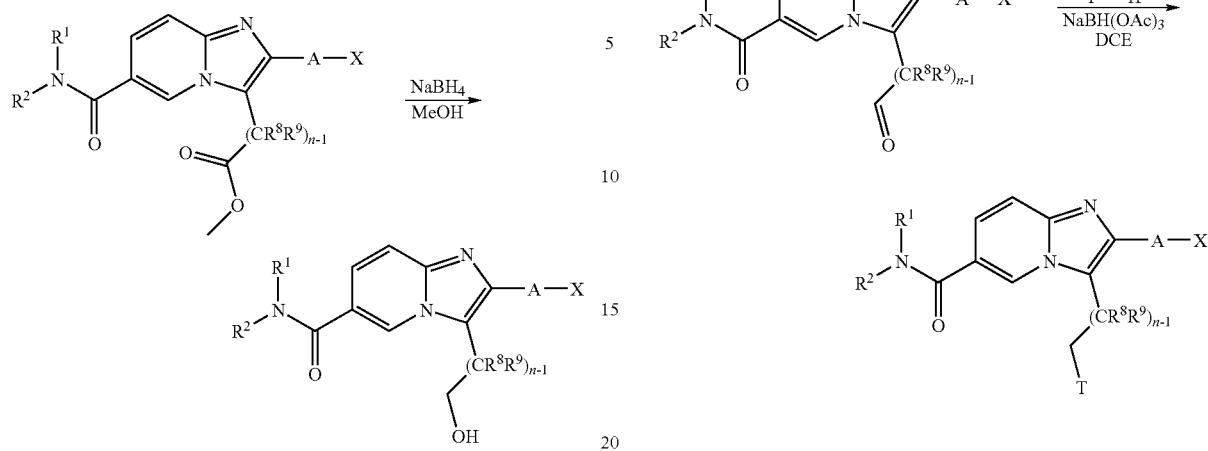

As shown in Reaction Scheme 5, optionally substituted α-bromoketones bearing a acetal function in ω-position can be obtained from the corresponding ketones and converted to the corresponding optionally substituted imidazo[1,2-a]pyridines as described above. The acetals can be cleaved to form the corresponding aldehydes by using a reagent such as 6N HCl in water. Optionally substituted aldehydes can be subjected to a reductive amination with an amine T-H in the presence of a reducing agent such as sodium triacetoxyborohydride in an appropriate solvent like DCE.

Reaction Scheme 6:
Synthesis of imidazo[1,2-a]pyridines

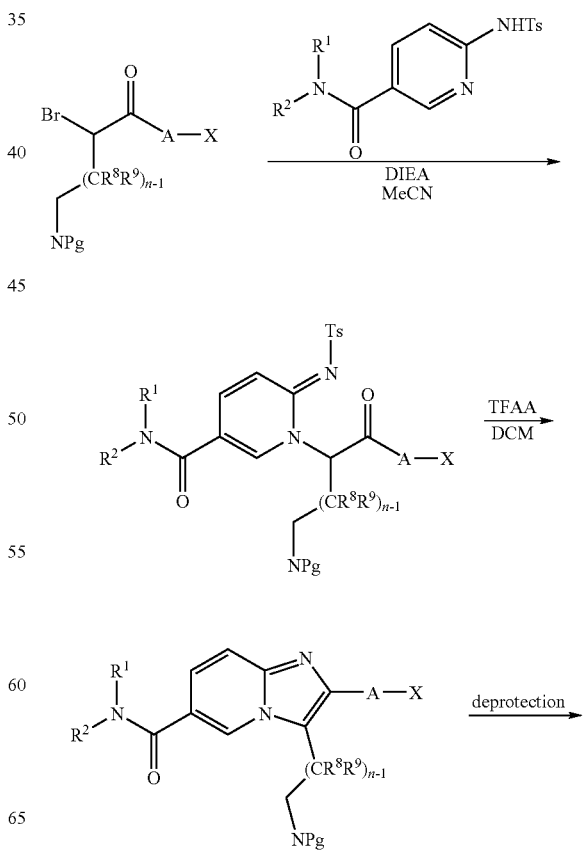

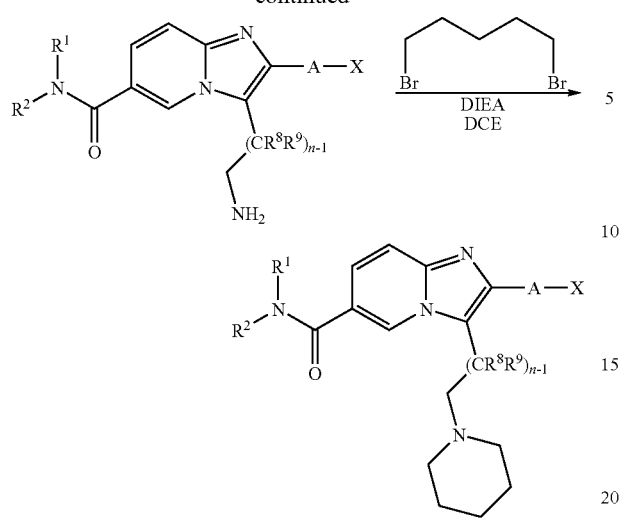

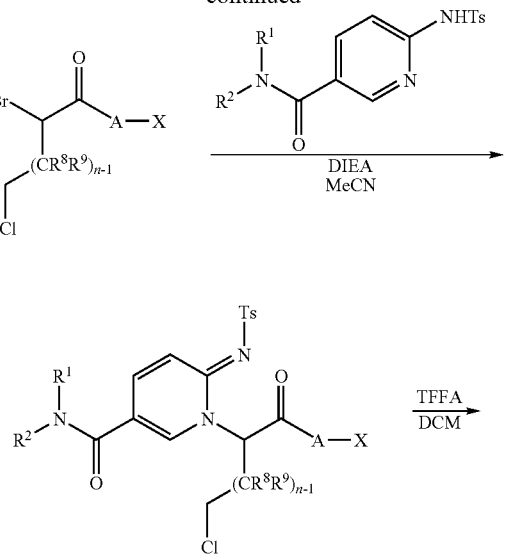

As shown in Reaction Scheme 6, optionally substituted N-protected ω-amino-α-bromoketones can be reacted with sulfonylamino-amides in a solvent such as MeCN in the presence of an appropriate base, for example DIEA, to yield the N-alkylated sulfonylamino-amides. These intermediates can then be further cyclised to the corresponding imidazo[1,2-a]pyridines by treating them with TFAA in a suitable solvent such as DCM or 1,2-dichloroethane at an appropriate temperature for a given time. The side chain amine function can be deprotected using a reagent such as TMSI in a suitable solvent such as MeCN in the case of a Z-protecting group. Phthalimids can be cleaved with hydrazine hydrate in an appropriate solvent like ethyl acetate. Optionally substituted imidazo[1,2-a]pyridines, bearing the primary amino group in the side chain can be directly tested in the biological assay or are subjected to further derivatization. For example, reaction with 1,5-dibromopentane in an appropriate solvent like 1,2-dichloroethane in the presence of a suitable base such as DIEA leads to the corresponding piperidine derivatives.

Reaction Scheme 7:
Synthesis of imidazo[1,2-a]pyridines

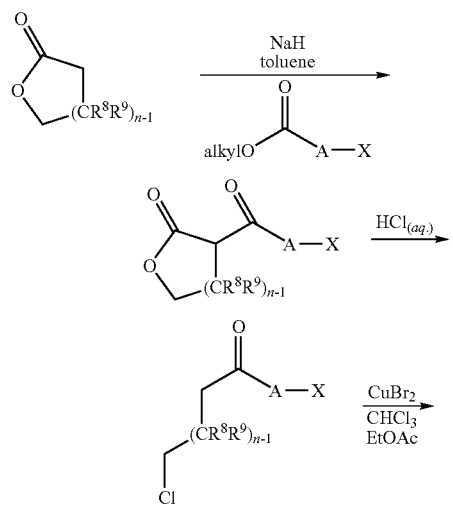

As shown in Reaction Scheme 7, optionally substituted lactones can be acylated with alkyl esters alkylOC(O)A-X in the presence of a suitable base such as sodium hydride in an appropriate solvent like toluene at elevated temperature. Said acylated lactones can be converted to ω-chloroketones by heating the lactones in concentrated hydrochloric acid. Reaction of optionally substituted ω-chloroketones with for example copper (II) bromide in a solvent such as mixture of ethyl acetate and chloroform at an appropriate temperature for a given time leads to the corresponding ω-chloro-α-bromoketones. The ω-chloro-α-bromoketones can then be reacted with sulfonylamino-amides in a solvent such as MeCN in the presence of an appropriate base, for example DIEA, to yield the N-alkylated sulfonylamino-amides. These intermediates can then be further cyclised to the corresponding imidazo[1,2-a]pyridines by treating them with TFAA in a suitable solvent such as DCM or 1,2-dichloroethane at an appropriate temperature for a given time. The capping group T can be inserted by reacting the chloroalkyl substituted imidazo[1,2-a]pyridines, with an capping group T-H in an appropriate solvent such as MeCN. When T-H is used in form of a hydrochloride, a suitable base such as DIEA is used in addition to liberate the free amine T-H.

Reaction Scheme 8:
Synthesis of imidazo[1,2-a]pyridines

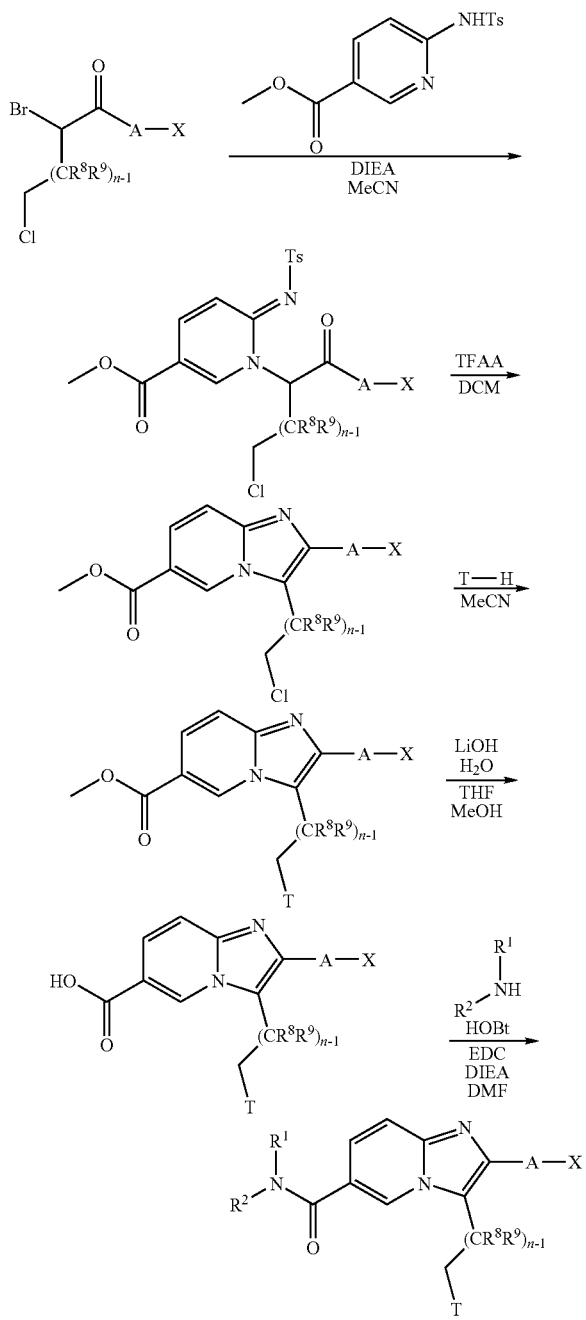

As shown in Reaction Scheme 8, optionally substituted ω-chloro-α-bromoketones can also be reacted with a sulfonylamino-ester in a solvent such as MeCN in the presence of an appropriate base, for example DIEA, to yield the N-alkylated sulfonylamino-esters. These intermediates can then be further cyclised to the corresponding imidazo[1,2-a]pyridines by treating them with TFAA in a suitable solvent such as DCM or 1,2-dichloroethane at an appropriate temperature for a given time. The capping group T can be inserted by reacting the chloroalkyl substituted imidazo[1,2-a]pyridines with a capping group T-H in an appropriate solvent such as MeCN. When T-H is used in form of a hydrochloride, a suitable base such as DIEA is used in addition to liberate the free amine T-H. Ester function of optionally substituted imidazo[1,2-a]pyridines can be hydrolyzed under basic conditions using a reagent like lithium hydroxide monohydrate in a suitable solvent such as a mixture of water, THF and MeOH. The product of the saponification can be isolated as lithium salt or as the corresponding acid. Alternatively, the ester function can also be cleaved under acidic conditions for example using a reagent such as aqueous hydrochloric acid. The product of the ester cleavage can be introduced into the next step as acid or lithium salt. Amide formation can be achieved using standard peptide coupling procedures. The acid can be coupled with an amine HNR$^1$R$^2$ in the presence of EDC/HOBt, EDC/HOAt, HATU, a base such as diisopropylethylamine and a solvent such as dichloromethane. A suitable solvent, such as DCM, DMF, THF or a mixture of the above solvents, can be used for the coupling procedure. A suitable base includes triethylamine (TEA), diisopropylethylamine (DIEA), N-methylmorpholine (NMM), collidine or 2,6-lutidine. A base may not be needed when EDC/HOBt is used.

Reaction Scheme 9:
Chloropyridine hydrolysis

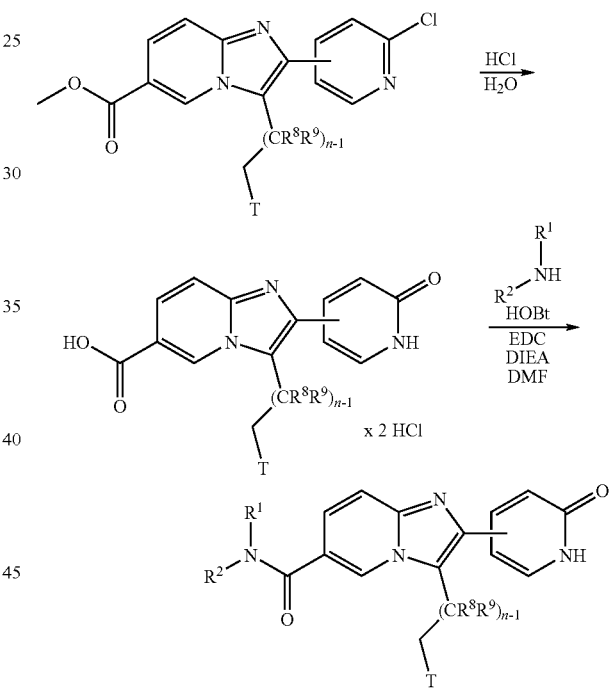

Optionally substituted imidazo[1,2-a]pyridines bearing a chloropyridine or bromopyridine as residue -A-X can be converted to the corresponding pyridones using a reagent such as aqueous hydrochloric acid at a suitable temperature as shown in Reaction Scheme 9. At the same time the ester function is also hydrolyzed. The acids can be coupled with amines HNR$^1$R$^2$ as described above.

Reaction Scheme 10:
Sythesis of α-bromoketones

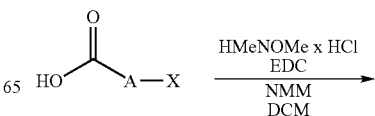

-continued

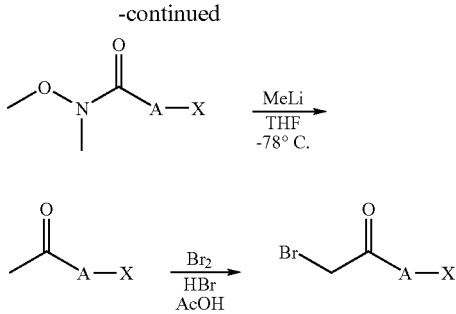

As shown in Reaction Scheme 10 optionally substituted bromoketones can be obtained in a three step reaction sequence starting from carboxylic acids. Said carboxylic acids can be converted to the corresponding Weinreb amides using N,O-dimethylhydroxylamine hydrochloride with a coupling reagent like EDC in the presence of a suitable base like NMM in an appropriate solvent such as DCM. The Weinreb amides can be converted to the corresponding methyl ketones using a reagent such as methyllithium in an inert solvent like THF at a suitable temperature. Bromination can be achieved using a mixture of bromine and hydrogen bromide in acetic acid.

Reaction Scheme 11:
Sythesis of imidazo[1,2-a]pyridines

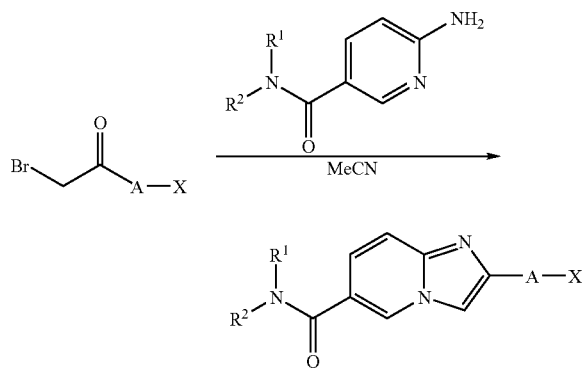

As shown in Reaction Scheme 11 optionally substituted aminopyridine-amides, which can be obtained as shown in Reaction Scheme 1, can be converted to imidazo[1,2-a]pyridine 6-carboxylic acid amides by reaction with α-bromoketones in a solvent like MeCN. This reaction can be carried out either in a flask in refluxing solvent or any other appropriate temperature or in a microwave reaction system. The reaction products can be purified by standard procedures or may precipitate directly from the solution upon cooling and may thus be used in subsequent reactions without further purification.

Reaction Scheme 12:
Mannich reaction

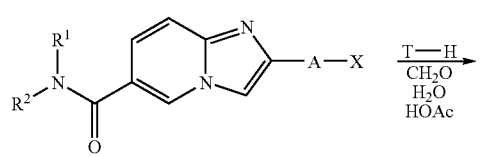

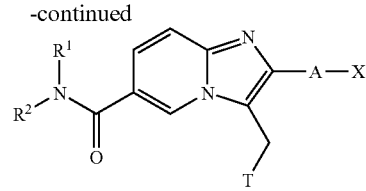

As shown in Reaction Scheme 12, products from Reaction Scheme 11 optionally substituted imidazo[1,2-a]pyridine acid amides may be used in a Mannich reaction to give 3-aminomethyl-imidazo[1,2-a]pyridine 6-carboxylic acid amides by reacting the imidazo[1,2-a]pyridine 6-carboxylic acid amides with an appropriate amine and aqueous formaldehyde solution in a solvent such as acetic acid. Diamines containing one nitrogen-protecting group can be further deprotected by treating the compound with an acid such as for example HCl in dioxane or TFA in DCM. Such compounds can then be purified by standard purification procedures such as flash chromatography or preparative HPLC.

Reaction Scheme 13:
Michael additions with α,β-unsaturated aldehydes

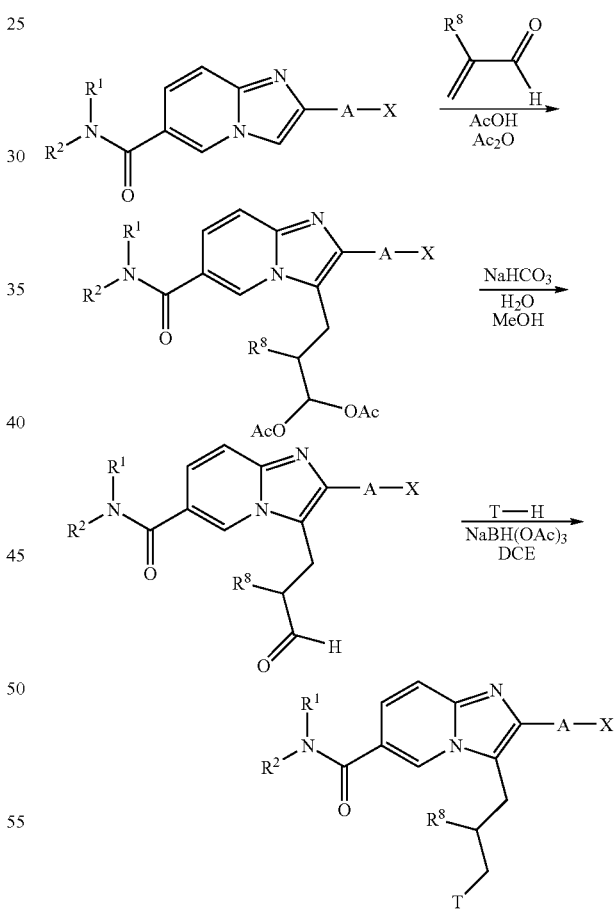

As depicted in Reaction Scheme 13, optionally substituted imidazo[1,2-a]pyridine 6-carboxylic acid amides can be reacted in a Michael addition reaction with α,β-unsaturated aldehydes in a solvent such as a mixture of acetic acid and acetic anhydride at elevated temperature. The reaction may also be carried out in a microwave reactor. The product of this reaction can be treated with a base such as sodium bicarbonate in a suitable solvent like a mixture of water and methanol to yield the corresponding aldehydes which can be subjected to a reductive amination with an amine T-H in the presence of a reducing agent such as sodium triacetoxyborohydride in an appropriate solvent like DCE. Alternatively, optionally substituted imidazo[1,2-a]pyridine 6-carboxylic acid esters can be used as starting materials. In this case the ester function can be converted to the amide after introduction of the side chain —CH₂CHR⁸CH₂T using the methods described in Reaction Scheme 8.

Reaction Scheme 14:
Michael additions with α,β-unsaturated ketones

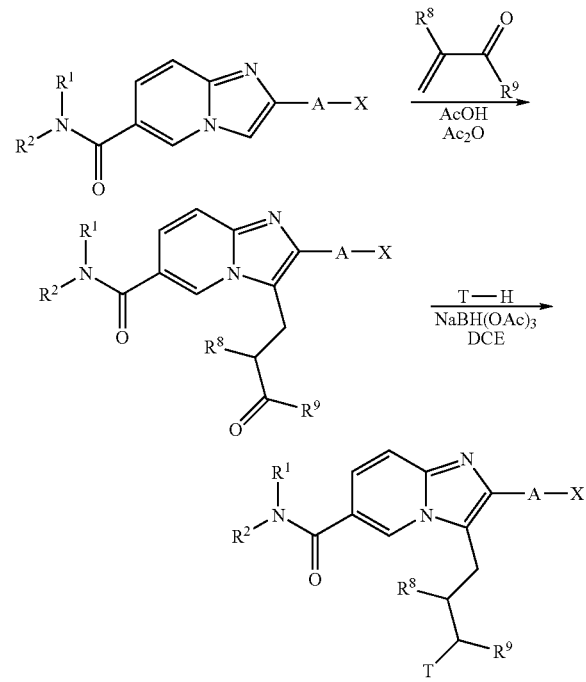

As shown in Reaction Scheme 14, Michael addition of optionally substituted imidazo[1,2-a]pyridine 6-carboxylic acid amides can also be performed with α,β-unsaturated ketones using the reaction conditions described in Reaction Scheme 13. In this case the product of the Michael addition reaction can be directly subjected to the reductive amination reaction.

Reaction Scheme 15:
Side chain alkylation

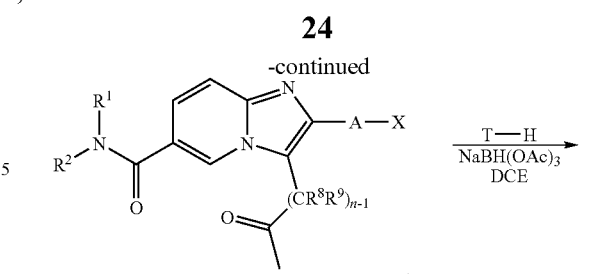
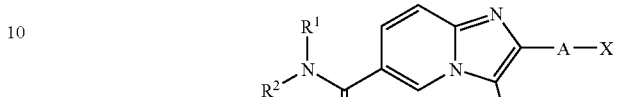
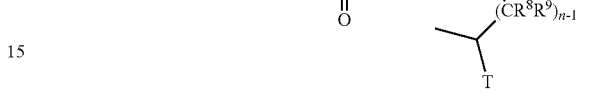

The products from Reaction Scheme 3, optionally substituted imidazo[1,2-a]pyridines bearing a carboxylate function in the side chain can be activated with a reagent such as CDI in an appropriate solvent like DCM and subsequently being reacted with N,O-dimethyl hydroxylamine hydrochloride in the presence of a suitable base such as DIEA. Reaction of the product with a reagent such as methyllithium in a suitable solvent such as THF or diethyl ether leads to the corresponding ketones which can be reductively aminated with an amine T-H in the presence of a reducing agent such as sodium triacetoxyborohydride in an appropriate solvent like DCE.

Reaction Scheme 16:
Chloropyridine reactions with amines

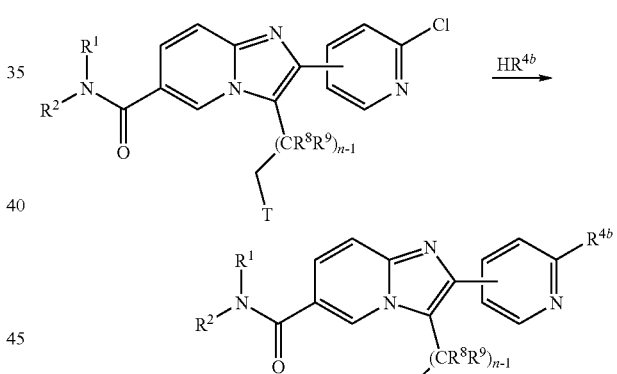
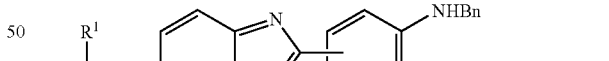
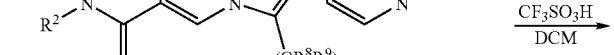
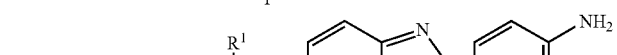
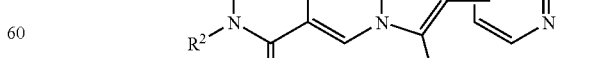

Optionally substituted imidazo[1,2-a]pyridines bearing a 2-chloropyridine substituent can be reacted with amines as shown in Reaction Scheme 16. The chloropyridines can be reacted with neat amines $HR^{4b}$ at elevated temperature to yield the corresponding 2-aminopyridines. The reaction may also be carried out in a microwave reactor. Benzyl protecting groups can be removed by treating N-benzylated 2-aminopyridines with a reagent such as trifluoromethanesulfonic acid in an inert solvent like DCM at an appropriate temperature.

Reaction Scheme 17:
Chloropyridine reactions with alcohols

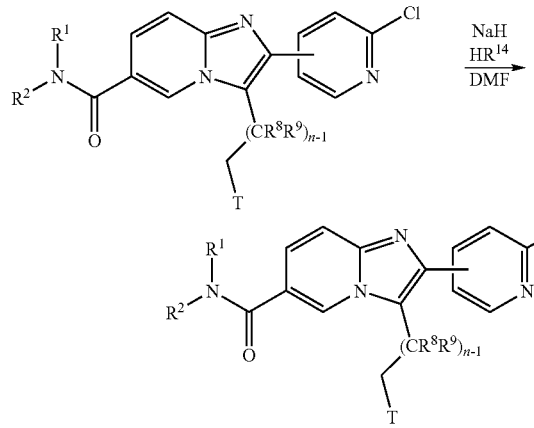

As shown in Reaction Scheme 17, optionally substituted imidazo[1,2-a]pyridines bearing a 2-chloropyridine substituent can be reacted with an alcoholate to form the corresponding alkoxypyridines. The alcoholate can be prepared from the corresponding alcohol $HR^{14}$ using a suitable base such as sodium hydride in an appropriate solvent like DMF. Reaction of the alcoholate with the chloropyridine can be achieved at elevated temperatures.

Reaction Scheme 18:
Pyridone alkylation

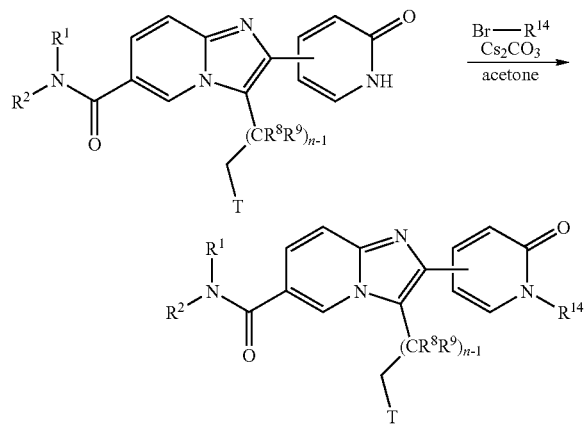

Optionally substituted imidazo[1,2-a]pyridines bearing a pyridone moiety can be N-alkylated as shown in Reaction Scheme 18. The pyridone nitrogen can be alkylated with an alkylbromide $Br-R^{14}$ in the presence of a base such as cesium carbonate or potassium carbonate in a suitable solvent like acetone at an appropriate temperature. Alcohol substituents on residue $R^{14}$ can be protected for example as esters. After the alkylation reaction the free alcohol can be obtained by hydrolyzing the ester with a reagent such as lithium hydroxide monohydrate in an appropriate solvent like a mixture of water and THF.

Analytical LC-MS

The compounds of the present invention according to formula (I) were analyzed by analytical LC-MS. The conditions are summarized below.

Analytical Conditions Summary:

LC10Advp-Pump (Shimadzu) with SPD-M10Avp (Shimadzu) UV/Vis diode array detector and QP2010 MS-detector (Shimadzu) in ESI+ modus with UV-detection at 214, 254 and 275 nm, Column: Waters XTerra MS C18, 3.5 μm, 2.1*100 mm, linear gradient with acetonitrile in water (0.15% HCOOH), exception: methods D and E (curve gradient)

Flow rate of 0.4 ml/min;

| Mobile Phase A: | water (0.15% HCOOH) |
| Mobile Phase B: | acetonitrile (0.15% HCOOH) |

Methods are:

A:
linear gradient from 5% to 95% acetonitrile in water (0.1% HCOOH)

| 0.00 min | 5% B |
| 5.00 min | 95% B |
| 5.10 min | 99% B |
| 6.40 min | 99% B |
| 6.50 min | 5% B |
| 8.00 min | Pump STOP |

B:
linear gradient from 10% to 90% acetonitrile in water (0.1% HCOOH)

| 0.00 min | 10% B |
| 5.00 min | 90% B |
| 5.10 min | 99% B |
| 6.40 min | 99% B |
| 6.50 min | 5% B |
| 8.00 min | Pump STOP |

C:
linear gradient from 5% to 95% acetonitrile in water (0.1% HCOOH)

| 0.00 min | 5% B |
| 10.00 min | 95% B |
| 10.10 min | 99% B |
| 11.40 min | 99% B |
| 11.50 min | 5% B |
| 13.00 min | Pump STOP |

D:
start concentration 1% acetonitrile

| 9.00 | B. Conc | 30 |
| 10.00 | B. Curve | 3 |
| 12.00 | B. Conc | 99 |

27 -continued

| | | |
|---|---|---|
| 15.00 | B. Conc | 99 |
| 15.20 | B. Conc | 1 |
| 18.00 | Pump STOP | |

E:

start concentration 10% acetonitrile

| | | |
|---|---|---|
| 10.00 | B. Conc | 60 |
| 11.00 | B. Curve | 2 |
| 12.00 | B. Conc | 99 |
| 15.00 | B. Conc | 99 |

28 -continued

| | | |
|---|---|---|
| 15.20 | B. Conc | 10 |
| 18.00 | Pump STOP | |

F:

start concentration 15% acetonitrile

| | | |
|---|---|---|
| 12.00 | B. Conc | 99 |
| 15.00 | B. Conc | 99 |
| 15.20 | B. Conc | 15 |
| 18.00 | STOP 0 | |

The following describes the detailed examples of the invention which can be prepared via the reaction schemes 1 to 18.

TABLE 1

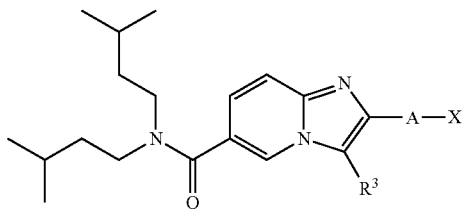

| | | | | HPLC | | MS MW (calc.) free base | [M + H]+ (found) |
|---|---|---|---|---|---|---|---|
| No. | salt | A-X | R³ | $t_R$ (min) | method | | |
| 1 | HCl | 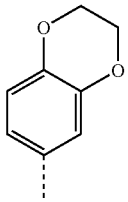 | 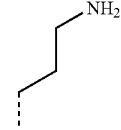 | 4.6 | E | 492.66 | 493 |
| 2 | HCl | 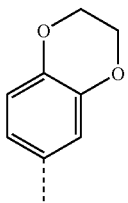 | 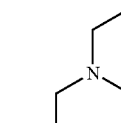 | 2.7 | A | 560.78 | 561 |
| 3 | HCl | 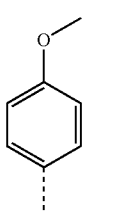 | 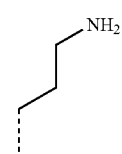 | 4.7 | E | 464.65 | 465 |

TABLE 1-continued
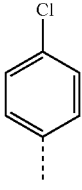
| No. | salt | A-X | R³ | HPLC t_R (min) | method | MS MW (calc.) free base | [M + H]⁺ (found) |
|---|---|---|---|---|---|---|---|
| 4 | HCl | 4-Cl-C₆H₄— | —(CH₂)₃NH₂ | 5.4 | E | 469.07 | 469 |
| 5 | HCl | 4-MeO-C₆H₄— | —(CH₂)₃N(CH₃)₂ | 3.9 | C | 492.70 | 493 |
| 6 | HCl | 4-MeO-C₆H₄— | —(CH₂)₃-pyrrolidinyl | 4.9 | E | 518.74 | 519 |
| 7 | HCOOH | 3-MeO-C₆H₄— | —(CH₂)₃NHCH(CH₃)₂ | 5.4 | E | 506.73 | 507 |
| 8 | HCOOH | 3-MeO-C₆H₄— | —(CH₂)₃N(C₂H₅)₂ | 5.6 | E | 520.76 | 521 |

TABLE 1-continued
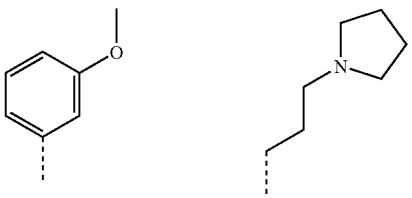
| No. | salt | A-X | R³ | HPLC t_R (min) | method | MW (calc.) free base | MS [M + H]⁺ (found) |
|---|---|---|---|---|---|---|---|
| 9 | HCOOH | 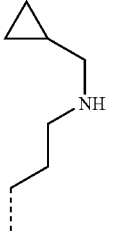 | 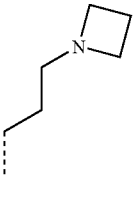 | 5.2 | E | 518.74 | 519 |
| 10 | HCOOH | | | 5.5 | E | 518.74 | 519 |
| 11 | HCOOH | | | 4.9 | E | 504.71 | 505 |
| 12 | HCOOH | 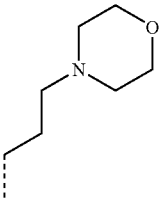 | | 5.1 | E | 534.74 | 535 |
| 13 | HCOOH | | 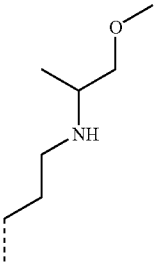 | 5.3 | E | 536.76 | 537 |

TABLE 1-continued

| No. | salt | A-X | R³ | HPLC t_R (min) | HPLC method | MS MW (calc.) free base | MS [M + H]⁺ (found) |
|---|---|---|---|---|---|---|---|
| 14 | HCOOH | 3-methoxyphenyl | (3S)-3-fluoro-1-butylpyrrolidine | 5.54 | E | 536.73 | 537 |
| 15 | HCOOH | 3-methoxyphenyl | 4-methyl-1-butylpiperazine | 5.0 | E | 547.78 | 548 |
| 16 | HCOOH | 3-methoxyphenyl | (3S)-3-methyl-4-butylmorpholine | 5.4 | E | 548.77 | 549 |
| 17 | HCl | 4-cyanophenyl | 1-butylpyrrolidine | 6.5 | E | 513.73 | 514 |
| 18 | HCl | 4-cyanophenyl | 3-(dimethylamino)propyl | 6.31 | E | 487.69 | 488 |

TABLE 1-continued
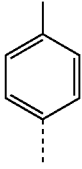
| No. | salt | A-X | R³ | HPLC t_R (min) | method | MS MW (calc.) free base | [M + H]⁺ (found) |
|---|---|---|---|---|---|---|---|
| 19 | HCOOH | 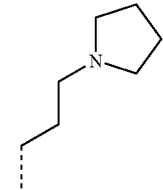 | 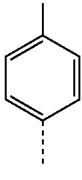 | 5.97 | E | 523.16 | 523 |
| 20 | HCOOH | 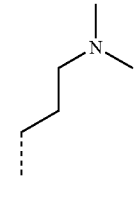 | 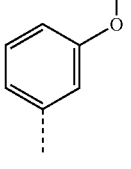 | 5.73 | E | 497.12 | 497 |
| 21 | HCl | 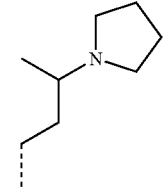 | 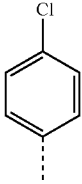 | 6.16 | E | 532.77 | 533 |
| 22 | HCOOH | 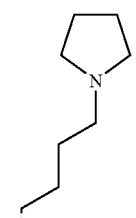 | 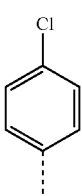 | 5.70 | E | 537.19 | 537 |
| 23 | HCOOH | 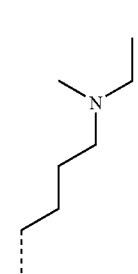 |  | 5.68 | E | 525.18 | 525 |

TABLE 1-continued

| | | | | HPLC | | MS | |
|---|---|---|---|---|---|---|---|
| | | | | | | MW (calc.) | |
| No. | salt | A-X | R³ | t_R (min) | method | free base | [M + H]⁺ (found) |
| 24 | HCOOH | 4-Cl-phenyl | -(CH₂)₄-N(CH₃)₂ | 5.47 | E | 511.16 | 511 |
| 25 | 2 × HCOOH | 4-(C(O)NH₂)-phenyl | -(CH₂)₃-pyrrolidin-1-yl | 5.54 | E | 531.74 | 532 |
| 26 | 2 × HCOOH | 4-CN-phenyl | -(CH₂)₂-pyrrolidin-1-yl | 6.43 | E | 499.70 | 500 |
| 27 | 2 × HCOOH | 4-CN-phenyl | -(CH₂)₂-(4-methylpiperazin-1-yl) | 5.69 | E | 528.74 | 529 |
| 28 | 2 × HCl | 3-OMe-phenyl | -(CH₂)₃-N(CH₃)₂ | 3.5 | F | 492.70 | 494 |

TABLE 1-continued

| No. | salt | A-X | R³ | HPLC t_R (min) | method | MS MW (calc.) free base | [M + H]⁺ (found) |
|---|---|---|---|---|---|---|---|
| 29 | 2 × HCl | 3-methoxyphenyl | (N-methyl-N-ethyl)aminopropyl | 3.6 | F | 506.73 | 507 |
| 30 | 2 × HCl | 3-methoxyphenyl | 3-(4-fluoropiperidin-1-yl)propyl | 3.9 | F | 550.76 | 551 |
| 31 | 2 × HCl | 3-methoxyphenyl | 3-(piperidin-1-yl)propyl | 3.8 | F | 532.77 | 534 |
| 32 | 2 × HCl | 3-methoxyphenyl | 3-((R)-3-fluoropyrrolidin-1-yl)propyl | 3.7 | F | 536.73 | 537 |
| 33 | 2 × HCl | 3-methoxyphenyl | 3-((S)-3-hydroxypyrrolidin-1-yl)propyl | 2.7 | A | 534.74 | 535 |

TABLE 1-continued

| No. | salt | A-X | R³ | HPLC t_R (min) | method | MS MW (calc.) free base | [M + H]⁺ (found) |
|---|---|---|---|---|---|---|---|
| 34 | 2 × HCl | 3-methoxyphenyl | (S)-3-hydroxypyrrolidin-1-yl-butyl | 2.7 | A | 534.74 | 535 |
| 35 | 2 × HCOOH | 4-(methylsulfonyl)phenyl | pyrrolidin-1-yl-butyl | 5.77 | E | 566.81 | 567 |
| 36 | 3 × HCl | 3-methoxyphenyl | piperazin-1-yl-butyl | 2.6 | A | 533.76 | 534 |
| 37 | 2 × HCl | 3-methoxyphenyl | 3-hydroxyazetidin-1-yl-butyl | 2.7 | A | 520.71 | 521 |
| 38 | 2 × HCl | 3-methoxyphenyl | N-methyl-N-propargylamino-butyl | 2.9 | A | 516.73 | 517 |

TABLE 1-continued

| No. | salt | A-X | R³ | HPLC t_R (min) | method | MS MW (calc.) free base | [M + H]⁺ (found) |
|---|---|---|---|---|---|---|---|
| 39 | HCOOH | benzo[1,3]dioxol-5-yl | pyrrolidin-1-ylpropyl | 4.89 | E | 532.73 | 533 |
| 40 | 2 × HCOOH | 4-methylpyridin-2-yl | pyrrolidin-1-ylpropyl | 6.24 | E | 503.73 | 504 |
| 41 | 2 × HCOOH | 6-methylpyridin-2-yl | pyrrolidin-1-ylpropyl | 5.42 | E | 503.73 | 504 |
| 42 | 2 × HCOOH | 5-chloropyridin-2-yl | pyrrolidin-1-ylpropyl | 6.45 | E | 524.15 | 525 |
| 43 | 2 × HCOOH | 3-oxo-3,4-dihydro-2H-benzo[1,4]oxazin-6-yl | pyrrolidin-1-ylpropyl | 4.90 | E | 559.75 | 560 |
| 44 | 2 × HCOOH | 4-hydroxypyridin-2-yl | pyrrolidin-1-ylpropyl | 4.99 | E | 505.70 | 506 |

TABLE 1-continued

| No. | salt | A-X | R³ | HPLC t_R (min) | method | MW (calc.) free base | MS [M + H]⁺ (found) |
|---|---|---|---|---|---|---|---|
| 45 | 2 × HCOOH | 3,4-dihydroquinolin-2(1H)-one-6-yl | 3-(pyrrolidin-1-yl)propyl | 4.68 | E | 557.78 | 558 |
| 46 | 2 × HCOOH | 4-hydroxy-2-pyridinyl | 3-(dimethylamino)propyl | 5.04 | E | 479.67 | 480 |
| 47 | HCl | oxazol-2-yl | 3-(pyrrolidin-1-yl)propyl | 5.7 | E | 479.67 | 480 |
| 48 | 2 × HCOOH | 2,4-dimethyloxazol-5-yl | 3-(pyrrolidin-1-yl)propyl | 6.2 | E | 507.72 | 508 |
| 49 | HCOOH | thiazol-2-yl | 3-(pyrrolidin-1-yl)propyl | 7.0 | E | 495.73 | 496 |

TABLE 1-continued

| No. | salt | A-X | R³ | HPLC t_R (min) | method | MS MW (calc.) free base | [M + H]⁺ (found) |
|---|---|---|---|---|---|---|---|
| 50 | 2 × HCOOH | 4-carboxyphenyl | 3-(pyrrolidin-1-yl)propyl | 5.67 | E | 532.73 | 533 |
| 51 | 2 × HCOOH | 6-(dimethylamino)pyridin-3-yl | 3-(dimethylamino)propyl | 4.2 | E | 506.73 | 507 |
| 52 | — | oxazol-2-yl | 3-(dimethylamino)propyl | 6.0 | E | 453.63 | 454 |
| 53 | HCOOH | oxazol-2-yl | 3-[N-methyl-N-(2-fluoroethyl)amino]propyl | 5.7 | E | 485.64 | 485 |
| 54 | 2 × HCOOH | 3-methoxyphenyl | 2-methyl-3-(pyrrolidin-1-yl)propyl | 5.60 | E | 532.77 | 533 |
| 55 | HCOOH | pyridin-2-yl | 3-(pyrrolidin-1-yl)propyl | 6.0 | E | 489.70 | 490 |

TABLE 1-continued

| No. | salt | A-X | R³ | HPLC t_R (min) | method | MS MW (calc.) free base | [M + H]⁺ (found) |
|---|---|---|---|---|---|---|---|
| 56 | HCOOH | 4-pyridyl | propyl-pyrrolidine | 4.6 | E | 489.70 | 490 |
| 57 | HCOOH | 5-methyl-2-pyridyl | propyl-pyrrolidine | 6.2 | E | 503.73 | 504 |
| 58 | HCOOH | 5-methyl-2-pyridyl | propyl-N,N-dimethylamine | 5.9 | E | 477.69 | 478 |
| 59 | — | 2-oxo-1H-pyridin-5-yl | propyl-pyrrolidine | 4.9 | E | 505.70 | 506 |
| 60 | 2 × HCl | 3-methoxyphenyl | propyl-N,N-diisopropylamine | 3.0 | A | 548.81 | 549 |
| 61 | 2 × HCOOH | thiazol-2-yl | propyl-N,N-dimethylamine | 5.6 | E | 469.69 | 470 |

TABLE 1-continued

| No. | salt | A-X | R³ | HPLC t_R (min) | method | MS MW (calc.) free base | [M + H]⁺ (found) |
|---|---|---|---|---|---|---|---|
| 62 | 2 × HCOOH | 2-oxo-1H-pyridin-6-yl | 3-(pyrrolidin-1-yl)propyl | 5.2 | E | 505.70 | 506 |
| 63 | — | 4-(N,N-dimethylcarbamoyl)phenyl | 3-(pyrrolidin-1-yl)propyl | 4.82 | E | 559.79 | 560 |
| 64 | — | 4-(N-methylcarbamoyl)phenyl | 3-(pyrrolidin-1-yl)propyl | 4.79 | E | 545.77 | 546 |
| 65 | — | 6-amino-pyridin-3-yl | 3-(pyrrolidin-1-yl)propyl | 4.46 | E | 504.72 | 505 |
| 66 | HCOOH | 6-chloro-pyridin-3-yl | 3-(dimethylamino)propyl | 6.2 | E | 498.11 | 498 |

TABLE 1-continued
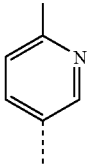
| No. | salt | A-X | R³ | HPLC t_R (min) | method | MS MW (calc.) free base | [M + H]⁺ (found) |
|---|---|---|---|---|---|---|---|
| 67 | — | 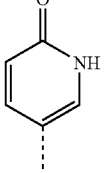 | 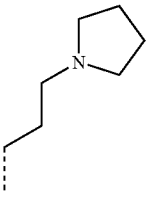 | 3.2 | A | 524.15 | 524 |
| 68 | 2 × HCOOH | 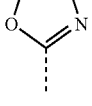 | 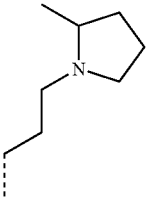 | 4.5 | E | 479.67 | 480 |
| 69 | — | 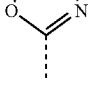 | 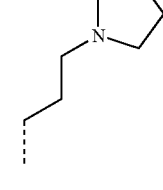 | 6.1 | E | 493.69 | 494 |
| 70 | HCOOH | 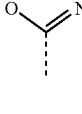 | 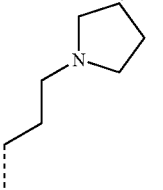 | 5.8 | E | 509.69 | 510 |
| 71 | HCOOH | | | 5.6 | E | 495.66 | 496 |

TABLE 1-continued
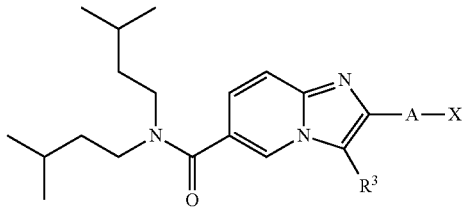
| No. | salt | A-X | R³ | HPLC t_R (min) | method | MS MW (calc.) free base | [M + H]⁺ (found) |
|---|---|---|---|---|---|---|---|
| 72 | HCOOH | oxazol-2-yl | 3-fluoropyrrolidin-1-yl-butyl | 6.2 | E | 497.66 | 498 |
| 73 | HCOOH | oxazol-2-yl | 3-hydroxyazetidin-1-yl-butyl | 5.9 | E | 481.64 | 482 |
| 74 | HCOOH | oxazol-2-yl | azetidin-1-yl-butyl | 6.0 | E | 465.64 | 466 |
| 75 | HCOOH | oxazol-2-yl | N-methyl-N-isopropyl-aminobutyl | 6.5 | E | 481.68 | 482 |
| 76 | HCOOH | oxazol-2-yl | 2-(hydroxymethyl)pyrrolidin-1-yl-butyl | 5.4 | E | 509.69 | 510 |

TABLE 1-continued

| No. | salt | A-X | R³ | HPLC t_R (min) | method | MS MW (calc.) free base | [M + H]+ (found) |
|---|---|---|---|---|---|---|---|
| 77 | HCOOH | oxazol-2-yl | 1-(4-hydroxypiperidin-1-yl)butyl | 5.4 | E | 509.69 | 510 |
| 78 | HCOOH | oxazol-2-yl | (3S)-3-fluoropyrrolidin-1-yl butyl | 6.0 | E | 497.66 | 499 |
| 79 | — | 5-(2-hydroxyethoxy)pyridin-2-yl | pyrrolidin-1-yl butyl | 4.9 | E | 549.76 | 550 |
| 80 | 2 × HCOOH | oxazol-2-yl | (3R)-3-hydroxypyrrolidin-1-yl butyl | 5.7 | E | 495.66 | 496 |
| 81 | — | 1-(2-hydroxyethyl)-2-oxo-1,2-dihydropyridin-5-yl | pyrrolidin-1-yl butyl | 4.6 | E | 549.76 | 550 |

TABLE 1-continued
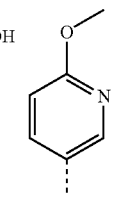
| No. | salt | A-X | R³ | HPLC t_R (min) | method | MS MW (calc.) free base | [M + H]⁺ (found) |
|---|---|---|---|---|---|---|---|
| 82 | 2 × HCOOH | 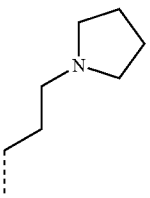 | 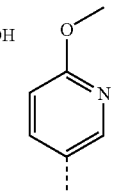 | 5.0 | E | 519.73 | 520 |
| 83 | 2 × HCOOH | 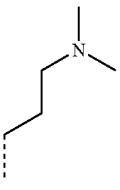 | 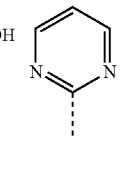 | 5.1 | E | 493.69 | 494 |
| 84 | 2 × HCOOH | 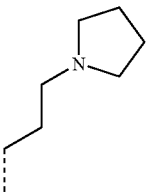 | 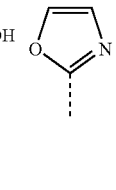 | 5.12 | E | 490.69 | 491 |
| 85 | 2 × HCOOH | 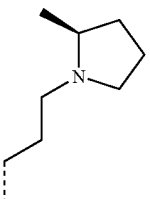 | 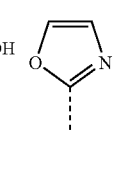 | 6.4 | E | 493.69 | 494 |
| 86 | 2 × HCOOH | 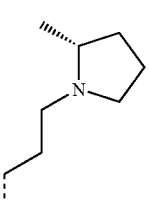 | 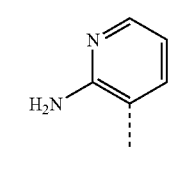 | 6.6 | E | 493.69 | 494 |
| 87 | — | 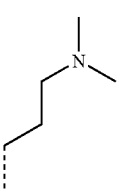 | | 4.30 | E | 478.68 | 479 |

TABLE 1-continued

| No. | salt | A-X | R³ | HPLC t_R (min) | method | MS MW (calc.) free base | [M + H]+ (found) |
|---|---|---|---|---|---|---|---|
| 88 | 2 × HCOOH | pyridin-2(1H)-one-4-yl | 4-(dimethylamino)butyl | 5.1 | E | 479.67 | 480 |
| 89 | 2 × HCOOH | pyridin-2(1H)-one-4-yl | 4-(pyrrolidin-1-yl)butyl | 5.3 | E | 505.70 | 506 |
| 90 | 2 × HCOOH | 2-aminopyridin-3-yl | 4-(pyrrolidin-1-yl)butyl | 4.74 | E | 504.72 | 505 |
| 91 | — | 1-(3-hydroxypropyl)pyridin-2(1H)-one-5-yl | 4-(pyrrolidin-1-yl)butyl | 4.7 | E | 563.78 | 564 |
| 92 | — | 2-(3-hydroxypropoxy)pyridin-5-yl | 4-(pyrrolidin-1-yl)butyl | 5.4 | E | 563.78 | 564 |
| 93 | HCOOH | 1-(2-hydroxypropyl)pyridin-2(1H)-one-5-yl | 4-(pyrrolidin-1-yl)butyl | 5.0 | E | 563.78 | 564 |

TABLE 1-continued

| No. | salt | A-X | R³ | HPLC $t_R$ (min) | method | MS MW (calc.) free base | [M + H]⁺ (found) |
|---|---|---|---|---|---|---|---|
| 94 | HCOOH | pyridine-O-CH₂-CH(OH)-CH₃ | pyrrolidine-propyl | 5.7 | E | 563.78 | 564 |
| 95 | — | pyridone-N-CH₂CH₂-OCH₃ | pyrrolidine-propyl | 5.1 | E | 563.78 | 564 |
| 96 | — | pyridine-O-CH₂CH₂-OCH₃ | pyrrolidine-propyl | 5.8 | E | 563.78 | 564 |
| 97 | — | pyridine-O-CH₂CH₂-OC(O)CH₃ | pyrrolidine-propyl | 6.0 | E | 591.79 | 592 |
| 98 | 2 × HCOOH | tetrahydropyran-4-yl | pyrrolidine-propyl | 3.8 | E | 496.74 | 497 |

TABLE 1-continued

| No. | salt | A-X | R³ | HPLC t_R (min) | method | MW (calc.) free base | MS [M + H]⁺ (found) |
|---|---|---|---|---|---|---|---|
| 99 | — | (2-oxopyridin-1-yl with ethyl acetate substituent) | pyrrolidinylpropyl | 3.4 | E | 591.79 | 592 |
| 100 | — | 2-oxo-1H-pyridinyl | 2-methylpyrrolidinylpropyl | 4.3 | E | 519.73 | 520 |
| 101 | — | (2-oxopyridin-1-yl with ethyl acetate substituent) | 2-methylpyrrolidinylpropyl | 3.7 | E | 605.82 | 606 |
| 102 | — | (pyridin-2-yloxy ethyl acetate) | 2-methylpyrrolidinylpropyl | 4.3 | E | 605.82 | 606 |
| 103 | — | (2-oxopyridin-1-yl with hydroxyethyl substituent) | 2-methylpyrrolidinylpropyl | 3.2 | E | 563.78 | 564 |

TABLE 1-continued

| No. | salt | A-X | R³ | HPLC t_R (min) | method | MS MW (calc.) free base | [M + H]⁺ (found) |
|---|---|---|---|---|---|---|---|
| 104 | — | (2-hydroxyethoxy-pyridinyl) | (2-methylpyrrolidinyl-propyl) | 3.7 | E | 563.78 | 564 |

TABLE 2

| No. | salt | A-X | R³ | HPLC t_R (min) | method | MS MW (calc.) free base | [M + H]⁺ (found) |
|---|---|---|---|---|---|---|---|
| 105 | — | (2-oxopyridinyl-ethyl acetate) | (pyrrolidinyl-propyl) | 2.8 | E | 587.76 | 588 |
| 106 | — | (pyridinyloxy-ethyl acetate) | (pyrrolidinyl-propyl) | 3.5 | E | 587.76 | 588 |

TABLE 2-continued

| No. | salt | A-X | R³ | HPLC t_R (min) | method | MS MW (calc.) free base | [M + H]⁺ (found) |
|---|---|---|---|---|---|---|---|
| 107 | — | pyridinone-N-CH₂CH₂OH | pyrrolidine-propyl | 3.7 | E | 545.72 | 546 |
| 108 | | 2-(2-hydroxyethoxy)pyridine | pyrrolidine-propyl | 4.3 | E | 545.72 | 546 |
| 109 | — | pyridinone-NH | 2-methylpyrrolidine-propyl | 3.5 | E | 515.70 | 516 |
| 110 | — | pyridinone-N-CH₂CH₂OAc | 2-methylpyrrolidine-propyl | 3.0 | E | 601.79 | 602 |
| 111 | — | pyridinone-N-CH₂CH₂OH | 2-methylpyrrolidine-propyl | 3.8 | E | 559.75 | 560 |

TABLE 2-continued
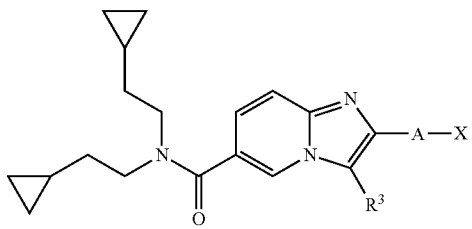
| No. | salt A-X | A-X | R[3] | HPLC t_R (min) | method | MS MW (calc.) free base | [M + H]+ (found) |
|---|---|---|---|---|---|---|---|
| 112 | — | pyridinyl-O-CH2CH2OH | 2-methylpyrrolidin-1-yl-propyl | 4.4 | E | 559.75 | 560 |
TABLE 3
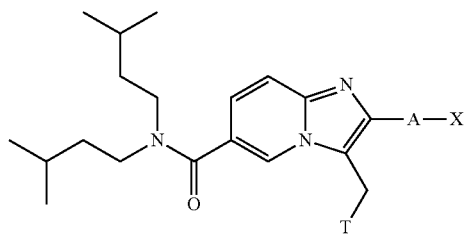
| No. | salt | A-X | T | HPLC t_R (min) | method | MS MW (calc.) free base | [M + H]+ (found) |
|---|---|---|---|---|---|---|---|
| 113 | HCl | 4-cyanophenyl | 1-methylpiperidin-4-yl(methyl)amino | 5.4 | D | 542.77 | 543 |
| 114 | HCOOH | 3-methoxyphenyl | 1-methylpiperidin-4-yl(methyl)amino | 8.7 | E | 547.78 | 548 |

TABLE 3-continued
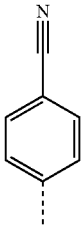
| No. | salt | A-X | T | HPLC $t_R$ (min) | method | MW (calc.) free base | MS [M + H]⁺ (found) |
|---|---|---|---|---|---|---|---|
| 115 | HCl | 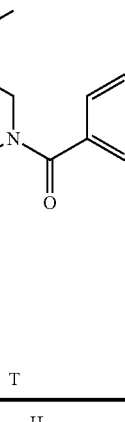 | 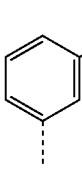 | 2.9 | B | 514.71 | 515 |
| 116 | HCl | 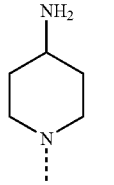 | 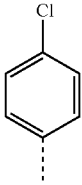 | 2.3 | B | 519.73 | 521 |
| 117 | HCOOH | 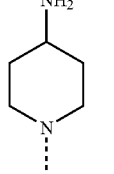 | 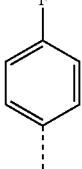 | 5.1 | E | 524.16 | 525 |
| 118 | HCl | 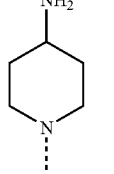 | 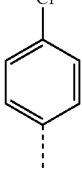 | 2.4 | B | 507.70 | 508 |
| 119 | HCl | 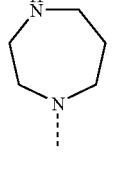 | 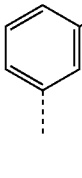 | | | 524.16 | |
| 120 | HCl | 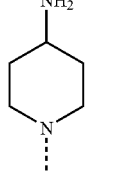 | | 2.5 | B | 524.16 | 524 |

TABLE 3-continued
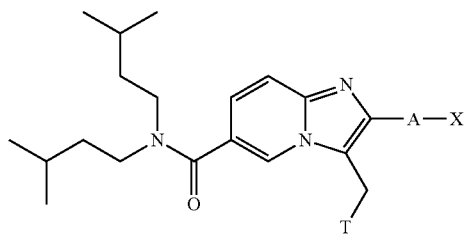
| No. | salt | A-X | T | HPLC $t_R$ (min) | method | MW (calc.) free base | MS [M + H]+ (found) |
|---|---|---|---|---|---|---|---|
| 121 | HCl | 3-methoxyphenyl | piperazin-1-yl (NH) | 2.4 | B | 505.71 | 507 |
| 122 | HCOOH | 3-cyanophenyl | 4-aminopiperidin-1-yl | 8.9 | D | 514.72 | 515 |
| 123 | HCl | 3-methoxyphenyl | 3-aminopyrrolidin-1-yl | 2.5 | B | 505.71 | 507 |
| 124 | HCl | 5-(pyridin-2-yl)thiophen-2-yl | 4-aminopiperidin-1-yl | 2.5 | B | 572.82 | 573 |
| 125 | HCl | thiophen-2-yl | 4-aminopiperidin-1-yl | 2.4 | B | 495.74 | 496 |
| 126 | HCl | 4-chlorophenyl | 3-aminopiperidin-1-yl | 6.3 | E | 524.16 | 524 |

TABLE 3-continued

| No. | salt | A-X | T | HPLC $t_R$ (min) | method | MS MW (calc.) free base | [M + H]$^+$ (found) |
|---|---|---|---|---|---|---|---|
| 127 | HCl | 4-Cl-phenyl | cis-octahydropyrrolo[3,4-c]pyrrole | 6.1 | A | 536.17 | 536 |
| 128 | HCOOH | 4-Cl-phenyl | octahydropyrrolo[1,2-a]pyrazine | 9.7 | D | 550.19 | 550 |
| 129 | HCOOH | 2,4-dimethoxyphenyl | 1-methyl-4-(methylamino)piperidine | 4.6 | E | 577.82 | 578 |
| 130 | HCOOH | 2,5-dimethoxyphenyl | 1-methyl-4-(methylamino)piperidine | 4.8 | E | 577.82 | 578 |
| 131 | HCOOH | 3,4-dichlorophenyl | 1-methyl-4-(methylamino)piperidine | 6.7 | E | 586.65 | 586 |
| 132 | HCl | 3,4-dichlorophenyl | 4-aminopiperidine | 2.7 | B | 558.60 | 559 |

TABLE 3-continued
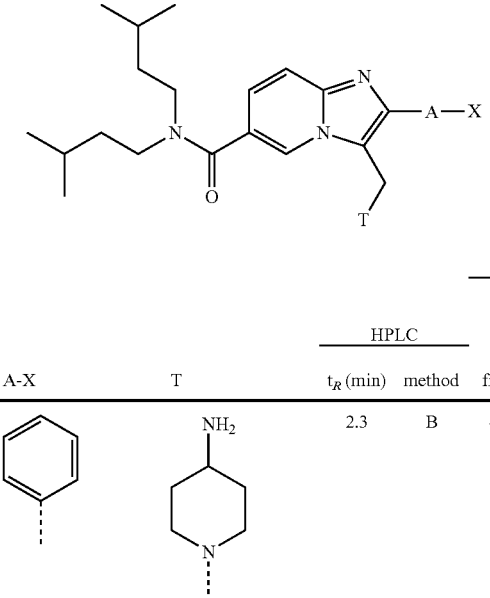
| No. | salt | A-X | T | HPLC $t_R$ (min) | method | MW (calc.) free base | MS [M + H]⁺ (found) |
|---|---|---|---|---|---|---|---|
| 133 | HCl |  | 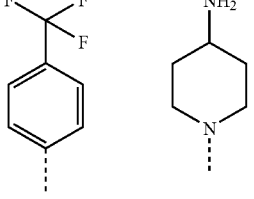 | 2.3 | B | 489.71 | 490 |
| 134 | HCl | 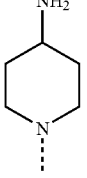 | 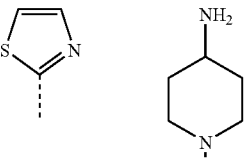 | 2.7 | B | 557.71 | 558 |
| 135 | HCl | 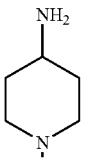 | 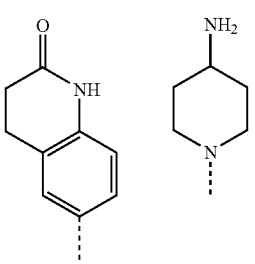 | 2.3 | B | 496.72 | 497 |
| 136 | HCl | 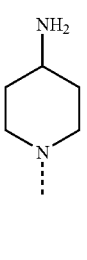 | | 2.2 | B | 558.77 | 560 |

TABLE 3-continued

| No. | salt | A-X | T | HPLC $t_R$ (min) | method | MW (calc.) free base | MS [M + H]⁺ (found) |
|---|---|---|---|---|---|---|---|
| 137 | HCl | 3-oxo-3,4-dihydro-2H-benzo[1,4]oxazin-6-yl | 4-aminopiperidin-1-yl | 2.2 | B | 560.75 | 561 |
| 138 | HCl | 4-cyanophenyl | 4-aminopiperidin-1-yl | 5.0 | E | 514.72 | 515 |
| 139 | HCl | 3,4-dimethoxyphenyl | 4-aminopiperidin-1-yl | 2.3 | B | 549.76 | 550 |
| 140 | HCl | 4-methoxyphenyl | 4-aminopiperidin-1-yl | 2.4 | B | 519.74 | 520 |

TABLE 4

|     |         |                |                 | HPLC       |        | MS MW (calc.) | [M + H]+ |
|-----|---------|----------------|-----------------|------------|--------|---------------|----------|
| No. | salt    | R¹             | R²              | t_R (min)  | method | free base     | (found)  |
| 141 | 2 × HCOOH | cyclopropylmethyl | propyl       | 3.77       | E      | 469.63        | 470      |
| 142 | 2 × HCl | butyl          | butyl           | 3.6        | F      | 485.67        | 486      |
| 143 | HCOOH   | sec-butyl      | cyclopropylethyl | 5.62      | E      | 511.71        | 512      |
| 144 | HCOOH   | isobutyl       | isobutyl        | 5.30       | E      | 485.67        | 486      |
| 145 | 2 × HCl | cyclopropylethyl | cyclopropylethyl | 3.6      | F      | 509.69        | 510      |

TABLE 5
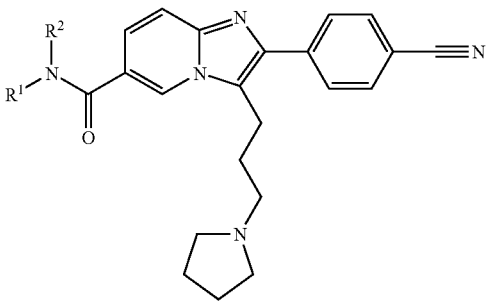
| No. | salt | NR¹R² | HPLC $t_R$ (min) | method | MW (calc.) free base | MS [M + H]⁺ (found) |
|---|---|---|---|---|---|---|
| 146 | HCOOH | | 8.35 | D | 483.66 | 485 |
| 147 | — | | 2.7 | F | 469.63 | 470 |
TABLE 6
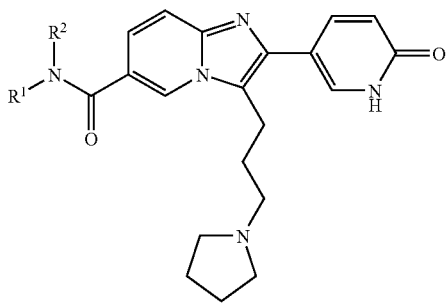
| No. | salt | R¹ | R² | HPLC $t_R$ (min) | method | MW (calc.) free base | MS [M + H]⁺ (found) |
|---|---|---|---|---|---|---|---|
| 148 | 2 × HCOOH | | | 6.1 | E | 501.67 | 502 |

TABLE 6-continued

| No. | salt | R¹ | R² | HPLC t_R (min) | method | MW (calc.) free base | MS [M + H]⁺ (found) |
|---|---|---|---|---|---|---|---|
| 149 | — | (isopentyl) | (2-hydroxymethyl-butyl) | 2.8 | E | 521.70 | 522 |

TABLE 7

| No. | salt | R¹ | R² | HPLC t_R (min) | method | MW (calc.) free base | MS [M + H]⁺ (found) |
|---|---|---|---|---|---|---|---|
| 150 | HCl | (isopentyl) | (isobutyl) | 4.8 | E | 500.69 | 501 |

The following examples are provided to illustrate the invention and are not limiting the scope of the invention in any manner.

SYNTHESIS OF EXAMPLE 9

Intermediate 9a

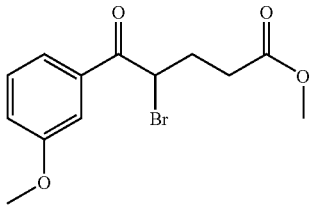

A suspension of CuBr$_2$ (1071 mg) in EtOAc (10 ml) was heated to reflux and a solution of 5-(3-methoxy-phenyl)-5-oxo-pentanoic acid methyl ester (913 mg) in CHCl$_3$ was added. The reaction mixture was refluxed over night. An additional amount of CuBr$_2$ (300 mg) was added in one portion and the mixture was allowed to reflux for another 4 h. The reaction mixture was filtered over Celite to remove copper salts and the solvent was removed in vacuo to dryness. The residue was purified by flash-chromatography (EtOAc/cyclohexane) to yield the title compound.

Intermediate 9b

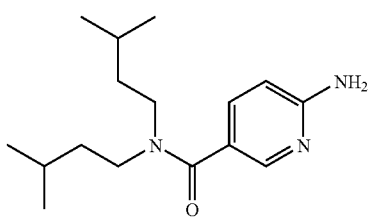

To a solution of 6-amino-nicotinic acid (3 g) in DMF/DCM (80/20) was added diisoamylamine (4.1 g), EDC (5 g), HOBt (3.52 g) and DIEA (4.54 ml). The reaction mixture was stirred at 50° C. over night. The solution was evaporated in vacuo to dryness. The residue was redissolved in a small amount of DMF then buffer (pH 7) was added. The resulting precipitate was collected, washed with water and dried to yield the title compound.

Intermediate 9c

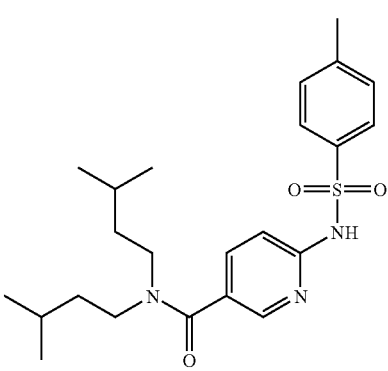

To a solution of intermediate 9b) (1 g) in pyridine (25 ml) was added p-toluenesulfonylchloride (756 mg) in one portion. The reaction mixture was heated at 85° C. for 16 h. The solution was evaporated in vacuo to dryness and H$_2$O was added to the residue. The resulting slurry was stirred for 30 min, then filtered and washed with toluene. The remaining solid was collected and dried to yield the title compound as a yellow solid.

Intermediate 9d)

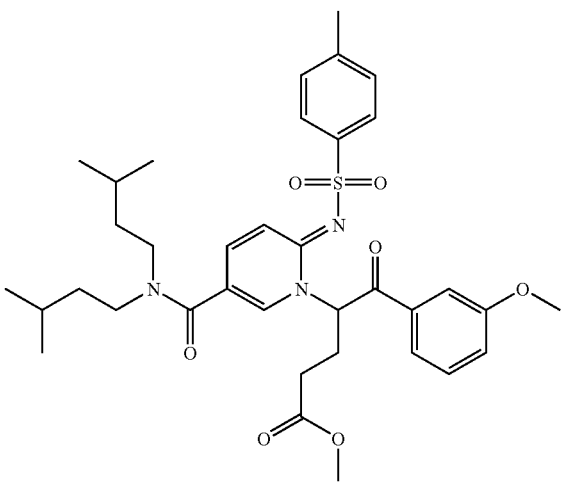

To a warm solution of intermediate 9c) (1781 mg) and DIEA (1.198 ml) in MeCN (50 ml) was added intermediate 9a) (1084 mg). The reaction mixture was heated at 100° C. for 4 h. The solution was evaporated in vacuo to dryness and the residue was purified by flash-chromatography (EtOAc/cyclohexane) to yield the title compound.

Intermediate 9e

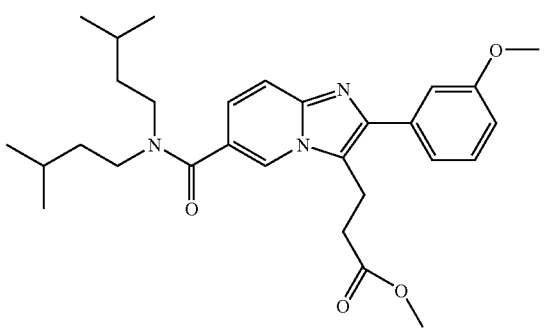

Intermediate 9d) (1.372 g) was dissolved in DCM (50 ml) and the reaction was purged with argon. To this solution TFAA (2 ml) was added and the reaction was allowed to stir for 16 h. The solution was evaporated in vacuo to dryness and the residue was purified by flash-chromatography (DCM/MeOH) to yield the title compound as a colorless foam.

Intermediate 9f

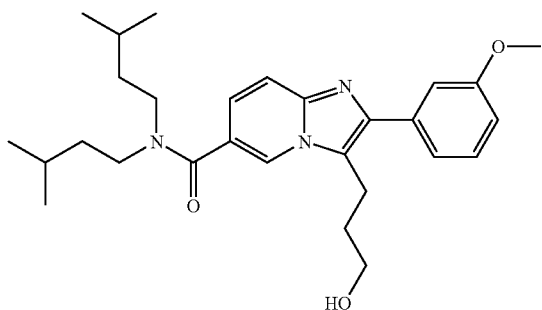

Intermediate 9e) (568 mg) was dissolved in THF (40 ml) and methanol (4 ml) was added. The solution was heated to reflux and subsequently sodium borohydride (87 mg) was added. Further sodium borohydride was added in several portions and refluxing continued. The reaction was stopped with acetone and the solvent removed in vacuo. The residue was purified by flash chromatography (DCM/MeOH 98:2) to yield the title compound.

Intermediate 9g

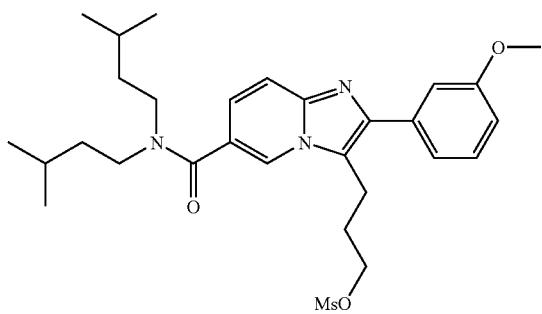

A solution of intermediate 9f) in dry DCM (10 ml) was purged with argon and cooled to 0° C. TEA (170 μl) and mesylchloride (95 μl) were added to this solution and the reaction mixture was allowed to warm up. Stirring was continued for 3 h. The reaction mixture was washed with H$_2$O and saturated NaHCO$_3$ solution. The organic layer was dried over Na$_2$SO$_4$ and evaporated in vacuo to dryness to yield the title compound, which was used in the next step without further purification.

EXAMPLE 9

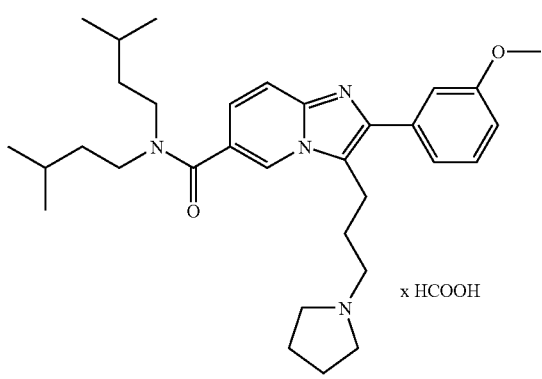

To a solution of pyrrolidine (168 mg) in dry MeCN (5 ml) was added a solution of intermediate 9 g) (86 mg) in dry MeCN. The reaction was heated to 75° C. for 14 h. The solution was evaporated in vacuo to dryness and the residue was purified by preparative HPLC to yield the title compound as a colorless solid.

SYNTHESIS OF EXAMPLE 17

Intermediate 17a

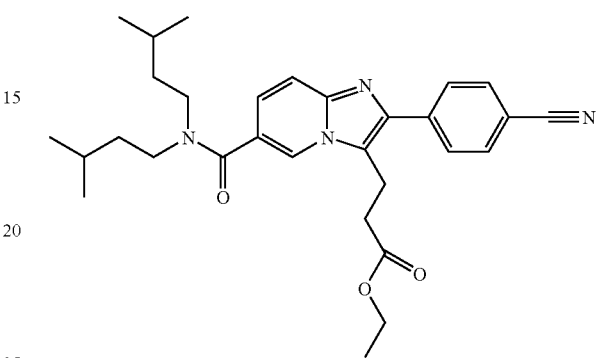

The synthesis was performed as described for intermediate 9e).

Intermediate 17b

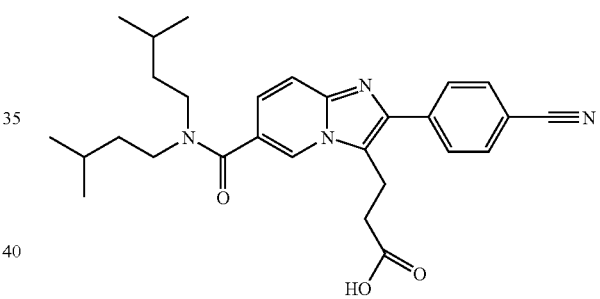

To a solution of intermediate 17a) (370 mg) in THF (15 ml) was added a 2M solution of lithium hydroxide in water (0.74 ml) at 0° C. Subsequently the ice bath was removed and the reaction allowed to stir at ambient temperature for 2 days. The mixture was diluted with ethyl acetate and brine and the pH adjusted to pH 6 with a solution of 3% citric acid. After separation of the layers, the organic layer was washed with brine and dried over sodium sulfate. The solvent was removed under reduced pressure to yield the title compound that was used in the next step without further purification.

Intermediate 17c

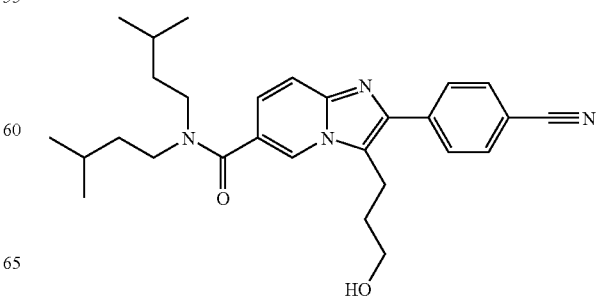

Intermediate 17b) (315 mg) was dissolved in THF (20 ml) and carbonyldiimidazole (162 mg) was added. The mixture was stirred at ambient temperature for 1 h before cooled to 0° C. Sodium borohydride (38 mg) in water was added and stirring continued for another 10 min. The reaction was quenched with acetone and the solvent removed in vacuo. The residue was taken up in ethyl acetate and water. After separation of the layers, the organic layer was washed with a solution of 5% citric acid, saturated sodium bicarbonate solution and brine. After drying over sodium sulfate the solvent was removed in vacuo and the residue purified by flash chromatography (DCM/MeOH) to yield the title compound.

Intermediate 17d

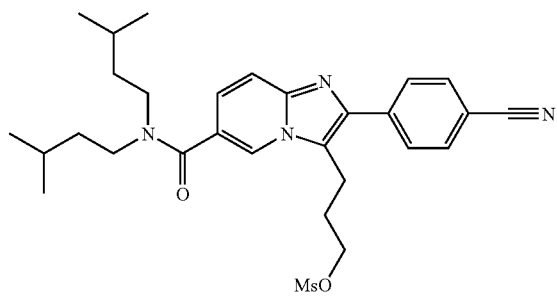

Intermediate 17c) (100 mg) was dissolved in dichloromethane (10 ml) and at 0° C. mesylchloride (0.026 ml) and triethylamine (0.046 ml) were added. The ice bath was removed and the mixture stirred at ambient temperature before additional mesylchloride (0.007 ml) and triethylamine (0.012 ml) were added and stirring continued for another hour. The mixture was diluted with dichloromethane and washed with water/saturated sodium bicarbonate and water. The organic layer was dried over sodium sulfate and the solvent removed in vacuo to yield the title compound that was used in the next step without further purification.

EXAMPLE 17

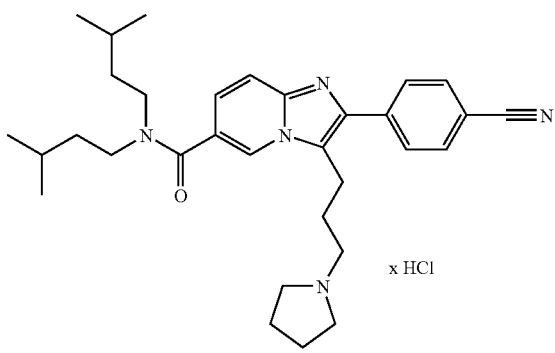

To a solution of pyrrolidine (78 mg) in dry MeCN (1.5 ml) was added a solution of intermediate 17d) (55 mg) in dry acetonitrile. The reaction was heated to 50° C. overnight. The mixture was evaporated in vacuo to dryness and the residue was purified by flash chromatography (DCM/MeOH) to yield the title compound. The free base was transformed into the corresponding HCl salt.

SYNTHESIS OF EXAMPLE 21

Intermediate 21a

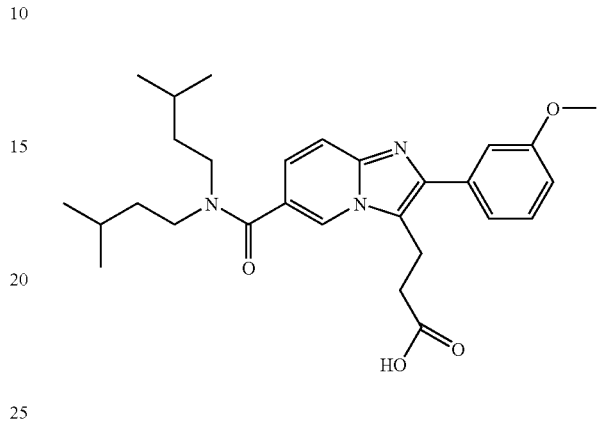

To a solution of intermediate 9e) (300 mg) in THF (12 ml) was added a 2M solution of lithium hydroxide in water (0.61 ml) at 0° C. Subsequently the ice bath was removed and the reaction allowed to stir at ambient temperature overnight. The mixture was diluted with ethyl acetate and brine and the pH adjusted to pH 6 with a solution of 3% citric acid. After separation of the layers, the organic layer was washed with brine and dried over sodium sulfate. The solvent was removed under reduced pressure to yield the title compound that was used in the next step without further purification.

Intermediate 21b

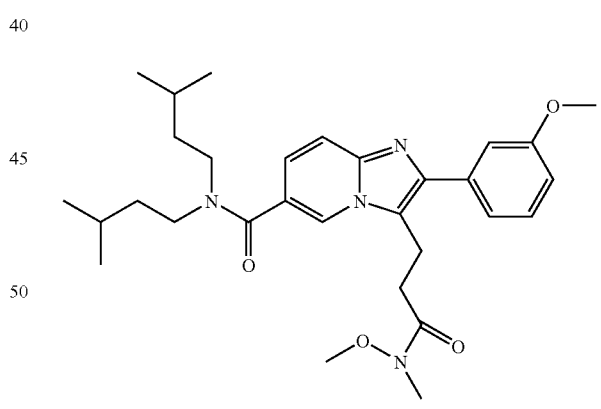

Intermediate 21a) (275 mg) was dissolved in dichloromethane and carbonyldiimidazole (102 mg) was added. The mixture was stirred at ambient temperature for 30 min before N,O-dimethylhydroxylamine hydrochloride (62 mg) and diisopropylethylamine (0.110 ml) were added subsequently. Stirring was continued overnight. The mixture was diluted with dichloromethane and the organic phase washed with a solution of 5% citric acid, sodium bicarbonate solution and brine before drying over sodium sulfate and removing the solvent in vacuo. Purification by flash chromatography (DCM/MeOH) yielded the title compound.

Intermediate 21c

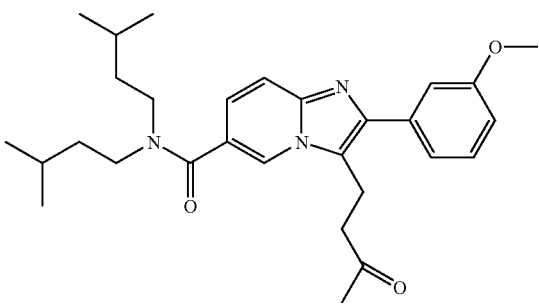

To a solution of intermediate 21b) (100 mg) in dry tetrahydrofurane was added a solution of methyllithium (1.5 M in diethylether, 0.12 ml) at −78° C. The mixture was stirred for 30 min before hydrolyzing with saturated ammonium chloride solution. After dilution with diethylether, the layers were separated and the aqueous layer extracted twice with diethylether. Combined organic layers were washed with brine, dried over sodium sulfate and the solvent removed in vacuo. Purification by flash chromatography led to the title compound.

EXAMPLE 21

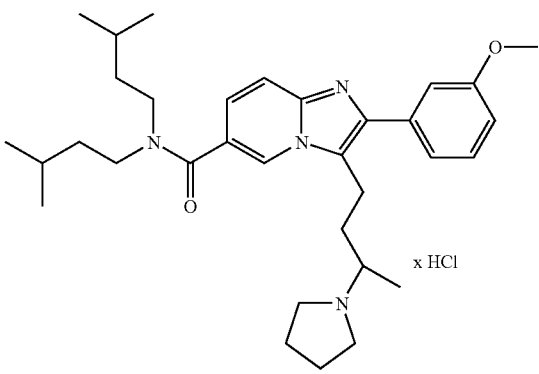

Intermediate 21c) (65 mg) and pyrrolidine (0.013 ml) were dissolved in dichloroethane (2 ml) and subsequently glacial acetic acid (0.008 ml) and sodium triacetoxyborohydride (42 mg) were added. The mixture was stirred at ambient temperature for 3 days. The solvent was removed under reduced pressure and the residue purified by flash chromatography (DCM/MeOH) to yield the title compound. The free base was transformed into the HCl salt.

SYNTHESIS OF EXAMPLE 25

EXAMPLE 25

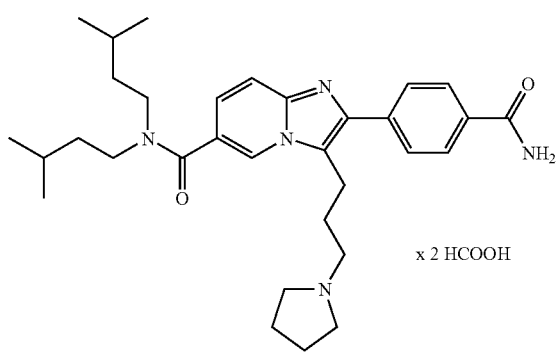

To a solution of Example 17 (407 mg) in tert. butyl alcohol (8 ml) fine powder of potassium hydroxide (240 mg) was added and the mixture heated to 70° C. for 4 hours. Then the mixture was partitioned between brine and ethyl acetate. The aqueous phase was extracted three times with ethyl acetate. The combined organic layers were dried over sodium sulfate. The solvent was removed under reduced pressure to yield the title compound which was purified by preparative HPLC.

SYNTHESIS OF EXAMPLE 27

Intermediate 27a

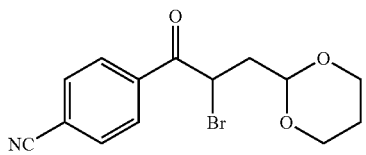

Copper bromide (547 mg) was suspended in ethyl acetate (13 ml) and heated to reflux. Then 4'-cyano-3-(1,3-dioxan-2-yl) propiophenone (500 mg) in chloroform (13 ml) was added. The reaction mixture was refluxed for 2 h. Another 340 mg of copper bromide were added in two portions followed by 2 hours of refluxing. The mixture was stirred overnight at room temperature and subsequently filtered through Celite. The solvents were evaporated under reduced pressure and the product purified by chromatography.

Intermediate 27b

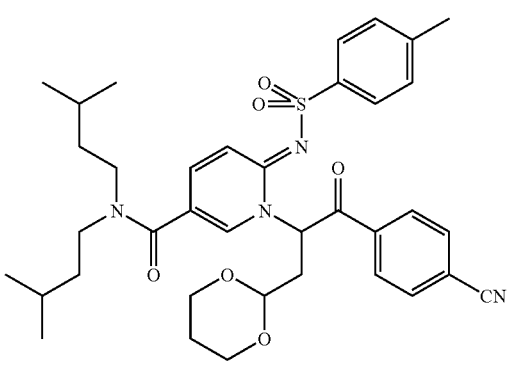

A mixture of tosylate intermediate 9c) (700 mg) and diisopropylethylamine (0.52 ml) in acetonitrile (20 ml) was heated to 50° C. Intermediate 27a) (480 mg) in acetonitrile was then added and the reaction mixture stirred at 50° C. for 30 min and at room temperature overnight. The solvent was removed under reduced pressure. The mixture was purified by flash chromatography to yield the title compound.

Intermediate 27c

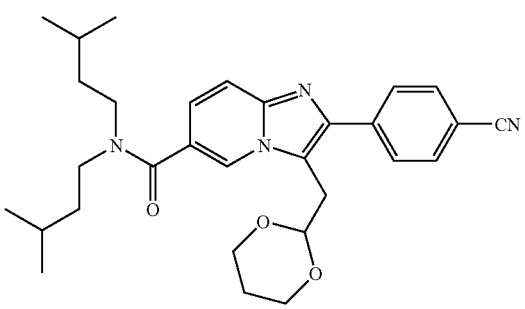

Intermediate 27b) (620 mg) was dissolved in dry dichloromethane (16 ml). The mixture was cooled to 0° C. with an ice bath. Then trifluoroacetic anhydride (1.62 ml) was added. The mixture was stirred at 0° C. for 30 minutes and then at room temperature for 2 hours.

The solvent was removed under reduced pressure. The product intermediate 27c) was used without purification for the next step.

Intermediate 27d

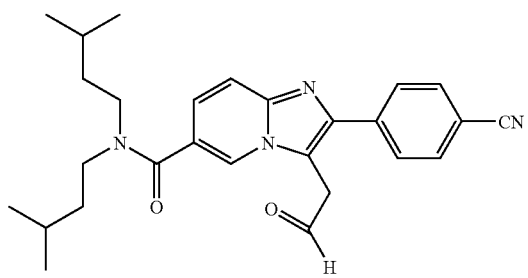

Intermediate 27c) (460 mg) was dissolved in tetrahydrofurane (16 ml) and the solution cooled to 0° C. 6M HCl (0.46 ml) was added and the reaction mixture then stirred at 60° C. overnight. Another 3 equivalents of HCl 6N were added and the mixture continued to stir at 60° C. The mixture was neutralized with sodium carbonate and the product was extracted with ethyl acetate. The organic phase was dried over sodium sulfate. The solvent was removed under reduced pressure and the mixture purified by flash chromatography to yield the title compound.

EXAMPLE 27

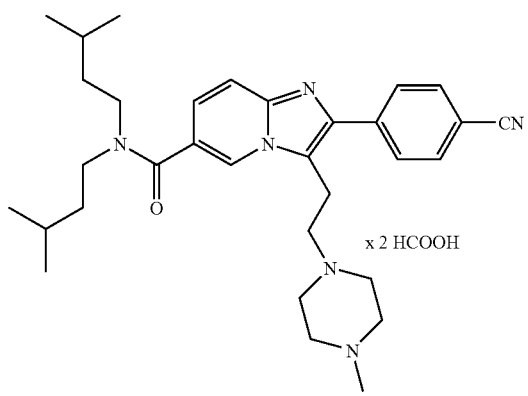

Intermediate 27d) (19 mg) was dissolved in dichloroethane (0.3 ml), 1-methylpiperazine (5 µl) was added and the reaction mixture stirred for 30 min. After addition of sodium triacetoxyborohydride (12 mg) the mixture was stirred at room temperature overnight. Water was added and the aqueous phase was extracted twice with dichloromethane. The combined organic layers were dried over sodium sulfate and the solvent was removed under reduced pressure. The title compound was purified by preparative HPLC.

SYNTHESIS OF EXAMPLE 47

Intermediate 47a

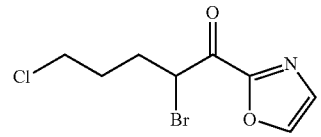

Under argon, to a stirring suspension of copper(II) bromide (9.523 g) in ethyl acetate (100 ml) was added 2-(5-chlorovaleryl)oxazole (4.000 g) in chloroform (100 ml). The resulting mixture was stirred at reflux temperature overnight. The reaction mixture was filtered through Celite and the filtrate was evaporated to dryness. The crude product was purified by column chromatography.

Intermediate 47b

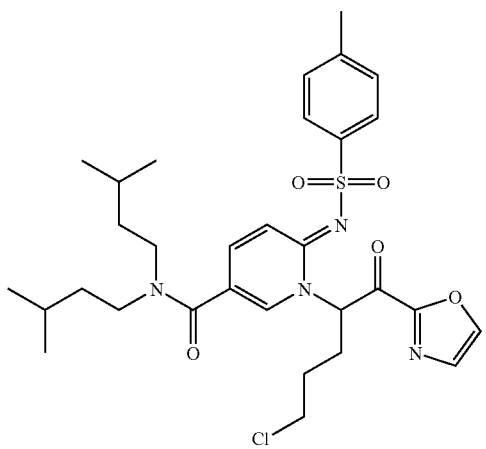

At 50° C. to a stirring solution of intermediate 47a) (2665 mg) in acetonitrile (75 ml) was added DIEA (3658 µl). The obtained solution was stirred for 15 minutes then intermediate 9c) (4532 mg) in acetonitrile (75 ml) was added. The obtained solution was stirred at 50° C. for 3 h. Volatiles were removed and the product was purified by column chromatography.

Intermediate 47c

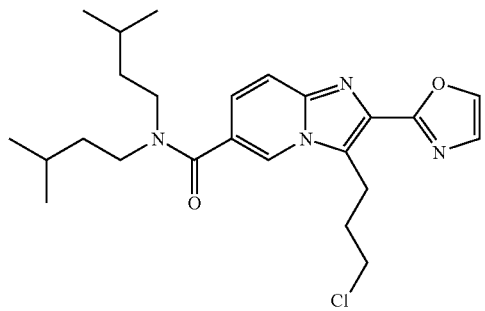

At 0° C., to a stirring solution of intermediate 47b) (4.65 g) in dry DCM (45 ml) was added TFAA (5 ml). The reaction mixture was then allowed to warm to RT and stirred for 3 h. The reaction mixture was neutralized with NaHCO₃ sat. and then phases were separated. The organic layer was extracted twice with NaHCO₃ sat. The combined aqueous layer was extracted back with DCM. The combined organic layer was washed with brine, dried over Na₂CO₃, filtered and volatiles were removed. The crude product was purified by column chromatography.

EXAMPLE 47

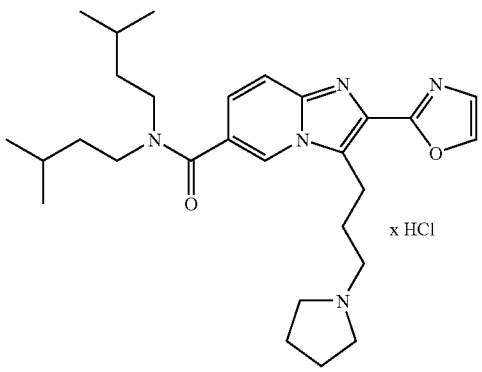

x HCl

Intermediate 47c) (1068 mg) was dissolved in acetonitrile (100 ml). Pyrrolidine (2003 μl) was added and the reaction mixture was stirred at 70° C. for 8 h. Volatiles were removed and the crude product was purified with preparative LC-MS. The purified compound was taken up with ethyl acetate and washed with saturated aqueous sodium bicarbonate solution. The aqueous phase was extracted three times with ethyl acetate. The combined organic layer was washed with brine, dried over sodium sulfate and the solvent was removed. The obtained oil was dissolved in ethyl acetate (10 ml) and 1 M HCl in diethyl ether (2 ml) was added. Volatiles were removed and the product was obtained in form of an off-white powder.

SYNTHESIS OF EXAMPLE 50

EXAMPLE 50

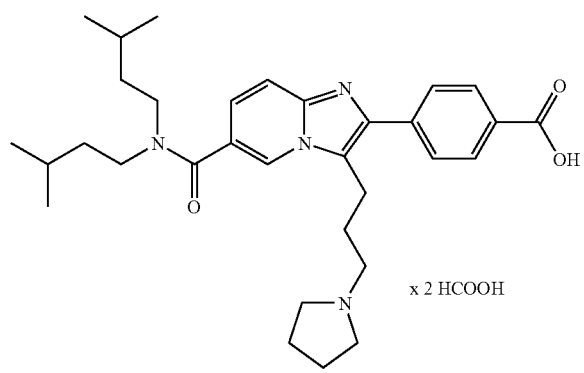

x 2 HCOOH

Example 25 (422 mg) was dissolved in concentrated hydrochloric acid and refluxed for 2 hours. The solvent was removed under reduced pressure to yield the title compound which was purified by preparative HPLC.

SYNTHESIS OF EXAMPLE 54

Intermediate 54a

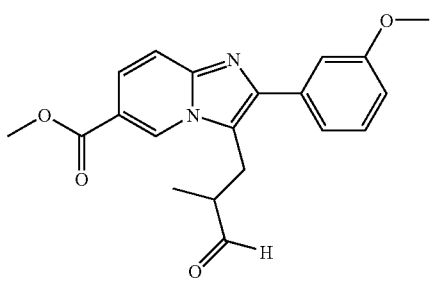

A mixture of 2-(3-methoxy-phenyl)-imidazo[1,2-a]pyridine-6-carboxylic acid methyl ester (1000 mg), methacrolein (990 mg), acetic anhydride (5.5 ml) and glacial acetic acid (14.5 ml) was heated in the microwave at 180° C. for 75 minutes. Then the volatiles were removed under reduced pressure. Methanol and 1N aqueous sodium bicarbonate solution were added and the mixture stirred for 2 h. The solvents were removed, and the residue dissolved in ethyl acetate and water. The organic layer was separated and dried over sodium sulfate. The solvent, was removed under reduced pressure to yield the title compound which was taken to the next step without further purification.

Intermediate 54b

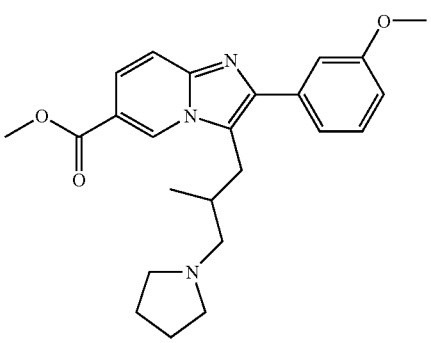

Intermediate 54a) (450 mg) was dissolved in dichloromethane (27 ml), pyrrolidine (0.11 ml) was added and the mixture stirred for 30 min at ambient temperature. Then sodium triacetoxyborohydride (360 mg) was added and the reaction was stirred overnight. Water was added and the aqueous phase was extracted twice with dichloromethane. The combined organic layers were dried over sodium sulfate and the solvent removed under reduced pressure. The product was purified by flash chromatography.

Intermediate 54c

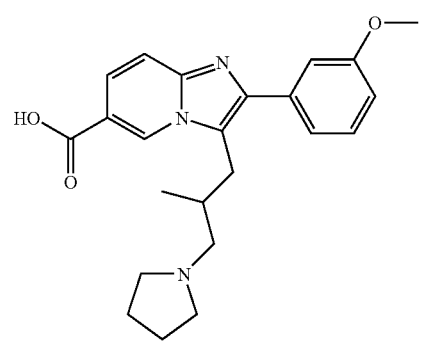

Intermediate 54b) (78 mg) was dissolved in tetrahydrofurane (3.5 ml) and cooled to 0° C. Then lithium hydroxide (0.19 ml, 2N in water) was added and the mixture was left to reach room temperature and stirred for 2 days. Ethyl acetate and brine were added. The white precipitate was dissolved by adding drops of citric acid (5%). The organic layer was separated and dried over sodium sulfate. The solvent was removed under reduced pressure to yield intermediate 54c).

EXAMPLE 54

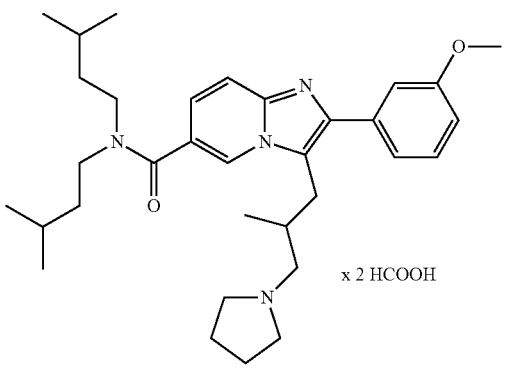

x 2 HCOOH

Intermediate 54c) (38 mg) was dissolved in DMF (5 ml). Then O-(7-azabenzotriazol-1-yl)-N,N,N',N'-tetramethyluronium hexafluorophosphate (HATU, 44 mg), diisopropylethylamine (20 µl) and diisoamylamine (24 µl) were added and the mixture stirred overnight at ambient temperature. Solvents were evaporated. The product was then dissolved in ethyl acetate. The organic layer was washed with brine, then with saturated sodium bicarbonate and with brine again. The organic layer was dried over sodium sulfate, filtered and the solvent evaporated. The product was purified by preparative HPLC to yield Example 54.

SYNTHESIS OF EXAMPLE 58

Intermediate 58a

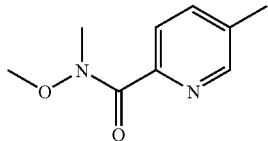

At 0° C., EDC (1608 mg) was added to 5-methyl-pyridine-2-carboxylic acid (1000 mg) in DCM (25 ml). The reaction mixture was stirred at 0° C. for 30 min and then N,O-dimethylhydroxylamine hydrochloride (818 mg) was added, followed by NMM (922 µl). The reaction was allowed to warm to RT and stirred over night. The reaction mixture was diluted with DCM (25 ml), and then extracted with NaHCO$_3$ sat. (2×25 ml). The aqueous layer was extracted back with DCM (25 ml). The combined organic layer was washed with brine, dried over Na$_2$SO$_4$, filtered and solvents were removed. The crude product was purified by column chromatography.

Intermediate 58b

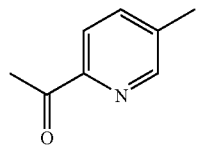

At −78° C., under argon atmosphere, to a stirring solution of intermediate 58a) (1270 mg) in dry THF (10 ml) was carefully added methyl lithium (1.6M in Et$_2$O, 13.2 ml). The reaction mixture was stirred at −78° C. for 90 minutes, and then hydrolyzed with NH$_4$Cl sat. (10 ml). The reaction mixture was diluted with diethyl ether (50 ml). The aqueous layer was extracted back with diethyl ether (2×10 ml). The combined organic layer was washed with brine, dried over Na$_2$SO$_4$, filtered and solvent was carefully removed. The product was purified by Kugelrohr distillation (10 mbar, 130° C.).

Intermediate 58c

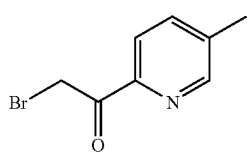

At RT, to a stirring solution of intermediate 58b) (541 mg) in AcOH (10 ml) was added 33% HBr in AcOH (2 ml) and then bromine (53 µl). After 30 minutes additional bromine (50 µl) was added and the reaction mixture stirred for 90 minutes. The reaction mixture was concentrated in vacuo and then poured in a saturated aqueous NaHCO$_3$ solution. It was extracted with three times with ethyl acetate. The combined organic layer was dried over Na$_2$SO$_4$, filtered and solvents were carefully removed. The crude product was purified by column chromatography.

Intermediate 58d

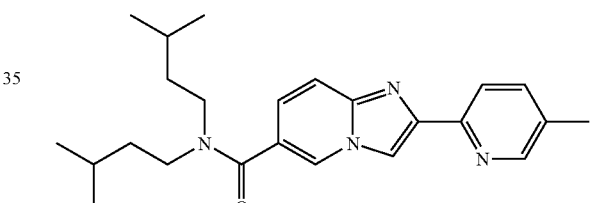

Intermediate 58c) (350 mg) and intermediate 9b) (522 mg) were dissolved in MeCN (10 ml) and then heated to 180° C. for 30 min using microwave irradiation. Volatiles were removed and the crude product was purified by column chromatography.

Intermediate 58e

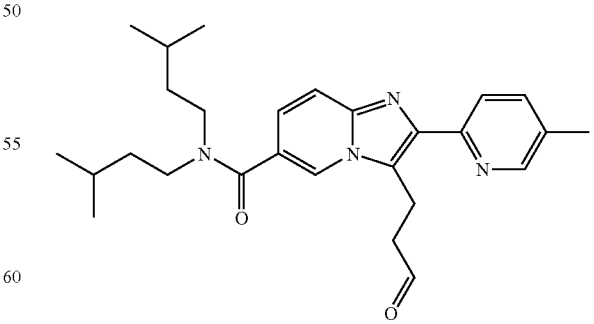

Acroleine (233 µl) was added to a solution of intermediate 58d) (381 mg) in glacial acetic acid (6 ml) followed by acetic anhydride (2 ml) and the mixture was heated at 180° C. in a microwave reactor for 30 min. The reaction mixture was poured in a mixture of saturated aqueous sodium bicarbonate solution (100 ml) and saturated aqueous sodium carbonate solution (50 ml) to reach a basic pH and then extracted with ethyl acetate (2×50 ml). The organic layer was washed with brine, dried on Na$_2$SO$_4$, filtered and the solvent was removed. A 1M solution of sodium bicarbonate in water (10 ml) was added to the crude product in methanol (50 ml). The reaction mixture was stirred at RT over night. The reaction mixture was concentrated in vacuum and then partitioned between saturated aqueous NaHCO$_3$ solution and DCM. The aqueous layer was extracted twice with DCM. The combined organic layer was washed with brine, dried over Na$_2$SO$_4$, filtered, and solvent was removed.

EXAMPLE 58

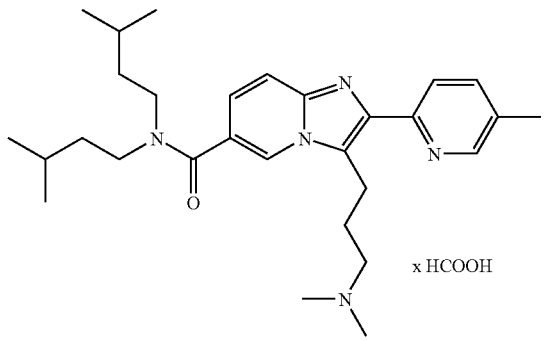

Intermediate 58e) (83 mg) and 2M dimethylamine in THF (463 µl) were dissolved in 1,2-dichloroethane (5 ml). After 1 h stirring at RT, sodium triacetoxyborohydride (782 mg) was added. The mixture was stirred at ambient temperature overnight. The reaction mixture was extracted with 1M NaHCO$_3$ (2×2 ml). The aqueous layer was extracted back with DCE (2 ml). The combined organic layer was washed with brine, dried over Na$_2$SO$_4$, filtered, and evaporated to dryness in vacuum. The crude product was purified with preparative LC-MS.

SYNTHESIS OF EXAMPLE 59

Intermediate 59a

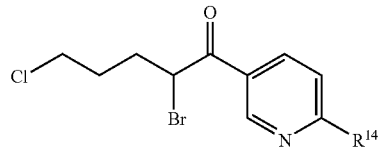

R$^{14}$ = Cl or Br

Under argon, to a stirring suspension of copper(II)-bromide (19.36 g) in ethyl acetate (200 ml) was added 6-chloro-3-(5-chlorovaleryl)-pyridine (10.06 g) in chloroform (200 ml). The resulting mixture was stirred at reflux for 20 h. The reaction mixture was filtrated on Celite and concentrated in vacuum.

The residue of the filtartion was washed with acetonitrile and the filtrate was concentrated in vacuum. The residue was up taken in ethyl acetate (500 ml) and washed with saturated sodium bicarbonate solution (500 ml). The aqueous layer was extracted with twice with ethyl acetate. The organic layers were combined with the first isolated batch, washed with saturated sodium bicarbonate solution, water and brine, dried over MgSO$_4$, filtered and the solvent was removed under reduced pressure.

Intermediate 59b

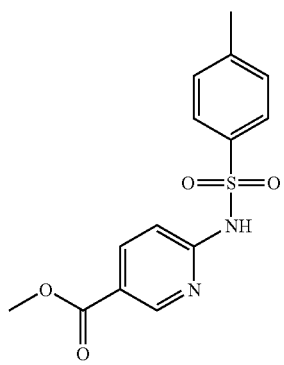

To a solution of 6-aminonicotinic acid methyl ester (20.09 g) in dry pyridine (400 ml) under argon atmosphere was added tosyl chloride (28.94 g). The reaction mixture was stirred at 85° C. for 16 h. The solvent was removed under reduced pressure, the residue taken up with water and stirred for 2 h. A beige precipitate was formed. It was filtered, washed twice with water and dried over Sicapent.

Intermediate 59c

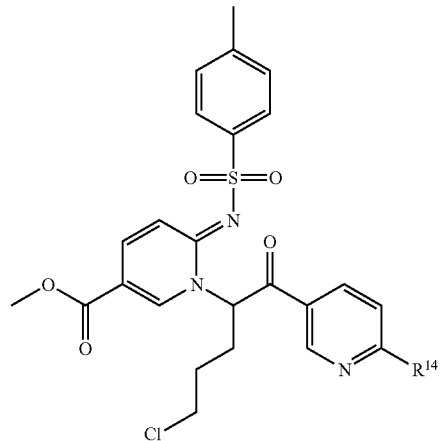

R$^{14}$ = Cl or Br

A mixture of intermediate 59b) (9.74 g) and intermediate 59a) (10.24 g) in acetonitrile (300 ml) was treated with ethyldiisopropylamine (6654 µl) and stirred at 50° C. overnight. The solvent was removed under reduced pressure. The product was purified with flash chromatography.

Intermediate 59d

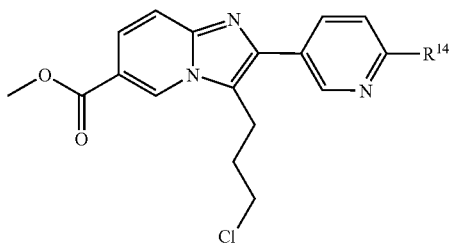

R[14] = Cl or Br

Intermediate 59c) (15.07 g) was dissolved in dry DCM (180 ml) and cooled to 0° C. Trifluoroacetic acid anhydride (20 ml) was added and the reaction mixture was allowed to stir at room temperature overnight. The reaction mixture was diluted with DCM (200 ml) and carefully extracted with sat. sodium bicarbonate solution. The aqueous layer was extracted twice with DCM. The combined organic layer was washed with brine, dried over sodium sulfate and the solvent was removed under reduced pressure.

Intermediate 59e

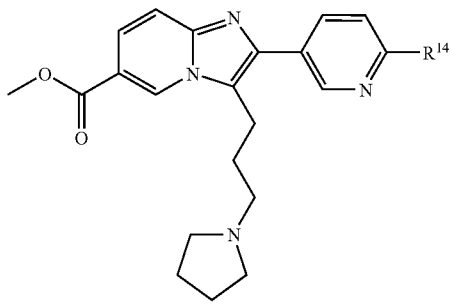

R[14] = Cl or Br

Intermediate 59d) (5.0 g), acetonitrile (120 ml) and pyrrolidine (10.9 ml) were stirred at 70° C. overnight. The solvent was removed under reduced pressure. The product was triturated with acetone, filtered and dried in a vacuum oven overnight.

Intermediate 59f

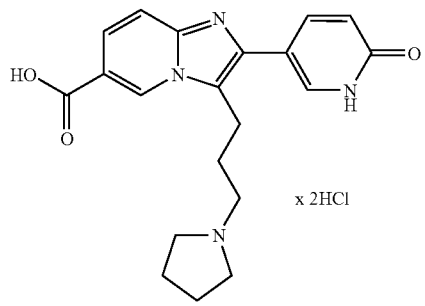

x 2HCl

Intermediate 59e) (4.6 g) was dissolved in 3 M HCl in water (150 ml) and the reaction mixture was stirred at 120° C. for 36 h. The solvent was removed under reduced pressure, the residue co-evaporated twice with toluene and the product was dried on high vacuum for 2 d. The product was used as such for the next step without further purification.

EXAMPLE 59

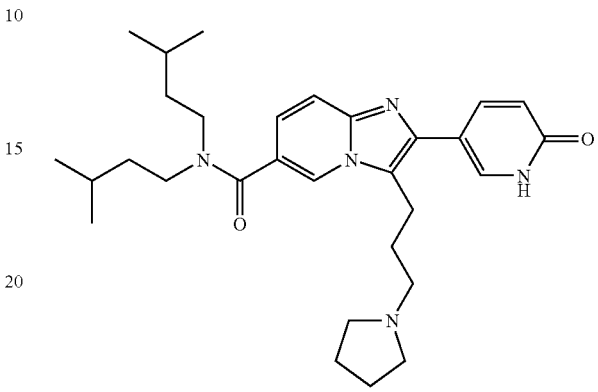

Intermediate 59f) (1000 mg) was dissolved in DMF (10 ml) and then EDC (525 mg), HOAt (373 mg) and DIEA (1431 µl) were added. The reaction mixture was stirred for 1 h. Diisoamylamine (562 µl) was added and the reaction mixture was stirred overnight. Volatiles were removed and then the residue was dissolved in of ethyl acetate (200 ml). The organic layer was washed with NaHCO₃ sat. (2×100 ml) then the combined aqueous layers were extracted back with ethyl acetate (100 ml). The combined organic layer was washed with brine, dried over Na₂SO₄, filtrated and the solvent was removed under reduced pressure. The crude product was purified with preparative LC-MS.

SYNTHESIS OF EXAMPLE 64

EXAMPLE 64

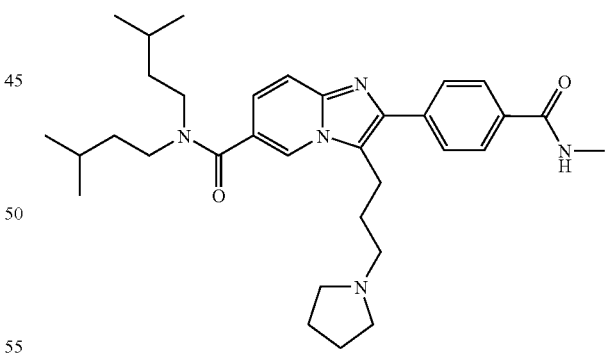

Example 50 (200 mg), O-(7-azabenzotriazol-1-yl)-N,N,N',N'-tetramethyluronium hexafluorophosphate (HATU, 185 mg) and diisopropylethylamine (1.95 ml) in dimethylformamide (4 ml) were stirred for 15 minutes at ambient temperature before a solution of methyl amine 2N in tetrahydrofurane (0.28 ml) was added and the stirring continued overnight. Ethyl acetate was added. The organic layer was washed with saturated sodium bicarbonate solution and brine and dried over sodium sulfate. The solvent was removed under reduced pressure to yield the title compound which was purified by preparative HPLC.

SYNTHESIS OF EXAMPLE 79

Intermediate 79a

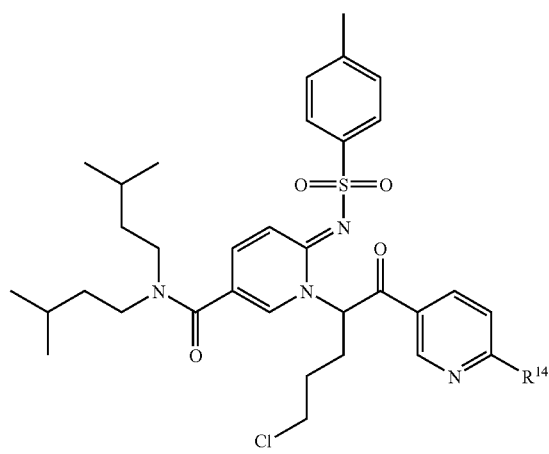

R[14] = Cl or Br

At 50° C. to a stirring suspension of intermediate 59a) (679 mg) in acetonitrile (15 ml) was added DIEA (806 µl). The obtained solution was stirred for 10 minutes then intermediate 9c) (993 mg) in acetonitrile (15 ml) was added. The obtained solution was stirred at 50° C. for 2 h. Solvents were removed and the obtained oil was purified by column chromatography.

Intermediate 79b

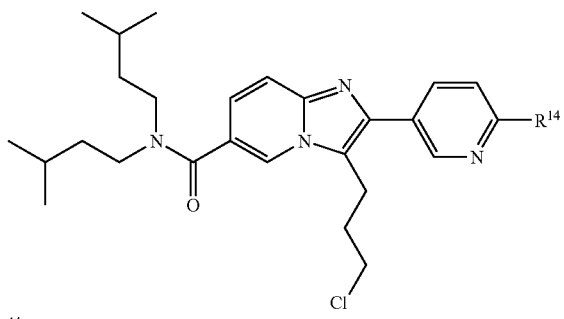

R[14] = Cl or Br

At 0° C., to a stirring solution of intermediate 79a) (1.35 g) in dry DCM (18 ml) was added TFAA (2 ml). The reaction mixture was then allowed to warm to RT and stirred overnight. Volatiles were removed and the obtained oil was purified by column chromatography.

Intermediate 79c

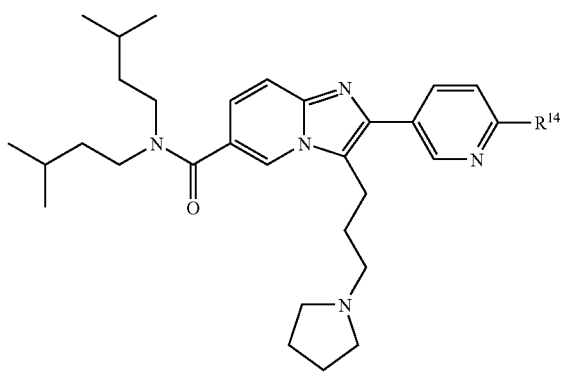

R[14] = Cl or Br

Intermediate 79b) (100 mg), acetonitrile (5 ml) and pyrrolidine (167 µl) were stirred at 70° C. overnight. The solvent was removed under reduced pressure. The product was purified by column chromatography.

EXAMPLE 79

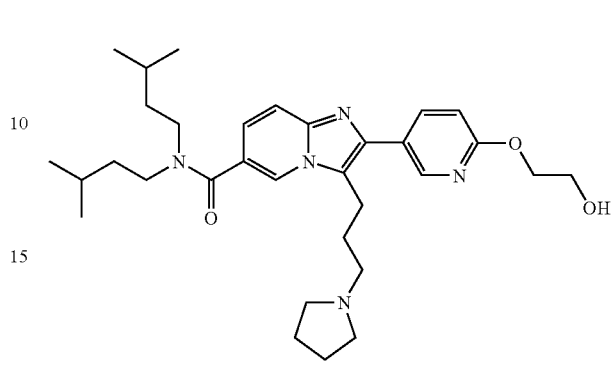

To a suspension of sodium hydride (31 mg) in DMF (5 ml) was added ethyleneglycol (22 µl) under argon atmosphere. The reaction mixture was stirred at room temperature for 30 min and then intermediate 79c) (70 mg) in DMF (5 ml) was added. The mixture was stirred at 140° C. overnight. The mixture was cooled and hydrolyzed with water. Solvent was evaporated and the residue taken up in ethyl acetate. The organic layer was extracted with water and brine and the solvent was removed under reduced pressure. The crude product was purified using preparative LC-MS.

SYNTHESIS OF EXAMPLE 90

Intermediate 90a

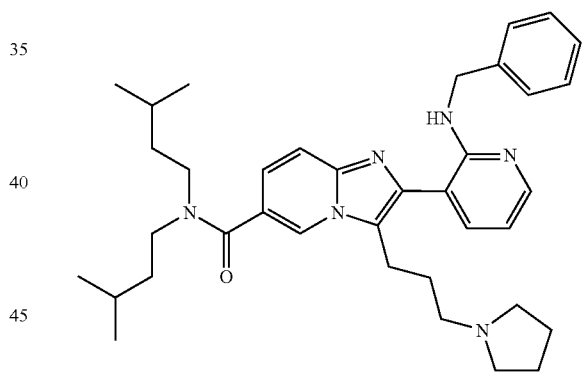

2-(2-Chloro-pyridin-3-yl)-3-(3-pyrrolidin-1-yl-propyl)-imidazo[1,2-a]pyridine-6-carboxylic acid bis-(3-methyl-butyl)-amide (100 mg) and benzyl amine (0.5 ml) were heated in the microwave at 150° C. for 2 h. The mixture was purified by flash chromatography to yield the title compound.

EXAMPLE 90

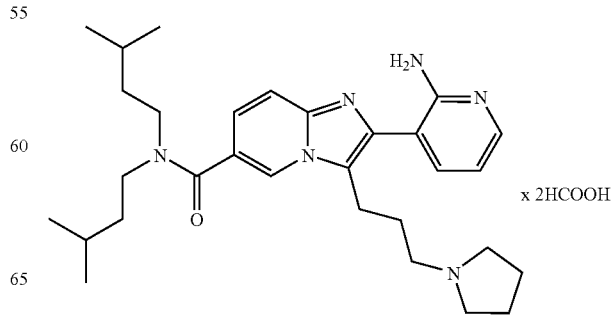

x 2HCOOH

Trifluoromethanesulfonic acid (300 mg) was added dropwise to intermediate 90a) (78 mg) in dry dichloromethane (1.5 ml) at 0° C. Then the mixture was heated to 40° C. for 3 hours. Again the mixture was cooled to 0° C. and another 300 mg of trifluoromethanesulfonic acid were added followed by heating to reflux for 2 h. Solvents were evaporated under reduced pressure. The title compound was obtained after purification by preparative HPLC.

SYNTHESIS OF EXAMPLES 91 AND 92

EXAMPLES 91 AND 92

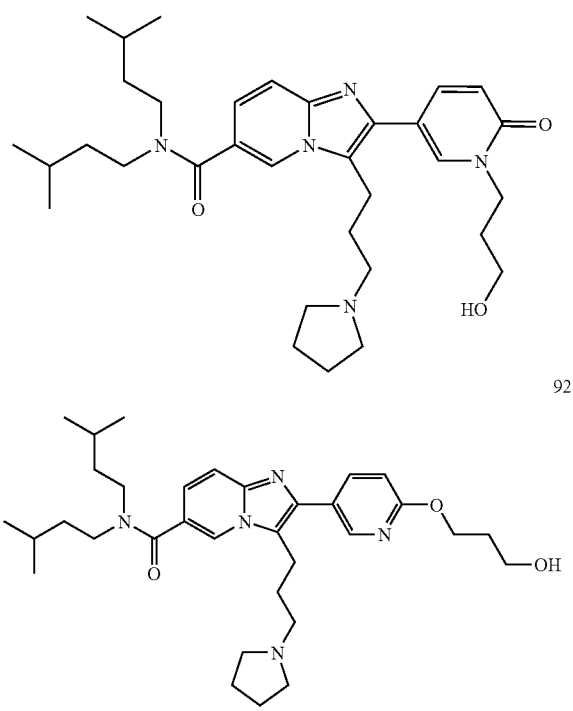

Example 59) (100 mg) was dissolved in acetone (5 ml) and then potassium carbonate (41 mg) and 3-bromo-1-propanol (20 μl) were added. The reaction mixture was stirred at 60° C. overnight, filtered and the solvent was removed under reduced pressure. The products were separated with preparative LC-MS.

SYNTHESIS OF EXAMPLE 98

Intermediate 98a

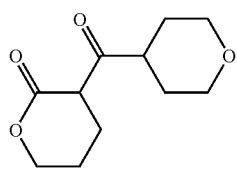

Prior to be used, δ-valerolactone was distillated under reduce pressure (bp 106° C./22 mbar). To a stirring suspension of sodium hydride (60% in oil, 2.66 g) in dry toluene (100 ml) at reflux was added dropwise a mixture of methyl tetrahydro-2H-pyran-4-carboxylate (8.87 ml) and δ-valerolactone (6.34 g) in dry toluene (50 ml). After addition, the reaction mixture was stirred at reflux temperature over night. After cooling to room temperature, the reaction mixture was poured in ice cold water (300 ml). Solid in the flask was recovered with water (150 ml) and toluene (50 ml). After phase separation, the aqueous layer was acidified using AcOH (5 ml) and extracted with ethyl acetate (3×150 ml). The combined organic layer was washed with brine, dried over Na$_2$SO$_4$, filtered and volatiles were removed. The crude product was purified by column chromatography.

Intermediate 98b

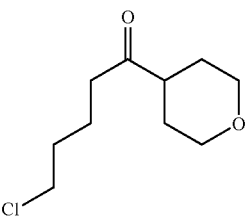

Intermediate 98a) (1.86 g) was stirred in concentrated hydrochloric acid (10 ml) at 80° C. for 1 h. The reaction mixture was poured in Na$_2$CO$_3$ sat. (300 ml) and extracted with DCM (3×100 ml). The combined organic layer was washed with brine, dried over Na$_2$SO$_4$, filtered and volatiles were removed.

Intermediate 98c

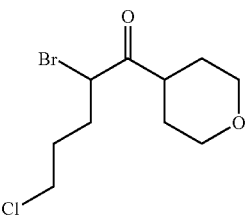

Under argon, to a stirring suspension of copper(II) bromide (1965 mg) in ethyl acetate (25 ml) was added intermediate 98b) (934 mg) in chloroform (25 ml). The resulting mixture was stirred at reflux overnight. The reaction mixture was filtrateted through Celite and the Celite pad was thoroughly washed with ethyl acetate. The organic layer was extracted twice with NaHCO$_3$ sat. The aqueous layer was extracted back with ethyl acetate. The combined organic layer was washed with brine, dried over Na$_2$SO$_4$, filtered and volatiles were removed.

Intermediate 98d

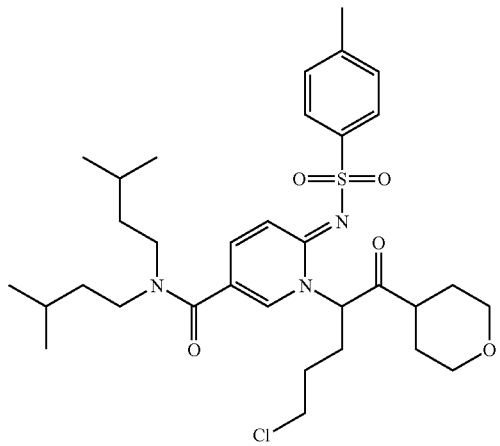

At 50° C. to a stirring suspension of 9c) (1994 mg) in acetonitrile (50 ml) was added DIEA (1610 μl). The obtained solution was stirred at 50° C. for 15 minutes then intermediate 98c) (1.25 g) in acetonitrile (50 ml) was added. The obtained reaction mixture was stirred at 50° C. over night. Volatiles were removed and the crude was purified by column chromatography.

Intermediate 98e

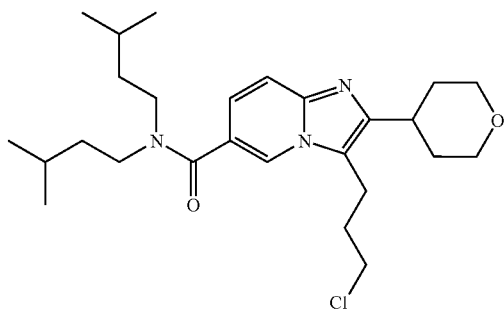

Under argon atmosphere, to a solution of intermediate 98d) (525 mg) in DCE (9 ml) was added TFAA (1 ml), and the reaction mixture was stirred at RT for 4 days. Additional TFAA (1 ml) and DCE (9 ml) were added and the reaction mixture heated to reflux over night. Volatiles were removed and the residue was taken up in ethyl acetate (50 ml). The organic layer was extracted twice with $Na_2CO_3$ sat. (25 ml). The combined aqueous layer was extracted back with ethyl acetate (25 ml). The combined organic layer was washed with brine, dried over $Na_2SO_4$, filtered, and volatiles were removed. The crude product was purified by column chromatography.

EXAMPLE 98

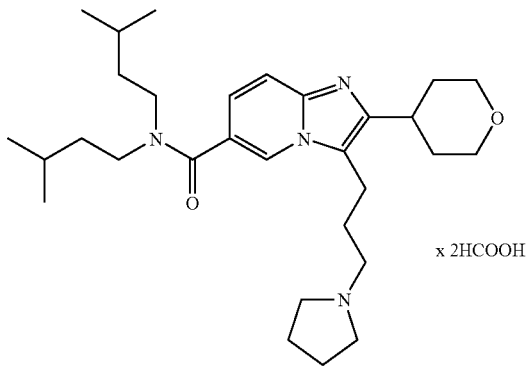

To a stirring solution of intermediate 98e) (85 mg) in MeCN (10 ml) was added pyrrolidine (172 µl) and the reaction mixture was stirred in a sealed tube at 50° C. for 2 d. Volatiles were removed and the crude product was purified by preparative LC-MS.

SYNTHESIS OF EXAMPLE 109

Intermediate 109a

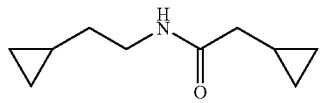

To a solution of cyclopropylacetic acid (2002 mg) in DCM (100 ml) at 0° C. was added EDC (3834 mg) and HOBt (3063 mg). The reaction mixture was stirred at 0° C. for 30 min. Cyclopropylethylamine (1703 mg) and DIEA (10.45 ml) were added and the reaction mixture was stirred at room temperature overnight. The reaction mixture was extracted with 1.0 N HCl (100 ml), sat. $NaHCO_3$ (100 ml), water (100 ml) and brine (100 ml). The organic layer was dried over $Na_2SO_4$ and evaporated in vacuo to dryness.

Intermediate 109b

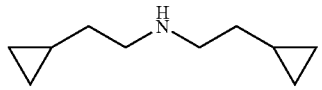

A solution of intermediate 109a) (2448 mg) in anhydrous THF (40 ml) was added dropwise under argon atmosphere to a suspension of lithium aluminum hydride (1389 mg) in anhydrous THF (60 ml) at room temperature. The reaction mixture was heated to reflux temperature and stirred for another 2 days. The reaction mixture was hydrolyzed by addition of 10% aqueous KOH (100 ml) at 0° C. After stirring for 20 min at room temperature the reaction mixture was filtered and the solid was washed with diethyl ether (100 ml). The biphasic filtrate was transferred into a separation funnel and the organic layer was washed with water and brine. The combined aqueous layer was washed twice with diethyl ether (2×100 ml). The combined organic layer was washed with brine, dried over magnesium sulfate and the solvent was removed under reduced pressure.

Intermediate 109c

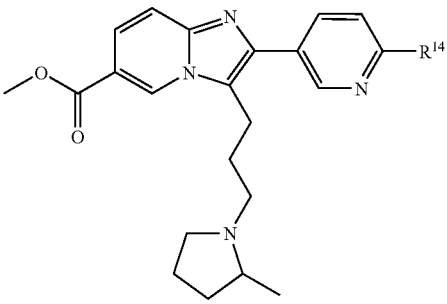

$R^{14}$ = Cl or Br

Intermediate 59d) (2.0 g), acetonitrile (30 ml) and 2-methyl-pyrrolidine (1.27 ml) were stirred at 70° C. overnight. DIEA (500 µl) was added and the mixture was stirred at 70° C. for 20 h. The solvent was removed under reduced pressure and the residue taken up with ethyl acetate and washed twice with saturated sodium bicarbonate solution, water and brine. The organic layer was dried over sodium sulfate, filtered and the solvent was removed under reduced pressure. The crude product was purified by column chromatography.

Intermediate 109d

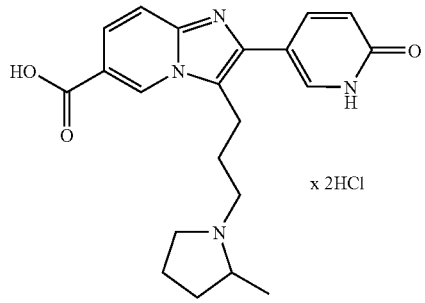

Intermediate 109c) (1.7 g) was dissolved in 3 M HCl in water (100 ml) and the reaction mixture was stirred at 120° C. for 24 h. The solvent was removed under reduced pressure, the residue co-evaporated twice with toluene and the product was dried on high vacuum for 3 h and subsequently in an oven at 40° C. under reduced pressure for 3 d. The product was used as such for the next step without further purification.

EXAMPLE 109

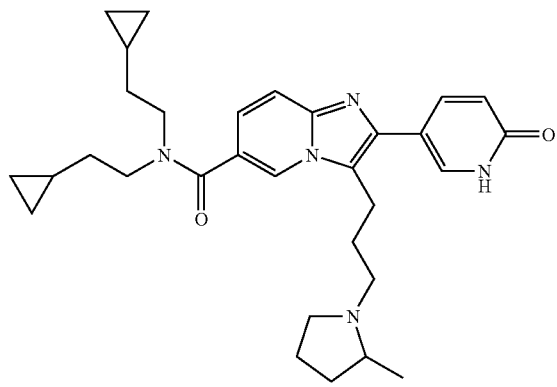

Intermediate 109d (600 mg) was dissolved in DMF (5 ml) and then EDC (299 mg), HOAt (212 mg) and DIEA (815 µl) were added. The reaction mixture was stirred for 1 h. Intermediate 109b (239 mg) was added and the reaction mixture was stirred overnight. Volatiles were removed and then the residue was dissolved in of ethyl acetate (100 ml). The organic layer was washed with NaHCO₃ sat. (2×50 ml) then the combined aqueous layers were extracted back with ethyl acetate (50 ml). The combined organic layer was washed with brine, dried over Na₂SO₄, filtrated and the solvent was removed under reduced pressure. The crude product was purified by preparative LC-MS.

SYNTHESIS OF EXAMPLE 110

EXAMPLE 110

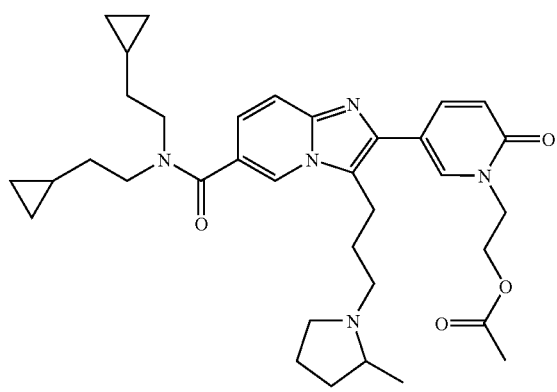

Example 109 (230 mg) was dissolved in acetone (7 ml) and then cesium carbonate (222 mg) and 2-bromoethyl acetate (55 µl) were added. The reaction mixture was stirred at 60° C. overnight, filtered and the solvent was removed under reduced pressure. The N- and O-alkylated products were separated by preparative LC-MS.

SYNTHESIS OF EXAMPLES 111 AND 112

EXAMPLES 111 AND 112

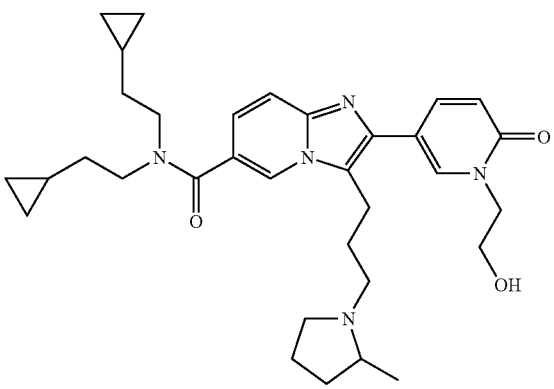

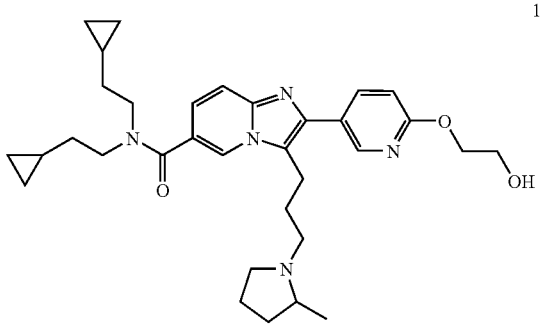

A mixture of Example 110 and the O-alkylated side-product (crude product before purification) (116 mg) was dissolved in THF (10 ml) and cooled to 0° C. Lithium hydroxide monohydrate (30 mg) in water (2 ml) was added and the reaction mixture was stirred at 0° C. for 30 min and at room temperature for 2.5 h. The reaction mixture was concentrated and then partitioned between ethyl acetate and water. The aqueous layer was extracted three times with ethyl acetate. The combined organic layer was washed with brine, dried over sodium sulfate and the solvent was removed under reduced pressure. The products were separated by preparative LC-MS.

SYNTHESIS OF EXAMPLE 114

Intermediate 114a

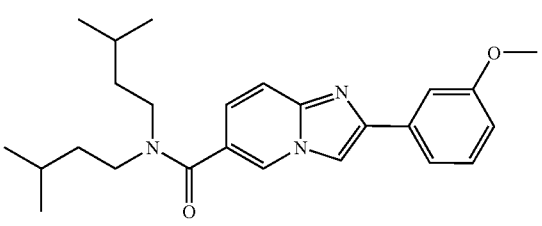

To a solution of 6-amino-N,N-bis-(3-methyl-butyl)-nicotinamide (100 mg) in MeCN (2 ml) was added 2-bromo-3'-methoxyacetophenone in MeCN (2 ml) and the mixture was heated at 170° C. under microwave irradiation for 40 min. The solvent was evaporated and the crude mixture was purified by flash chromatography (EtOAc/cyclohexane) to yield the title compound.

EXAMPLE 114

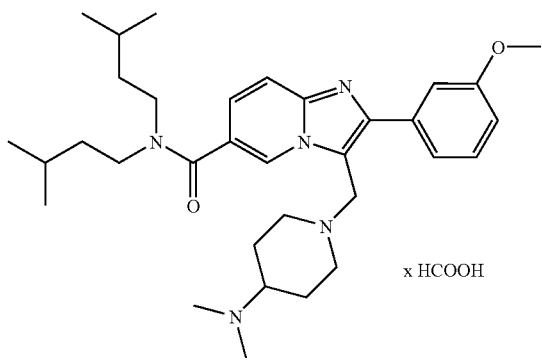

x HCOOH

A solution of 4-dimethylamino-piperidine (14.1 mg) in HOAc and formaldehyde (37% aqueous solution, 8.2 μl) was added to intermediate 114a) (30 mg) in HOAc and the mixture was heated at 60° C. for 16 h. After evaporation of the solvent the crude reaction mixture was purified by preparative HPLC to yield the title compound.

SYNTHESIS OF EXAMPLE 119

Intermediate 119a

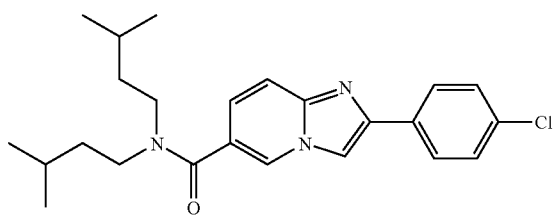

To a solution of 6-amino-N,N-bis-(3-methyl-butyl)-nicotinamide (1000 mg) in MeCN (10 ml) was added 2-bromo-4'-chloroacetophenone in MeCN (10 ml) and the mixture was heated at 160° C. under microwave irradiation for 15 min. Upon cooling a precipitate formed that was collected and dried to yield the title compound.

EXAMPLE 119

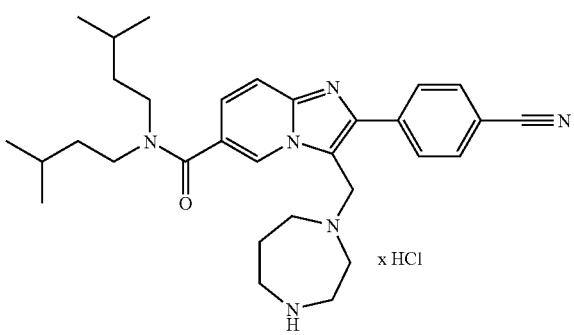

x HCl

A solution of [1,4]diazepane-1-carboxylic acid tert-butyl ester (22.3 mg) in HOAc and formaldehyde (37% aqueous solution, 13.5 μl) was added to intermediate 119a) (30 mg) in HOAc and the mixture was heated at 60° C. for 16 h. After evaporation of the solvent the crude reaction mixture was purified by flash chromatography (DCM/MeOH). The resulting Boc-protected intermediate was then treated with 4M HCl/dioxane for 1 h to yield the title compound.

SYNTHESIS OF EXAMPLE 143

Intermediate 143a

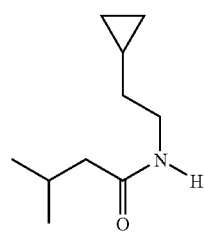

2-Cyclopropyl-ethylamine hydrochloride (700 mg) was suspended in dichloromethane (14 ml). The solution was cooled to 0° C., followed by addition of isovaleryl chloride (0.84 ml) and triethylamine (1.60 ml). The reaction was allowed to warm to room temperature and the reaction mixture was stirred for 4 h. The solvent was evaporated and the residue was partitioned between ethyl acetate (50 ml) and NaHCO$_3$ sat. (40 ml). The aqueous layer was extracted twice with ethyl acetate (50 ml) and the combined organic phases were washed with brine (40 ml). The organic layer was dried over Na$_2$SO$_4$, filtrated and the solvent was removed under reduced pressure. The crude product was purified with preparative LC-MS.

Intermediate 143b

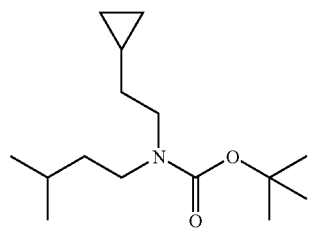

Intermediate 143a) (838 mg) was treated with borane-tetrahydrofuran complex (1M solution in THF, 14.9 ml) and the reaction mixture was stirred under reflux for 6 h. Then the reaction mixture was cooled to 0° C. and methanol (7 ml) was added carefully. The reaction mixture was refluxed for 5 h and cooled to 0° C. Di-tert-butyl dicarbonate dissolved in DCM (7 ml) was added and the reaction mixture was stirred at room temperature over night. Volatiles were removed and the residue was dissolved in ethyl acetate (100 ml). The organic layer was washed with water (60 ml) and brine (60 ml). The organic layer was dried over Na$_2$SO$_4$, filtrated and the solvent was removed under reduced pressure. The crude product was used without other purification.

Intermediate 143c

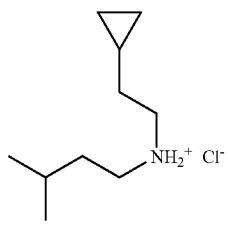

Intermediate 143b) (1.26 g) was dissolved in DCM (30 ml) and 4 M HCl in dioxane (1.48 ml) was added. The reaction mixture was stirred at room temperature for 14 h. The solvent was evaporated and the resulting white solid was triturated with ether and the product was collected by filtration, washed with ether and dried on the high-vacuum. The solid was used without further purification.

Intermediate 143d

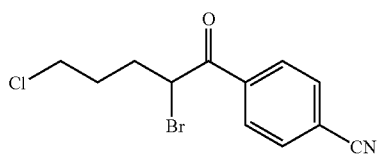

Under argon, to a stirring suspension of copper(II)-bromide (3.62 g) in ethyl acetate (60 ml) was added 5-chloro-1-(4-cyanophenyl)-1-oxopentane (3.00 g) in chloroform (60 ml). The resulting mixture was stirred at reflux over night. Additional copper(II)-bromide (0.60 g) was added and the reaction was refluxed for 3 h. The reaction mixture was filtrated on Celite, washed with ethyl acetate and concentrated in vacuum. The product was purified with flash chromatography.

Intermediate 143e

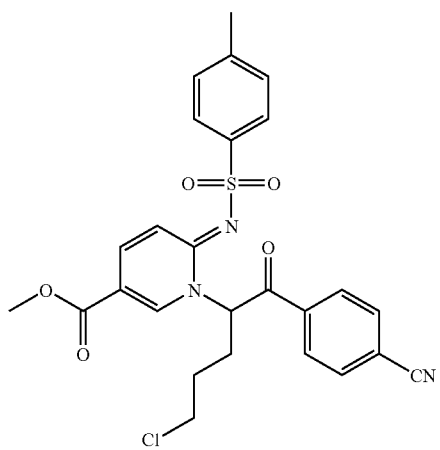

Intermediate 143d) (3.00 g) was dissolved in acetonitrile (80 ml). Ethyldiisopropylamine (3.2 ml) was added and the reaction mixture was heated at 85° C. Intermediate 59b) (2.80 g) dissolved in acetonitrile (20 ml) was added and the reaction mixture was refluxed for 1 h. The solvent was removed under reduced pressure. The product was purified with flash chromatography.

Intermediate 143f

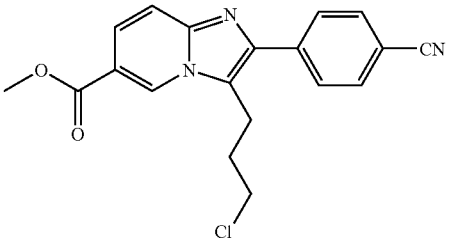

Intermediate 143e) (4.67 g) was dissolved in dry DCM (90 ml) and cooled to 0° C. Trifluoroacetic acid anhydride (12 ml) was added and the reaction mixture was allowed to stir at room temperature for 6 h. The solvent was removed under reduced pressure. The residue was dissolved in ethyl acetate (200 ml) and was poured in a sat. sodium bicarbonate solution. The obtained white precipitate was filtrated off, washed with water and dried under high vacuum.

Intermediate 143g

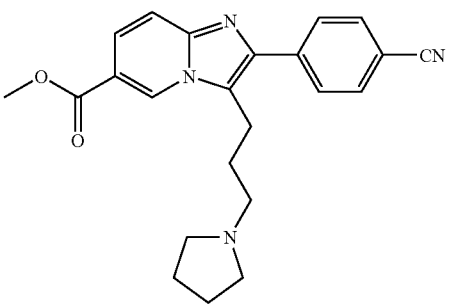

Intermediate 143f) (1.50 g), acetonitrile (40 ml) and pyrrolidine (3.5 ml) were stirred at 70° C. for 6 h. Half of the solvent was removed under reduced pressure and the remained solution was cooled on an ice bath for 2 h. The obtained solid was filtrated and washed with cooled acetonitrile. The product was dried under high vacuum.

Intermediate 143h

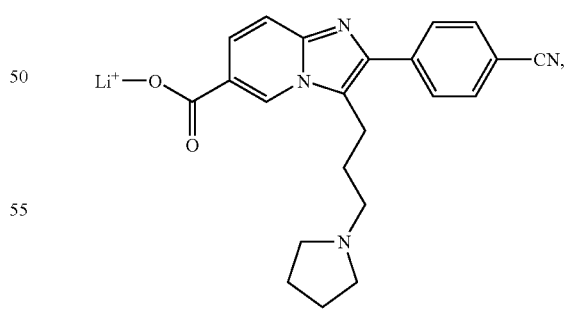

Intermediate 143g) (313 mg) was dissolved in THF (10 ml) and 2 M LiOH in water (0.92 ml) was added. The reaction mixture was stirred at room temperature over night. Additional THF (1.5 ml) and 2 M LiOH in water (0.1 ml) were added and the reaction mixture was stirred at room temperature for 3 h. The obtained solid was filtrated, washed with cooled THF and dried on high vacuum. The product was used as such for the next step without further purification.

EXAMPLE 143

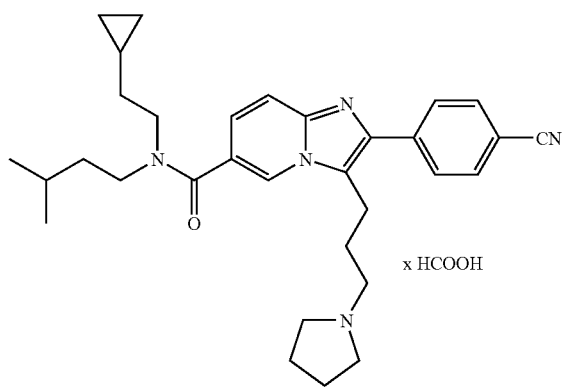

x HCOOH

Intermediate 143h) (40 mg) was dissolved in DMF (3 ml) and then HATU (49 mg), DIEA (22 μl) and intermediate 143c) (23 mg) were added. The reaction mixture was stirred for 1 h. The reaction was not completed, therefore additional intermediate 143c) (10 mg) and DIEA (22 μl) were added and the reaction mixture was stirred for 2 h. Volatiles were removed and then the residue was dissolved in ethyl acetate (50 ml). The organic layer was washed with brine (40 ml), NaHCO$_3$ sat. (40 ml) and brine (40 ml). The organic layer was dried over Na$_2$SO$_4$, filtrated and the solvent was removed under reduced pressure. The crude product was purified with preparative LC-MS.

Biological Assays

A. Binding Assay

A membrane binding assay is used to identify competitive inhibitors of fluorescence labeled NDP-alpha-MSH binding to HEK293 cell membrane preparations expressing human melanocortin receptors.

The test compound or unlabeled NDP-alpha-MSH is dispensed at varying concentrations to a 384 well microtiter plate. Fluorescence labeled NDP-alpha-MSH is dispensed at a single concentration, followed by addition of membrane preparations. The plate is incubated for 5 h at room temperature.

The degree of fluorescence polarization is determined with a fluorescence polarization microplate reader.

B. Functional Assay

Agonistic activity of human melanocortin receptors is determined in a homogeneous membrane based assay. Competition between unlabeled cAMP and a fixed quantity of fluorescence labeled cAMP for a limited number of binding sites on a cAMP specific antibody is revealed by fluorescence polarization.

The test compound or unlabeled NDP-alpha-MSH is dispensed at varying concentrations to a 384 well microtiter plate. Membrane preparations from HEK293 cells expressing the human melanocortin receptors are added. After a short preincubation period, an appropriate amount of ATP, GTP and the cAMP antibody is added and the plate is further incubated before the fluorescence labeled cAMP conjugate is dispensed. The plate is incubated for 2 h at 4° C. before it is read on a fluorescence polarization microplate reader. The amount of cAMP produced as a response to a test compound is compared to the production of cAMP resulting from stimulation with NDP-alpha-MSH.

Representative compounds of the present invention were tested and found to bind to the melanocortin-4 receptor. These compounds were generally found to have IC$_{50}$ values less than 2 μM. Representative compounds of the present invention were also tested in the functional assay and found generally not to activate the melanocortin-4 receptor.

TABLE 8

Biological data for the examples of the invention

| Example | hMC-4R binding assay IC$_{50}$/μM | hMC-4R functional assay EC$_{50}$/μM | % activation functional assay |
|---|---|---|---|
| SHU-9119 | a | — | 7 |
| NDP-α-MSH | a | a | 100 |
| 1 | b | — | 0 |
| 2 | a | — | 0 |
| 3 | b | — | 0 |
| 4 | b | — | 0 |
| 5 | b | — | 0 |
| 6 | a | — | 0 |
| 7 | b | — | 0 |
| 8 | a | — | 0 |
| 9 | a | — | 0 |
| 10 | c | — | 0 |
| 11 | a | — | 0 |
| 12 | a | — | 0 |
| 13 | c | — | 0 |
| 14 | a | — | 0 |
| 15 | b | — | 0 |
| 16 | a | — | 0 |
| 17 | a | — | 0 |
| 18 | b | — | 0 |
| 19 | a | — | 0 |
| 20 | b | a | −18 |
| 21 | a | — | 0 |
| 22 | b | — | 0 |
| 23 | b | — | 0 |
| 24 | c | — | 0 |
| 25 | a | — | 0 |
| 26 | b | — | 0 |
| 27 | c | — | 0 |
| 28 | b | — | 0 |
| 29 | a | — | 0 |
| 30 | a | — | 0 |
| 31 | a | — | 0 |
| 32 | b | — | 0 |
| 33 | a | a | −22 |
| 34 | a | a | −18 |
| 35 | a | — | 0 |
| 36 | c | — | 0 |
| 37 | a | — | 0 |
| 38 | c | — | 0 |
| 39 | a | — | 0 |
| 40 | b | — | 0 |
| 41 | a | — | 0 |
| 42 | a | — | 0 |
| 43 | a | — | 0 |
| 44 | a | — | 0 |
| 45 | a | — | 0 |
| 46 | b | — | 0 |
| 47 | a | — | 0 |
| 48 | a | — | 0 |
| 49 | a | — | 0 |
| 50 | b | — | −1 |
| 51 | a | — | 0 |
| 52 | b | — | 0 |
| 53 | b | — | 3 |
| 54 | b | — | 0 |
| 55 | b | — | 0 |
| 56 | a | — | 0 |
| 57 | a | — | 0 |
| 58 | c | — | 0 |
| 59 | a | — | 0 |
| 60 | b | — | 0 |
| 61 | b | — | 0 |
| 62 | b | — | 0 |

TABLE 8-continued

Biological data for the examples of the invention

| Example | hMC-4R binding assay $IC_{50}/\mu M$ | hMC-4R functional assay $EC_{50}/\mu M$ | % activation functional assay |
|---|---|---|---|
| 63 | b | — | 0 |
| 64 | a | — | 0 |
| 65 | a | — | 0 |
| 66 | b | — | 0 |
| 67 | a | — | 0 |
| 68 | b | — | 0 |
| 69 | a | — | 0 |
| 70 | b | — | 0 |
| 71 | b | — | 0 |
| 72 | b | — | 2 |
| 73 | b | — | −3 |
| 74 | b | — | 1 |
| 75 | a | — | 1 |
| 76 | b | — | 4 |
| 77 | a | — | 4 |
| 78 | a | — | 2 |
| 79 | a | — | 11 |
| 80 | b | b | −35 |
| 81 | a | — | −9 |
| 82 | a | a | −17 |
| 83 | a | — | −1 |
| 84 | a | — | −8 |
| 85 | a | — | −2 |
| 86 | a | — | −11 |
| 87 | c | — | 0 |
| 88 | b | — | −2 |
| 89 | a | a | −25 |
| 90 | b | c | −41 |
| 91 | b | b | −29 |
| 92 | b | a | −31 |
| 93 | b | — | 0 |
| 94 | c | — | −13 |
| 95 | a | — | 0 |
| 96 | a | — | 0 |
| 97 | a | — | 1 |
| 98 | b | — | −8 |
| 99 | a | — | 4 |
| 100 | a | — | −22 |
| 101 | a | — | −25 |
| 102 | a | — | −15 |
| 103 | a | — | −20 |
| 104 | a | — | −15 |
| 105 | b | — | −24 |
| 106 | b | — | 0 |
| 107 | b | — | −17 |
| 108 | b | — | −19 |
| 109 | a | — | −23 |
| 110 | b | — | −23 |
| 111 | b | — | −25 |
| 112 | a | — | −9 |
| 113 | b | — | 0 |
| 114 | b | — | 0 |
| 115 | b | — | 0 |
| 116 | b | — | 0 |
| 117 | b | — | 0 |
| 118 | b | — | 0 |
| 119 | b | — | 0 |
| 120 | c | — | 0 |
| 121 | c | — | 0 |
| 122 | b | — | 0 |
| 123 | c | — | 0 |
| 124 | b | — | 0 |
| 125 | b | — | 0 |
| 126 | c | — | 0 |
| 127 | b | — | 0 |
| 128 | c | — | 0 |
| 129 | c | — | 0 |
| 130 | c | — | 0 |
| 131 | a | — | 0 |
| 132 | b | — | 0 |
| 133 | b | — | 0 |
| 134 | b | — | 0 |
| 135 | c | — | 0 |
| 136 | b | — | 0 |
| 137 | b | — | 0 |
| 138 | b | — | 0 |
| 139 | b | — | 0 |
| 140 | b | — | 0 |
| 141 | b | — | 0 |
| 142 | a | — | 0 |
| 143 | a | — | 0 |
| 144 | b | — | 0 |
| 145 | a | — | 0 |
| 146 | b | — | 0 |
| 147 | c | — | 0 |
| 148 | b | — | −12 |
| 149 | b | — | 0 |
| 150 | b | — | 0 |

In the table are listed the $IC_{50}$ values of the hMC-4R binding assay and the $EC_{50}$ values of the functional assay.
The $IC_{50}$ and $EC_{50}$ values were grouped in 3 classes:
a ≤ 0.1 μM;
b > 0.1 μM and ≤ 1.0 μM;
c > 1.0 μM

C. In Vivo Food Intake Models

1. Spontaneous Feeding Paradigm

Food intake in rats is measured after i.p. or p.o. administration of the test compound (see e.g. Chen, A. S. et al. Transgenic Res 2000 April; 9(2):145-54).

2. Models of LPS-Induced Anorexia and Tumor-Induced Cachexia

Prevention or amelioration of anorexia induced by lipopolysaccharide (LPS) administration or cachexia induced by tumor growth is determined upon i.p. or p.o. administration of test compounds to rats (see e.g. Marks, D. L.; Ling, N. and Cone, R. D. Cancer Res 2001 Feb. 15; 61(4):1432-8).

D. In Vitro ADME Assays

1. Microsomal Stability

Experimental Procedure

Pooled human liver microsomes (pooled male and female) and pooled rat liver microsomes (male Sprague Dawley rats) are prepared. Microsomes are stored at −80° C. prior to use.

Microsomes (final concentration 0.5 mg/ml), 0.1 M phosphate buffer pH7.4 and test compound (final substrate concentration=3 μM; final DMSO concentration=0.25%) are pre-incubated at 37° C. prior to the addition of NADPH (final concentration=1 mM) to initiate the reaction. The final incubation volume is 25 μl. A control incubation is included for each compound tested where 0.1 M phosphate buffer pH7.4 is added instead of NADPH (minus NADPH). Two control compounds are included with each species. All incubations are performed singularly for each test compound.

Each compound is incubated for 0, 5, 15, 30 and 45 min. The control (minus NADPH) is incubated for 45 min only. The reactions are stopped by the addition of 50 μl methanol containing internal standard at the appropriate time points. The incubation plates are centrifuged at 2,500 rpm for 20 min at 4° C. to precipitate the protein.

Quantitative Analysis

Following protein precipitation, the sample supernatants are combined in cassettes of up to 4 compounds and analysed using generic LC-MS/MS conditions.

Data Analysis

From a plot of the peak area ratio (compound peak area/internal standard peak area) against time, the gradient of the line is determined. Subsequently, half-life and intrinsic clearance are calculated using the equations below:

$$\text{Elimination rate constant } (k) = (-\text{gradient})$$

$$\text{Half life } (t_{1/2})(\text{min}) = \frac{0.693}{k}$$

$$\text{Intrinsic Clearance } (CL_{int})(\mu\text{l/min/mg protein}) = \frac{V \times 0.693}{t_{1/2}}$$

where $V$ = Incubation volume µl/mg microsomal protein.

Two control compounds are included in the assay and if the values for these compounds are not within the specified limits the results are rejected and the experiment repeated.

2. Hepatocyte Stability

Experimental Procedure

Suspensions of cryopreserved hepatocytes are used for human hepatocyte stability assay (pooled from 3 individuals). All cryopreserved hepatocytes are purchased from in Vitro Technologies, Xenotech or TCS.

Incubations are performed at a test or control compound concentration of 3 µM at a cell density of $0.5 \times 10^6$ viable cells/mL. The final DMSO concentration in the incubation is 0.25%. Control incubations are also performed in the absence of cells to reveal any non-enzymatic degradation.

Duplicate samples (50 µl) are removed from the incubation mixture at 0, 5, 10, 20, 40 and 60 min (control sample at 60 min only) and added to methanol, containing internal standard (100 µl), to stop the reaction.

Tolbutamide, 7-hydroxycoumarin, and testosterone are used as control compounds. The samples are centrifuged (2500 rpm at 4° C. for 20 min) and the supernatants at each time point are pooled for cassette analysis by LC-MS/MS using generic methods.

Data Analysis

From a plot of in peak area ratio (compound peak area/internal standard peak area) against time, the gradient of the line is determined. Subsequently, half-life and intrinsic clearance are calculated using the equations below:

$$\text{Elimination rate constant } (k) = (-\text{gradient})$$

$$\text{Half life } (t_{1/2})(\text{min}) = \frac{0.693}{k}$$

$$\text{Intrinsic Clearance } (CL_{int})(\mu\text{l/min/million cells}) = \frac{V \times 0.693}{t_{1/2}}$$

where $V$ = Incubation volume (µl)/number of cells

3. Caco-2 Permeability (Bi-directional)

Experimental Procedure

Caco-2 cells obtained from the ATCC at passage number 27 are used. Cells (passage number 40-60) are seeded on to Millipore Multiscreen Caco-2 plates at $1 \times 10^5$ cells/cm². They are cultured for 20 days in DMEM and media is changed every two or three days. On day 20 the permeability study is performed.

Hanks Balanced Salt Solution (HBSS) pH7.4 buffer with 25 mM HEPES and 10 mM glucose at 37° C. is used as the medium in permeability studies. Incubations are carried out in an atmosphere of 5% $CO_2$ with a relative humidity of 95%. On day 20, the monolayers are prepared by rinsing both basolateral and apical surfaces twice with HBSS at 37° C. Cells are then incubated with HBSS in both apical and basolateral compartments for 40 min to stabilize physiological parameters.

HBSS is then removed from the apical compartment and replaced with test compound dosing solutions. The solutions are made by diluting 10 mM test compound in DMSO with HBSS to give a final test compound concentration of 10 µM (final DMSO concentration 1%). The fluorescent integrity marker lucifer yellow is also included in the dosing solution. Analytical standards are made from dosing solutions. Test compound permeability is assessed in duplicate. On each plate compounds of known permeability characteristics are run as controls.

The apical compartment inserts are then placed into 'companion' plates containing fresh HBSS. For basolateral to apical (B-A) permeability determination the experiment is initiated by replacing buffer in the inserts then placing them in companion plates containing dosing solutions. At 120 min the companion plate is removed and apical and basolateral samples diluted for analysis by LC-MS/MS. The starting concentration ($C_0$) and experimental recovery is calculated from both apical and basolateral compartment concentrations.

The integrity of the monolayers throughout the experiment is checked by monitoring lucifer yellow permeation using fluorimetric analysis. Lucifer yellow permeation is low if monolayers have not been damaged. Test and control compounds are quantified by LC-MS/MS cassette analysis using a 5-point calibration with appropriate dilution of the samples. Generic analytical conditions are used.

If a lucifer yellow $P_{app}$ value is above QC limits in one individual test compound well, then an n=1 result is reported. If lucifer yellow $P_{app}$ values are above QC limits in both replicate wells for a test compound, the compound is re-tested. Consistently high lucifer yellow permeation for a particular compound in both wells indicates toxicity. No further experiments are performed in this case.

Data Analysis

The permeability coefficient for each compound ($P_{app}$) is calculated from the following equation:

$$P_{app} = \frac{dQ/dt}{C_0 \times A}$$

Where dQ/dt is the rate of permeation of the drug across the cells, $C_0$ is the donor compartment concentration at time zero and A is the area of the cell monolayer. $C_0$ is obtained from analysis of donor and receiver compartments at the end of the incubation period. It is assumed that all of the test compound measured after 120 min incubation was initially present in the donor compartment at 0 min. An asymmetry index (AI) is derived as follows:

$$AI = \frac{P_{app}(B-A)}{P_{app}(A-B)}$$

An asymmetry index above unity shows efflux from the Caco-2 cells, which indicates that the compound may have potential absorption problems in vivo.

The apparent permeability ($P_{app}$ (A-B)) values of test compounds are compared to those of control compounds, atenolol and propranolol, that have human absorption of approximately 50 and 90% respectively (Zhao, Y. H., et al., (2001). Evaluation of Human Intestinal Absorption Data and Subsequent Derivation of a Quantitative Structure-Activity Relationship (QSAR) with the Abraham Descriptors. *Journal of Pharmaceutical Sciences.* 90 (6), 749-784). Talinolol (a known P-gp substrate (Deferme, S., Mols, R., Van Driessche, W., Augustijns, P. (2002). Apricot Extract Inhibits the P-gp-Mediated Efflux of Talinolol. *Journal of Pharmaceutical Sciences.* 91(12), 2539-48)) is also included as a control compound to assess whether functional P-gp is present in the Caco-2 cell monolayer.

4. Cytochrome P450 Inhibition (5 Isoform $IC_{50}$ Determination))

Experimental Procedure

CYP1A Inhibition

Six test compound concentrations (0.05, 0.25, 0.5, 2.5, 5, 25 µM in DMSO; final DMSO concentration=0.35%) are incubated with human liver microsomes (0.25 mg/ml) and NADPH (1 mM) in the presence of the probe substrate ethoxyresorufin (0.5 µM) for 5 min at 37° C. The selective CYP1A inhibitor, alpha-naphthoflavone, is screened alongside the test compounds as a positive control.

CYP2C9 Inhibition

Six test compound concentrations (0.05, 0.25, 0.5, 2.5, 5, 25 µM in DMSO; final DMSO concentration=0.25%) are incubated with human liver microsomes (1 mg/ml) and NADPH (1 mM) in the presence of the probe substrate tolbutamide (120 µM) for 60 min at 37° C. The selective CYP2C9 inhibitor, sulphaphenazole, is screened alongside the test compounds as a positive control.

CYP2C19 Inhibition

Six test compound concentrations (0.05, 0.25, 0.5, 2.5, 5, 25 µM in DMSO; final DMSO concentration=0.25%) are incubated with human liver microsomes (0.5 mg/ml) and NADPH (1 mM) in the presence of the probe substrate mephenyloin (25 µM) for 60 min at 37° C. The selective CYP2C19 inhibitor, tranylcypromine, is screened alongside the test compounds as a positive control.

CYP2D6 Inhibition

Six test compound concentrations (0.05, 0.25, 0.5, 2.5, 5, 25 µM in DMSO; final DMSO concentration=0.25%) are incubated with human liver microsomes (0.5 mg/ml) and NADPH (1 mM) in the presence of the probe substrate dextromethorphane (5 µM) for 30 min at 37° C. The selective CYP2D6 inhibitor, quinidine, is screened alongside the test compounds as a positive control.

CYP3A4 Inhibition

Six test compound concentrations (0.05, 0.25, 0.5, 2.5, 5, 25 µM in DMSO; final DMSO concentration 0.26%) are incubated with human liver microsomes (0.25 mg/ml) and NADPH (1 mM) in the presence of the probe substrate midazolam (2.5 µM) for 5 min at 37° C. The selective CYP3A4 inhibitor, ketoconazole, is screened alongside the test compounds as a positive control.

For the CYP1A incubations, the reactions are terminated by the addition of methanol, and the formation of the metabolite, resorufin, is monitored by fluorescence (excitation wavelength=535 nm, emission wavelength=595 nm). For the CYP2C9, CYP2C19, CYP2D6, and CYP3A4 incubations, the reactions are terminated by the addition of methanol containing internal standard. The samples are then centrifuged, and the supernatants are combined, for the simultaneous analysis of 4-hydroxytolbutamide, 4-hydroxymephenyloin, dextrorphan, and 1-hydroxymidazolam plus internal standard by LC-MS/MS. Generic LC-MS/MS conditions are used. Formic acid in deionised water (final concentration=0.1%) is added to the final sample prior to analysis. A decrease in the formation of the metabolites compared to vehicle control is used to calculate an $IC_{50}$ value (test compound concentration which produces 50% inhibition).

5. Plasma Protein Binding (10%)

Experimental Procedure

Solutions of test compound (5 µM, 0.5% final DMSO concentration) are prepared in buffer (pH 7.4) and 10% plasma (v/v in buffer). The experiment is performed using equilibrium dialysis with the two compartments separated by a semi-permeable membrane. The buffer solution is added to one side of the membrane and the plasma solution to the other side. Standards are prepared in plasma and buffer and are incubated at 37° C. Corresponding solutions for each compound are analyzed in cassettes by LC-MS/MS.

Quantitative Analysis

After equilibration, samples are taken from both sides of the membrane. The solutions for each batch of compounds are combined into two groups (plasma-free and plasma-containing) then cassette analyzed by LC-MS/MS using two sets of calibration standards for plasma-free (7 points) and plasma-containing solutions (6 points). Generic LC-MS/MS conditions are used. Samples are quantified using standard curves prepared in the equivalent matrix. The compounds are tested in duplicate.

A control compound is included in each experiment.

Data Analysis $$fu = \frac{1 - ((PC - PF))}{(PC)}$$

fu=fraction unbound
PC=sample concentration in protein containing side
PF=sample concentration in protein free side
fu at 10% plasma is converted to fu 100% plasma using the following equation:

$$fu_{100\%} = \frac{fu_{10\%}}{10 - (9 * fu_{10\%})}$$

Examples of a Pharmaceutical Composition

As a specific embodiment of an oral composition of a compound of the present invention, 33 mg of Example 9 is formulated with sufficient finely divided lactose to provide a total amount of 580 to 590 mg to fill a size 0 hard gelatin capsule.

As another specific embodiment of an oral composition of a compound of the present invention, 37 mg of Example 17 is formulated with sufficient finely divided lactose to provide a total amount of 580 to 590 mg to fill a size 0 hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages, other than the preferred doses as set forth above, may be applicable as a consequence of the specific pharmacological responses observed and may vary depending upon the particular active compound selected, as well as from the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

The invention claimed is:
1. A compound according to formula (I)

or enantiomers, diastereomers, tautomers, or pharmaceutically acceptable salts thereof,
wherein
A is —NH—, —CH$_2$—, —CH$_2$—CH$_2$— or a bond;
X is H,
  phenyl,
  phenyl which is fused with a saturated heterocyclic 5- or 6-membered ring, wherein the heterocyclic ring may contain 1 or 2 heteroatoms selected from O and N and wherein the heterocyclic ring may further be optionally substituted by an oxo group,
  4 to 8-membered saturated or unsaturated heterocyclyl containing 1 or 2 heteroatoms selected from N, O and S,
  5- to 6-membered heteroaryl containing 1 or 2 heteroatoms selected from N, O and S, or —C(O)—R$^6$,
  wherein each phenyl, heterocyclyl and heteroaryl is optionally substituted by 1 to 3 R$^{14}$ and/or 1 R$^{4b}$ and/or 1 R$^5$;
R$^1$ and R$^2$ are independently from each other selected from
  H,
  C$_{1-6}$ alkyl,
  C$_{1-6}$ alkylene-O—C$_{1-6}$ alkyl,
  C$_{1-3}$ alkylene-heterocyclyl, and
  C$_{1-6}$ alkylene-C$_{3-7}$ cycloalkyl,
  wherein each alkyl, alkylene, heterocyclyl and cycloalkyl is optionally substituted by OH, or
R$^1$ and R$^2$ form together with the nitrogen atom to which they are attached a 5 to 6-membered ring which may additionally contain 1 oxygen atom in the ring and which ring is optionally substituted by one or more substituents selected from OH, C$_{1-6}$ alkyl, O—C$_{1-6}$ alkyl, C$_{0-3}$ alkylene-C$_{3-5}$ cycloalkyl, C$_{1-6}$ alkylene-O—C$_{1-6}$ alkyl or (CH$_2$)$_{0-3}$-phenyl;
R$^{4a}$ is halogen,
  CN,
  C$_{1-6}$ alkyl, optionally substituted with one or more halogen atoms,
  O—C$_{1-6}$ alkyl, optionally substituted with one or more halogen atoms, or
  OH;
R$^{4b}$ is C(O)NH$_2$,
  C(O)OH
  C(O)NH—C$_{1-6}$ alkyl,
  C(O)N—(C$_{1-6}$ alkyl)$_2$,
  SO$_2$—C$_{1-6}$ alkyl,
  C(O)NH—SO$_2$—C$_{1-6}$ alkyl,
  oxo, whereby the ring is at least partially saturated,
  NH$_2$,
  NH—C$_{1-6}$ alkyl,
  N—(C$_{1-6}$ alkyl)$_2$,
  NH—SO$_2$—CH$_3$, or
  NH—SO$_2$—CF$_3$;
R$^5$ is 5 to 6-membered saturated or unsaturated heterocyclyl containing 1 to 3 heteroatoms selected from N, O and S, or
  5 to 6-membered heteroaryl containing 1 to 3 heteroatoms selected from N, O and S,
  wherein the heterocyclyl and the heteroaryl are optionally substituted by 1 or 2 R$^{14}$;
R$^6$ is H,
  C$_{1-6}$alkyl, optionally substituted with one or more halogen atoms, phenyl or
  4 to 8-membered saturated or unsaturated heterocyclyl containing 1 to 3 heteroatoms selected from N, O and S,
  wherein each phenyl and heterocyclyl is optionally substituted by 1 to 3 R$^{14}$ and/or 1R$^5$;
R$^3$ is —(CR$^8$R$^9$)$_n$-T;
R$^8$ and R$^9$ are independently from each other selected from
  H,
  OH,
  halogen,
  C$_{1-6}$ alkyl, and
  O—C$_{1-6}$ alkyl;
n is 1, 2, 3, 4, 5 or 6;
T is or NR$^{12}$R$^{13}$;
R$^{10}$ is H,
  NH$_2$,
  OH,
  C$_{1-6}$ alkyl, optionally substituted by one or more substituents selected from halogen, OH, and O—C$_{1-6}$alkyl, O—C$_{1-6}$ alkyl, wherein alkyl is optionally substituted by one or more substituents selected from halogen, OH, and O—C$_{1-6}$ alkyl,
  halogen,
  NH(C$_{1-6}$ alkyl),
  N(C$_{1-6}$ alkyl)$_2$,
  phenyl or
  heteroaryl,
  wherein phenyl and heteroaryl are optionally substituted by 1 to 3 R$^{4a}$;
q is 1 or 2;
Y is CH$_2$, NR$^{11}$ or O;
R$^{11}$ is H,
  C$_{1-6}$alkyl or
  (CH$_2$)$_{0-6}$—C$_{3-7}$cycloalkyl;

$R^{12}$ and $R^{13}$ are independently from each other selected from
H,
$C_{1-6}$ alkyl,
$C_{2-6}$ alkenyl,
$C_{2-6}$ alkinyl,
$(CH_2)_{0-2}$—$C_{3-7}$ cycloalkyl and
$C_{1-6}$ alkylene-O—$C_{1-6}$ alkyl,
wherein $C_{1-6}$ alkyl, $C_{1-6}$ alkylene and $C_{3-7}$ cycloalkyl are optionally substituted by 1 to 3 $R^{14}$;
$R^{14}$ is halogen,
CN,
$C_{1-6}$ alkyl, optionally substituted with one or more substituents selected from halogen, OH, O—$C_{1-6}$ alkyl, O—$C_{3-7}$ cycloalkyl, O—C(O)$C_{1-6}$ alkyl, O—C(O)$C_{3-7}$ cycloalkyl,
O—$C_{1-6}$ alkyl, optionally substituted with one or more substituents selected from halogen, OH, O—$C_{1-6}$ alkyl, O—$C_{3-7}$ cycloalkyl, O—C(O)$C_{1-6}$ alkyl, O—C(O)$C_{3-7}$ cycloalkyl, or
OH.

2. The compound according to claim 1, wherein
A is —NH—, —$CH_2$—, —$CH_2$—$CH_2$— or a bond;
X is H,
phenyl,
phenyl which is fused with a saturated heterocyclic 6-membered ring, wherein the heterocyclic ring may contain 1 or 2 heteroatoms selected from O and N and wherein the heterocyclic ring may further be optionally substituted by an oxo group,
4 to 8-membered saturated or unsaturated heterocyclyl containing 1 or 2 heteroatoms selected from N, O and S,
5- to 6-membered heteroaryl containing 1 or 2 heteroatoms selected from N, O and S, or
—C(O)—$R^6$,
wherein each phenyl, heterocyclyl and heteroaryl is optionally substituted by 1 to 3 $R^{14}$ and/or 1 $R^{4b}$ and/or 1 $R^5$;
$R^1$ and $R^2$ are independently from each other selected from
H,
$C_{1-6}$ alkyl,
$C_{1-6}$ alkylene-O—$C_{1-6}$ alkyl,
$C_{1-3}$ alkylene-heterocyclyl, and
$C_{1-6}$ alkylene-$C_{3-7}$ cycloalkyl, or
$R^1$ and $R^2$ form together with the nitrogen atom to which they are attached a 5 to 6-membered ring which may additionally contain 1 oxygen atom in the ring and which ring is optionally substituted by one or more substituents selected from OH, $C_{1-6}$ alkyl, O—$C_{1-6}$ alkyl, $C_{0-3}$ alkylene-$C_{3-5}$ cycloalkyl, $C_{1-6}$ alkylene-O—$C_{1-6}$ alkyl or $(CH_2)_{0-3}$-phenyl;
$R^{4a}$ and $R^{14}$ are independently from each other selected from
halogen,
CN,
$C_{1-6}$ alkyl, optionally substituted with one or more halogen atoms,
O—$C_{1-6}$ alkyl, optionally substituted with one or more halogen atoms, or
OH;
$R^{4b}$ is C(O)$NH_2$,
C(O)NH—$C_{1-6}$ alkyl,
C(O)N—$(C_{1-6}$ alkyl$)_2$,
$SO_2$—$C_{1-6}$ alkyl,
C(O)NH—$SO_2$—$C_{1-6}$ alkyl,
$NH_2$,
NH—$C_{1-6}$ alkyl,
N—$(C_{1-6}$ alkyl$)_2$,
NH—$SO_2$—$CH_3$, or
NH—$SO_2$—$CF_3$;

$R^5$ is 5 to 6-membered saturated or unsaturated heterocyclyl containing 1 to 3 heteroatoms selected from N, O and S or
5 to 6-membered heteroaryl containing 1 to 3 heteroatoms selected from N, O and S,
wherein the heterocyclyl and the heteroaryl are optionally substituted by 1 or 2 $R^{14}$;
$R^6$ is H,
$C_{1-6}$ alkyl, optionally substituted with one or more halogen atoms, phenyl or
4 to 8-membered saturated or unsaturated heterocyclyl containing 1 to 3 heteroatoms selected from N, O and S,
wherein each phenyl and heterocyclyl is optionally substituted by 1 to 3 $R^{14}$ and/or 1 $R^5$;
$R^3$ is —$(CR^8R^9)_n$-T;
$R^8$ and $R^9$ are independently from each other selected from
H,
OH,
halogen,
$C_{1-6}$ alkyl, and
O—$C_{1-6}$ alkyl;
n is 1, 2, 3, 4, 5 or 6;
T is

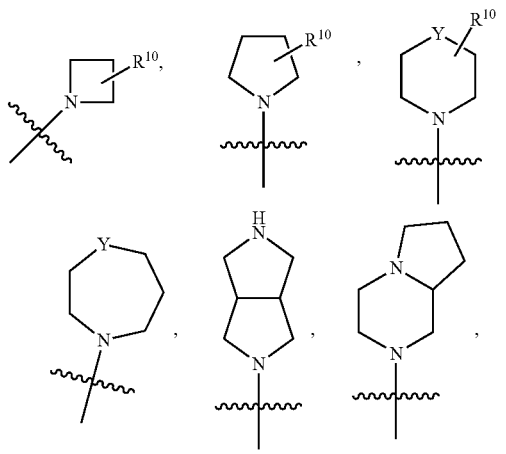

or $NR^{12}R^{13}$;
$R^{10}$ is H,
$NH_2$,
$C_{1-6}$ alkyl,
halogen,
NH($C_{1-6}$ alkyl),
N($C_{1-6}$ alkyl$)_2$,
phenyl or
heteroaryl,
wherein phenyl and heteroaryl are optionally substituted by 1 to 3 $R^{4a}$;
Y is $CH_2$, $NR^{11}$ or O;
$R^{11}$ is H,
$C_{1-6}$ alkyl or
$(CH_2)_{0-6}$—$C_{3-7}$ cycloalkyl;
$R^{12}$ and $R^{13}$ are independently from each other selected from
H,
$C_{1-6}$ alkyl,
$(CH_2)_{0-2}$—$C_{3-7}$ cycloalkyl and
$C_{1-6}$ alkylene-O—$C_{1-6}$ alkyl;
wherein $C_{1-6}$ alkyl, $C_{1-6}$ alkylene and $C_{3-7}$ cycloalkyl are optionally substituted by 1 to 3 $R^{14}$.

3. The compound of claim 1, wherein A is —NH— or a bond.

4. The compound of claim 1, wherein $R^1$ and $R^2$ are independently from each other $C_{3-6}$ alkyl or $R^1$ and $R^2$ form together with the nitrogen atom to which they are attached a 5 to 6-membered ring which may additionally contain 1 oxygen atom in the ring and which ring is optionally substituted by one or more substituents selected from OH, $C_{1-6}$ alkyl, $C_{0-3}$ alkylene-$C_{3-5}$ cycloalkyl, O—$C_{1-6}$ alkyl, $C_{1-6}$ alkylene-O—$C_{1-6}$ alkyl or $(CH_2)_{0-3}$-phenyl.

5. The compound of claim 1, wherein T is $NR^{12}R^{13}$.

6. The compound of claim 5, wherein $R^{12}$ and $R^{13}$ are independently from each other selected from H, $C_{1-3}$ alkyl and $(CH_2)_{0-2}$—$C_{3-6}$ cycloalkyl, wherein alkyl and cycloalkyl are optionally substituted by 1 to 3 $R^{14}$.

7. The compound of claim 1, wherein T is selected from

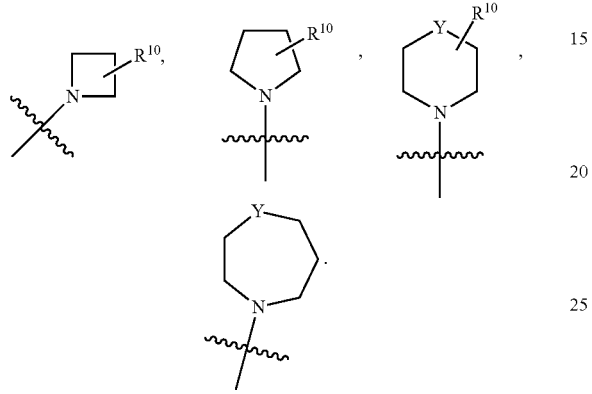

8. The compound of claim 7, wherein Y is $CH_2$ or $NR^{11}$ and $R^{10}$ is H, $NH_2$, $C_{1-6}$ alkyl, $NH(C_{1-6}$ alkyl$)$ or $N(C_{1-6}$ alkyl$)_2$.

9. The compound of claim 1, wherein
X is H,
  phenyl which is fused with a saturated heterocyclic 6-membered ring,
    wherein the heterocyclic ring may contain 1 or 2 heteroatoms selected from O and N and wherein the heterocyclic ring may further be optionally substituted by an oxo group, or
  4 to 8-membered saturated or unsaturated heterocyclyl containing 1 or 2 heteroatoms selected from N, O and S,
    wherein each phenyl or heterocyclyl is optionally substituted by 1 to 3 $R^{14}$ and/or 1 $R^5$.

10. The compound of claim 1, wherein
X is phenyl or
  5 to 6-membered heteroaryl containing 1 or 2 heteroatoms selected from N, O and S,
    wherein each phenyl and heteroaryl is optionally substituted by 1 to 3 $R^{14}$ and/or 1 $R^{4b}$ and/or 1 $R^5$.

11. The compound of claim 10, wherein X is phenyl.

12. The compound of claim 10, wherein X is pyridyl.

13. The compound of claim 1, wherein said compound is a melanocortin-4 receptor antagonist.

14. A pharmaceutical composition comprising the compound of claim 1 and a pharmaceutically acceptable carrier.

* * * * *